(12) United States Patent
Favuzzi et al.

(10) Patent No.: US 7,850,912 B2
(45) Date of Patent: Dec. 14, 2010

(54) METHOD AND APPARATUS FOR AUTOMATED PRE-TREATMENT AND PROCESSING OF BIOLOGICAL SAMPLES

(75) Inventors: John A. Favuzzi, Santa Barbara, CA (US); Marc E. Key, Ojai, CA (US); Robert L. Lathrop, San Jose, CA (US); Gordon A. Feingold, Santa Barbara, CA (US); Rosanne Welcher, Ventura, CA (US)

(73) Assignee: DAKO Denmark A/S (DE)

( * ) Notice: Subject to any disclaimer, the term of this patent is extended or adjusted under 35 U.S.C. 154(b) by 1162 days.

(21) Appl. No.: 11/227,270

(22) Filed: Sep. 16, 2005

(65) Prior Publication Data

US 2006/0148063 A1    Jul. 6, 2006

Related U.S. Application Data

(63) Continuation-in-part of application No. PCT/DK03/00877, filed on Dec. 15, 2003, and a continuation-in-part of application No. PCT/DK03/00911, filed on Dec. 19, 2003, and a continuation-in-part of application No. PCT/US03/40518, filed on Dec. 19, 2003, and a continuation-in-part of application No. PCT/US03/40591, filed on Dec. 19, 2003, and a continuation-in-part of application No. PCT/US03/40520, filed on Dec. 19, 2003, and a continuation-in-part of application No. PCT/US03/40974, filed on Dec. 19, 2003, and a continuation-in-part of application No. PCT/US03/40519, filed on Dec. 19, 2003, and a continuation-in-part of application No. PCT/US03/40880, filed on Dec. 22, 2003, and a continuation-in-part of application No. PCT/US03/41022, filed on Dec. 22, 2003, and a continuation-in-part of application No. PCT/DK2004/000179, filed on Mar. 18, 2004, and a continuation-in-part of application No. PCT/US2005/006383, filed on Feb. 28, 2005, and a continuation-in-part of application No. 11/168,987, filed on Jun. 28, 2005, and a continuation-in-part of application No. 11/177,730, filed on Jul. 8, 2005, now abandoned.

(60) Provisional application No. 60/697,591, filed on Jul. 7, 2005, provisional application No. 60/697,813, filed on Jul. 7, 2005, provisional application No. 60/682,046, filed on May 18, 2005.

(51) Int. Cl.
*G01N 33/00* (2006.01)

(52) U.S. Cl. .............................. 422/63; 422/62; 422/99; 422/100; 422/102

(58) Field of Classification Search .................. 422/62, 422/63, 64, 65, 99, 100, 102
See application file for complete search history.

(56) References Cited

U.S. PATENT DOCUMENTS 4,276,051 A * 6/1981 Ginsberg et al. .............. 436/47

(Continued)

FOREIGN PATENT DOCUMENTS

DE    4313807    11/1993

(Continued)

OTHER PUBLICATIONS

Juroshek et al., A High-Power Automatic Network Analyzer for Measuring the RF Power Absorbed by Biological Samples in a TEM Cell, 1984, IEEE, gpo 818-824.

(Continued)

*Primary Examiner*—Sam P Siefke
(74) *Attorney, Agent, or Firm*—Finnegan, Henderson, Farabow, Garrett & Dunner, LLP

(57) ABSTRACT

A method and apparatus for continuous workflow processing of biological samples. In one embodiment, the apparatus includes a probe for dispensing one or more reagents from one or more reagent containers onto one or more biological sample carriers. The method and apparatus includes processing each biological sample according to a respective sequence of protocol steps which may be ordered by a scheduler protocol. The method and apparatus also includes network capability for connectivity with additional equipment for receiving or transmitting pertinent data via the network.

33 Claims, 55 Drawing Sheets

U.S. PATENT DOCUMENTS

| | | |
|---|---|---|
| 4,311,667 A | 1/1982 | Gocho |
| 4,967,606 A | 11/1990 | Wells et al. |
| 5,068,091 A | 11/1991 | Toya |
| 5,073,504 A | 12/1991 | Bogen |
| 5,289,385 A | 2/1994 | Grandone |
| 5,338,358 A | 8/1994 | Mizusawa et al. |
| 5,346,672 A | 9/1994 | Stapleton et al. |
| 5,355,439 A | 10/1994 | Bernstein et al. |
| 5,380,486 A | 1/1995 | Anami |
| 5,399,316 A | 3/1995 | Yamada |
| 5,425,918 A | 6/1995 | Healey et al. |
| 5,439,649 A | 8/1995 | Tseung et al. |
| 5,552,087 A | 9/1996 | Zeheb et al. |
| 5,573,727 A | 11/1996 | Keefe |
| 5,578,452 A | 11/1996 | Shi et al. |
| 5,595,707 A | 1/1997 | Copeland et al. |
| 5,646,049 A | 7/1997 | Tayi |
| 5,650,327 A | 7/1997 | Copeland et al. |
| 5,654,199 A | 8/1997 | Copeland et al. |
| 5,654,200 A | 8/1997 | Copeland et al. |
| 5,696,887 A | 12/1997 | Bernstein et al. |
| 5,839,091 A | 11/1998 | Rhett et al. |
| 5,896,488 A | 4/1999 | Jeong |
| 5,948,359 A | 9/1999 | Kalra et al. |
| 5,963,368 A | 10/1999 | Domanik et al. |
| 6,019,945 A * | 2/2000 | Ohishi et al. ............... 422/65 |
| 6,045,759 A | 4/2000 | Ford et al. |
| 6,080,363 A | 6/2000 | Takahashi et al. |
| 6,093,574 A | 7/2000 | Druyor-Sanchez et al. |
| 6,096,271 A | 8/2000 | Bogen et al. |
| 6,296,809 B1 | 10/2001 | Richards et al. |
| 6,349,264 B1 | 2/2002 | Rhett et al. |
| 6,352,861 B1 | 3/2002 | Copeland et al. |
| 6,403,036 B1 | 6/2002 | Rodgers et al. |
| 6,403,931 B1 | 6/2002 | Showalter et al. |
| 6,405,609 B1 | 6/2002 | Richards et al. |
| 6,451,551 B1 | 9/2002 | Zhan et al. |
| 6,472,217 B1 | 10/2002 | Richards et al. |
| 6,495,106 B1 | 12/2002 | Kalra et al. |
| 6,534,008 B1 | 3/2003 | Angros |
| 6,544,798 B1 | 4/2003 | Christensen et al. |
| 6,582,962 B1 | 6/2003 | Richards et al. |
| 6,632,598 B1 | 10/2003 | Zhang et al. |
| 6,635,225 B1 | 10/2003 | Thiem et al. |
| 6,735,531 B2 | 5/2004 | Rhett et al. |
| 6,746,851 B1 | 6/2004 | Tseung et al. |
| 6,800,249 B2 | 10/2004 | De La Torre-Bueno |
| 6,821,072 B2 | 11/2004 | Thiem et al. |
| 6,855,559 B1 | 2/2005 | Christensen et al. |
| 7,135,992 B2 | 11/2006 | Karlsson et al. |
| 7,142,852 B2 | 11/2006 | Tell et al. |
| 7,226,788 B2 | 6/2007 | De La Torre-Bueno |
| 7,303,725 B2 | 12/2007 | Reinhardt et al. |
| 7,378,055 B2 | 5/2008 | Lemme et al. |
| 7,396,508 B1 | 7/2008 | Richards et al. |
| 7,400,983 B2 | 7/2008 | Feingold et al. |
| 7,404,927 B2 | 7/2008 | Lemme et al. |
| 2002/0001849 A1 | 1/2002 | Copeland et al. |
| 2002/0072122 A1 | 6/2002 | Copeland et al. |
| 2002/0114733 A1 | 8/2002 | Copeland et al. |
| 2003/0099573 A1 | 5/2003 | Tseung et al. |
| 2003/0100043 A1 | 5/2003 | Kalra et al. |
| 2003/0120633 A1 | 6/2003 | Torre-Bueno |
| 2004/0033163 A1 | 2/2004 | Tseung et al. |
| 2004/0219069 A1 | 11/2004 | Kalra et al. |
| 2004/0265185 A1 | 12/2004 | Kitagawa |
| 2004/0266015 A1 | 12/2004 | Favuzzi et al. |
| 2005/0038676 A1 | 2/2005 | Showalter et al. |
| 2005/0064535 A1 | 3/2005 | Favuzzi et al. |
| 2005/0124028 A1 | 6/2005 | Windeyer et al. |
| 2005/0159982 A1 | 7/2005 | Showalter et al. |
| 2006/0045806 A1 | 3/2006 | Winther et al. |
| 2006/0046298 A1 | 3/2006 | Key et al. |
| 2006/0063265 A1 | 3/2006 | Welcher et al. |
| 2006/0085140 A1 | 4/2006 | Feingold et al. |
| 2006/0088928 A1 | 4/2006 | Sweet et al. |
| 2006/0088940 A1 | 4/2006 | Feingold et al. |
| 2006/0105359 A1 | 5/2006 | Favuzzi et al. |
| 2006/0148063 A1 | 7/2006 | Favuzzi et al. |
| 2006/0265133 A1 | 11/2006 | Cocks et al. |
| 2007/0010912 A1 | 1/2007 | Feingold et al. |
| 2007/0196909 A1 | 8/2007 | Showalter et al. |

FOREIGN PATENT DOCUMENTS

| | | |
|---|---|---|
| JP | 03209163 A2 | 12/1991 |
| WO | WO 95/10035 | 4/1995 |
| WO | WO 97/26541 | 7/1997 |
| WO | WO 99/43434 | 9/1999 |
| WO | WO 00/02660 | 1/2000 |
| WO | WO 01/51909 | 7/2001 |
| WO | WO 01/68259 | 9/2001 |
| WO | WO 01/88500 | 11/2001 |
| WO | WO 02/056121 | 7/2002 |
| WO | WO 03/045560 | 6/2003 |
| WO | WO 03/052386 | 6/2003 |
| WO | WO 2004/074845 | 9/2004 |
| WO | WO 2004/074847 | 9/2004 |
| WO | WO 2005/031312 | 4/2005 |

OTHER PUBLICATIONS

Meldrum et al., Acapella. a capillary-based submicroliter automated sample preparation system for genome analysis, 1999, IEEE, p. 39-48.

Shepard, DNA purification robotics system, 1994, IEEE, gpo 424-425.

Suckau et al., Automation of MALDI-TOF Analysis for Proteomics, 1999, IEEE, pp. 1-5.

Histologic, Technical Bulletin or Histotechnology, 2001, Internet, pp. 21-44.

Garrett et al., Successful techniques for supporting multidisciplinary science programs with 'ROPOS: 1999, IEEE, pp. 753-756.

Office Action dated Mar. 18, 2010, cited in U.S. Appl. No. 10/536,964, filed Jun. 14, 2005, Sweet et al.

Office Action dated Apr. 15, 2010, cited in U.S. Appl. No. 10/539,561, filed Jun. 16, 2005, Key et al.

* cited by examiner

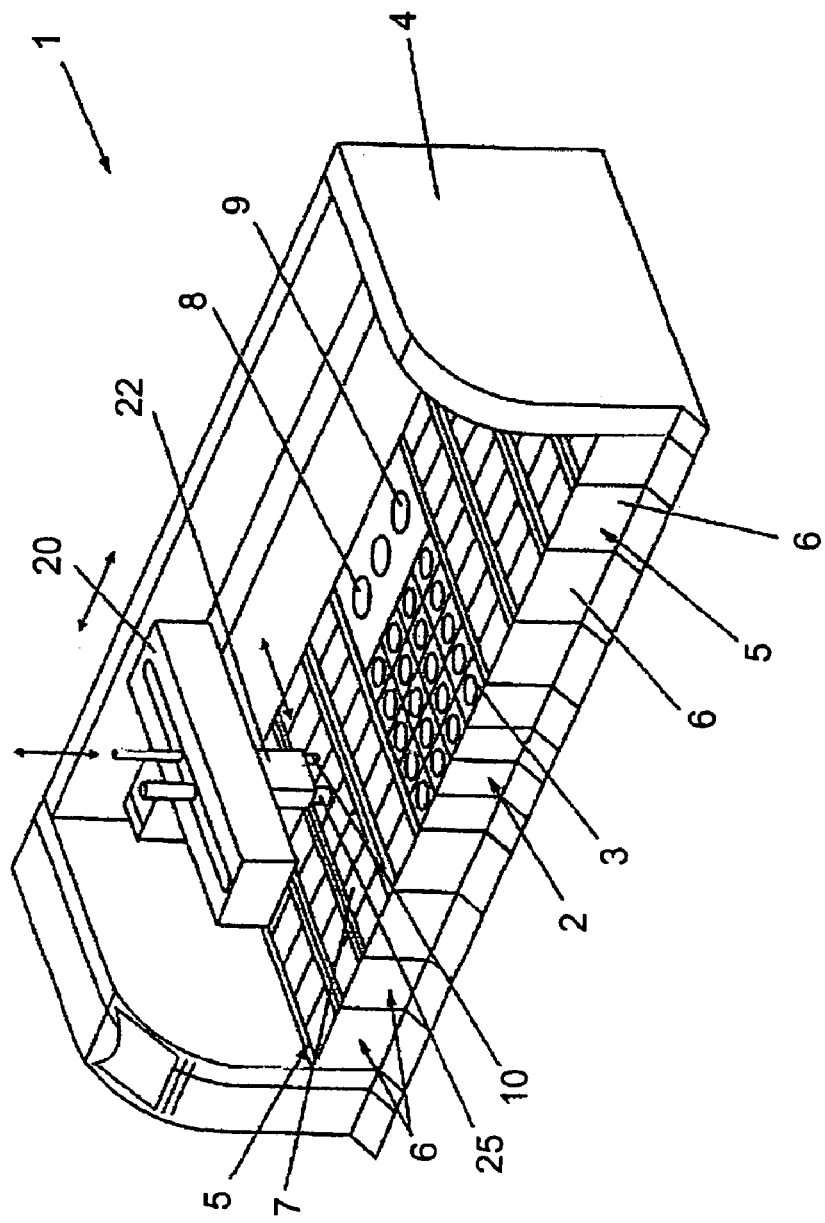
FIG. 1β

| Process | Protocol Step | Time (min) | Temp C | Waste Segregation |
|---|---|---|---|---|
| Deparaffinization | Switch | | | Hazardous Waste |
| | Histoclear | 5 | | |
| | Drain | | | |
| | Histoclear | 5 | | |
| | Drain | | | |
| Re-Hydration | 100% Ethanol | 5 | | |
| | Drain | | | |
| | 100% Ethanol | 5 | | |
| | Drain | | | |
| | 95% Ethanol | 5 | | |
| | Drain | | | |
| | 95% Ethanol | 5 | | |
| | Rinse - Water | 5 | | |
| | Switch | | | Non-Hazardous Waste |
| Target Retrieval | Target Retrieval | 40-55 | 95 | |
| | Target Retrieval Cool | 10 | 55 | |
| | Rinse - Water | 5 | RT | |
| Enzyme/Antibody Application | Peroxide Block | 5 | | |
| | Enzyme Pretreatment | 5 | | |
| | Rinse - Buffer | | | |
| | Pre-Diluted Antibody | 10-20 | | |
| | Rinse - Buffer | | | |
| | Detection Reagents | 10-30 | | |
| Chromogen/ Counterstain Treatment | Rinse - Buffer | | | |
| | Switch | | | Hazardous Waste |
| | Chromogen | 10 | | |
| | Rinse - Buffer | | | |
| | Hematoxylin | 8 | | |
| | Rinse - Water | | | |

FIG. 5

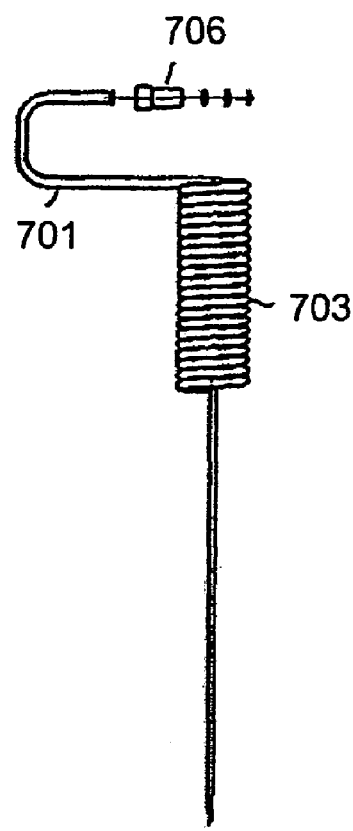
FIG. 9

SCS STAINER API BLOCK DIAGRAM
2000

METHOD AND APPARATUS FOR AUTOMATED PRE-TREATMENT AND PROCESSING OF BIOLOGICAL SAMPLES

CROSS REFERENCE TO RELATED APPLICATIONS

This application claims priority to U.S. Provisional Application Nos. 60/697,591 and 60/697,813, filed Jul. 7, 2005 and 60/682,046, filed on May 18, 2005, the disclosures of which are herein incorporated by reference.

This application is a continuation-in-part of the US national phase entries of international applications: PCT/DK2003/000877, having an international filing date of Dec. 15, 2003; PCT/DK2003/000911, having an international filing date of Dec. 19, 2003; PCT/US2003/040518, having an international filing date of Dec. 19, 2003; PCT/US2003/040880, having an international filing date of Dec. 22, 2003; PCT/US2003/040591, having an international filing date of Dec. 19, 2003; PCT/US2003/040520, having an international filing date of Dec. 19, 2003; PCT/US2005/006383 having an international filing date of Feb. 28, 2005; PCT/US2003/041022 having an international filing date of Dec. 22, 2003; PCT/US2003/040974 having an international filing date of Dec. 19, 2003; and PCT/US2003/040519 having an international filing date of Dec. 19, 2003, the disclosures of which are herein incorporated by reference.

This application is also a continuation-in-part of PCT Application No. PCT/DK2004/000179, filed on Mar. 18, 2004, and U.S. patent application Ser. No. 11/168,987, filed on Jun. 28, 2005 and Ser. No. 11/177,730, filed Jul. 8, 2005 now abandoned, the disclosures of which are herein incorporated by reference.

This application also incorporates by reference European Patent Application 03076463.3 filed on May 14, 2003. Also hereby incorporated by reference is each one of the patent application publications corresponding to the above-referenced international applications, said patent application publications being, namely, international patent application publications: WO 2004/057307 A1, WO 2004/057308 A1, WO 2004/058950 A1, WO 2004/059287 A2, WO 2004/058404 A2, WO 2004/059284 A2, WO 2004/059288 A2, WO 2004/059441 A2, and WO 2004/059297 A1.

This application also incorporates by reference: U.S. Provisional Application Ser. Nos. 60/435,601 filed Dec. 20, 2002; and 60/549,889 filed on Mar. 2, 2004; U.S. patent application Ser. No. 10/741,628 filed on Dec. 19, 2003; Ser. No. 10/731,316 filed on Dec. 8, 2003; Ser. No. 11/119,417, filed on Apr. 30, 2005; and Ser. No. 11/156,760, filed on Jun. 20, 2005; and United States patent application entitled "SYSTEMS AND METHODS FOR THE AUTOMATED PRE-TREATMENT AND PROCESSING OF BIOLOGICAL SAMPLES", filed on Sep. 16, 2004.

SUMMARY OF THE INVENTION AND BACKGROUND

The present invention relates generally, in one embodiment, to the preparation of biological samples. For example, the present invention, in one embodiment, relates to a system and method for the automated, continuous work flow, pre-treatment and processing of biological samples.

In this disclosure, the term "staining" is used to refer to the end product of a process, by which certain parts of the sample may be stained, i.e. have obtained a different color, either in the optic range or in another electromagnetic range, such as ultra violet, or the staining may be a detectable (e.g., automatically detectable) change in properties, such as fluorescent properties, magnetic properties, electrical properties or radioactive properties. To obtain the staining, the sample may undergo a series of treatment steps, such as—but not limited to—washing, binding of reagents to the specific parts of the sample, application of the reagents, etc. and each treatment step may include a plurality of individual treatments.

Examples of sample preparation and processing that may be used in the practice of the invention include but are not limited to the following.

Sample processing in immunohistochemical (IHC) applications and in other chemical and biological analyses may involve one or a number of various processing sequences or protocols as part of an analysis of one or more samples. The sample processing sequences or protocols may be defined by the individual or organization requesting an analysis, such as a pathologist or histologist of a hospital, and may be further defined by the dictates of a particular analysis to be performed.

In preparation for sample analysis, a biological sample may be acquired by known sample acquisition techniques and may comprise, for example, in IHC applications, tissues generally or, even, in some applications one or a plurality of isolated cells, such as in microarray samples, and may be presented on a microscope slide or a similar plane, rectangular sample carrier. Furthermore, the sample may be presented on the slide or other carrier variously and potentially in some form of preservation. As one example, a sample such as a layer or slice of skin may be preserved in formaldehyde and presented on a slide with one or more paraffin or other chemical layers overlying the sample. Samples preserved with paraffin may need to undergo deparaffinization, a process by which paraffin layers overlaying the sample are removed. In addition, the target or sample may need to be restored to a condition where it is suitable for staining operations—a process known as target retrieval.

Immunologic applications, for example, may involve processing sequences or protocols that comprise steps such as deparaffinization, target retrieval, and staining, especially for in-situ hybridization (ISH) techniques. Previously, in some applications, these steps may have been performed manually, potentially creating a time-intensive protocol and necessitating personnel to be actively involved in the sample processing. Attempts have been made to automate sample processing to address the need for expedient sample processing and a less manually burdensome operation. However, such previous efforts may have not fully addressed the needs for an automated sample processing system. Some prior efforts to automate sample processing may be deficient in several aspects that prevent more robust automated sample processing, such as: the lack of sufficient computer control and monitoring of sample processing; the lack of information sharing for processing protocol and processing status, especially for individual samples; the lack of diagnostic capabilities; and the lack of real-time or adaptive capabilities for multiple sample group processing. At least one of these may be found in embodiments of the present invention.

The staining procedure may be laborious and use many different reagents. The staining protocol may include the following steps: deparaffinization, washing, antigen retrieval, endogenous biotin or enzyme blocking, incubation with immunological reagents, molecular probes, secondary visualization reagents and various chromogen reagents, washing steps and counterstaining.

Certain methods for mixing reagents and liquids have been in practice, for example, in the context of mixing processes for staining instruments such as IHC and ISH equipment.

However, in some applications, such mixing processes have been cumbersome. Thus, some existing systems may have disadvantages in their implementation of mixing processes, for example, due to the complex use of reagents in the staining procedure. Below, a few non-limiting examples are listed in more detail. These examples may be useful and applied to the practice of the invention.

The chromogen reagents (e.g. DAB, AEC, fast red etc) often come as concentrated reagents in organic or high viscosity solutions and need to be diluted prior to being applied to the sample. Chromogens like the Fast Red alkaline phosphatase chromogen are made ready for use by mixing and dilution of two or three reagents, which are very different in nature with regard to salt content, viscosity and density. Furthermore, the resulting mixtures are unstable over time and need to be used within a short time. Some chromogens suitable for e.g. horseradish peroxidase, like DAB and AEC, are easily oxidized when exposed to air during e.g. vigorous mixing or dilution.

The enzyme chromogens and counter-stain reagents (e.g., hematoxylin) are semi oxidized and can contain precipitates and solids. By further oxidation or slight change in pH, the reagents can further precipitate.

Antibody and enzyme containing reagents often contain stabilizing proteins and or detergents, which cause the solution to foam when being shaken or stirred. Many proteins cannot easily tolerate to be exposed to the hydrophobic air in foam. Wash buffers can contain detergents, which can foam when shaken or stirred. The foam can spread to other compartments of the instrument in an unwanted and unpredictable way. Mixing of some reagents (e.g. the HRP chromogens and peroxide reagents) can result in the formation of small bubbles. These can generate foam or bubbling on the surface of the mixture.

Spill over/carry over is often undesirable. The staining process may be characterized by using many, complex and very different reagents and buffers and in many different dilution ratios and mixtures. Some of the reagents or buffers are incompatible with each other. In the event of cross contamination due to e.g. carry over, the reagents may be ruined within seconds or solids can precipitate, making the staining unsuccessful. For example, enzyme containing reagents can not be mixed with the corresponding chromogens, or high salt concentrates may not be mixed with e.g. proteins containing mixtures, or organic solvents can not be mixed with protein containing mixtures, or highly pH buffered wash buffers can not be mixed with low buffered mixtures without significantly altering the properties of the reagents. Accordingly a need exists for cleansing and washing of the mixing device in an efficient manner.

As some procedures may be regarded as complex, existing instruments may use many different protocols resulting in less predictable results due to even minute amounts of reagent carry-over or unplanned mixing of reagents. Reagent mixing efficiency may be, in part, affected by a software protocol and how it attempts to group an application of reagent mixtures on sample carriers such as slides so as to maximize efficiency, for instance, by minimizing reagent waste. Consequently, it may be desired for a mixing device for an automatic biological sample processing apparatus ideally to be very efficient and to be designed for a variety of reagent mixing protocols and sequences. It may be further desirable to provide on-demand mixing of reagents within a continuous processing environment.

During staining, build-up of small fouling layers on the various surfaces may cause problems, as the typical staining protocol calls for many mixing and dilution steps. Consequently, in one embodiment of the invention, the mixing device may have a minimum of surface area and very smooth surfaces. Furthermore, the mixing device may ideally be able to mix very different volumes of reagents in both small and large volumes ratios. In other words, the degree of dilution and mixing ratios of reagents may vary from small to high ratios. In summary, the mixing device in one embodiment, may ideally allow at least one of: mixing of small and large volumes; mixing reagents with different viscosities and densities; mixing of immiscible or nearly immiscible reagents; no fouling of mixing rods or similar due to precipitated material; easy escape of formed gasses during mixing; prevention of foaming of e.g. detergent or protein containing reagents; low build-up of debris or fouling on the device surfaces; easy emptying and washing—regardless of volumes; and very low reagent carry-over. At least some present mixing systems for automated biological sample processing do not truly fulfill one or more of the above-mentioned properties. On-the-slide mixing may not allow for very large ratios of dilution. It may also not allow for efficient mixing of reagents with very different densities or viscosities. In one embodiment, on-slide mixing is used as an alternative means to reagent mixing, for example, as described in U.S. patent application Ser. No. 11/177/730, filed Jul. 8, 2005, the disclosure of which is hereby incorporated by reference.

Further, a defined staining protocol, for use in the invention, may include one or more defined temperatures. For many IHC applications, and many sample processing sequences and protocols, it may be desired generally to have temperature characteristics associated with the sample, sample carrier, and the processing environment. Traditional sample processing technology, which also may be used in the practice of the invention, has provided temperature control through heating devices that heat an entire set of sample carriers in the sampling processing system. Other technologies, such as the sample processing system described in U.S. Pat. No. 6,183,693, may provide heating devices for individual sample carriers that are individually controlled to heat the slides. However, each of these traditional sample processing systems may lack a desired degree of temperature control or temperature tolerances.

Inadequacies in temperature control of traditional technologies may include uncontrolled cooling. Traditional systems may only provide ambient cooling when the heating devices are off. Ambient cooling is not considered active control and may not meet protocol temperature requirements or may not otherwise be optimal. Although heating and heat control may be features of such systems, controlled cooling of the samples, sample carriers, and processing environments may not always be adequately addressed. Cooling techniques such as hooded fans may be incorporated in some traditional technologies. However, these devices can lack sufficient capabilities of temperature control to meet certain protocol requirements, especially temperature tolerances for samples, sample carriers, reagents, and ambient system temperature.

Traditional systems may even lack temperature control, perhaps as related to temperature tolerances generally, as such tolerances may not be adequately maintained during ambient or other traditional cooling, or during processing sequences or events, generally. In some protocols, for example, the temperature tolerances during non-heating periods may be such that uncontrolled temperature changes may produce undesirable results during the processing sequence. Other IHC processes of the protocol may be adversely affected by uncontrolled temperature changes, the degree of temperature change, and temperature changes outside of acceptable tolerances. The lack of temperature control may actually dissuade technologists from employing automated processing sequences or protocols, especially IHC sequences, that may be dependent upon a particular temperature tolerance and the amount of temperature change during a processing sequence.

Certain types of temperature control may not have even been addressed in traditional sample processing system technologies. In one embodiment of the present invention, reagent temperatures are controlled. Reagents can play a vital role in the staining sequence of many processing protocols. The quality of the reagents, therefore, may be important for adequate sample processing. Reagents, for example, can have a certain shelf life that may be limited if maintained at undesirable temperatures such as the typical ambient temperatures of traditional biological sample processing systems and the laboratories housing such systems. Traditional technologies may lack the temperature control needed to optimally preserve the reagents stored in the processing system that are often subject to inadequate or changing ambient temperatures of such systems and the laboratory environment.

In one embodiment, sample processing apparatuses for staining and treating samples by means of probes may comprises a first section or station for containing one or more reagent containers, such as bottles or vials; a second section or station for mounting slides, a probe arranged to aspirate a portion of reagent from a selected reagent container and dispensing the reagent to a slide on which the sample is arranged and a drive means for moving the probe between the various sections.

Past efforts at automated sample processing for samples presented on carriers such as slides, such as U.S. Pat. No. 6,352,861 and U.S. Pat. No. 5,839,091, have not afforded at least some of the advantages and other combinations of features as presented herein. U.S. Pat. No. 5,948,359 discloses an apparatus of the above mentioned type, wherein the first station comprises a vial holder for holding 40 or more vials in order to provide a wide range of different reagents adapted for different staining purposes, and thereby the possibility of automatically staining a large number of slides requiring different staining processes. In practice it is often desired that the apparatus facilitates that many different staining processes can be performed at the same time in the apparatus, because this avoids the necessity of grouping samples requiring the same procedure or other treatment with reagents, and processing each group individually.

Currently available biological staining apparatuses do not provide for sample pre-treatment. In one embodiment of the present invention, a staining apparatus provides for pre-treatment. Biological samples, such as tissue samples, are usually prepared before the staining can be performed. The tissue slides are subjected to a pre-treatment process depending upon the type of staining process that is to be performed on the tissue. This pre-treatment could include deparaffinization or target retrieval. The preparation of the tissues on the slides is often carried out manually in the laboratory before they are loaded into the automatic staining instrument. This pre-treatment includes immersing the slide, for example, in one or more buffers or other types of processing liquid for a predetermined amount of time and temperature. Immersion processes may include multiple processing liquids such as in a specified sequence of processing liquids such as in a specified sequence of processing liquids. Unfortunately, however, this manual preparation may be cumbersome and the pre-treatment may be insufficient, since the amount of time and the temperature of the liquid should be observed substantially precisely in order to achieve the correct pre-treatment result. For example, pre-treatment may consist of multiple-step deparaffinization sequence of fluids that remove paraffin used to preserve tissue samples and/or heat-induced antigen retrieval which consists of immersion in or more fluids for specific periods at specific temperatures. Preparation of the aforementioned pre-treatment processes and the like may be difficult to achieve via manual preparation.

In the U.S. Pat. No. 5,839,091, an automated staining apparatus is disclosed wherein a plurality of biological samples accommodated on microscope slides may be processed. However this instrument does not provide a processing tank for pre-treatment of the slides.

Some staining processes involve the use of hazardous materials, such as toxic materials. These materials may be collected in special containers in order to ensure safe handling of the waste material. However, this does not sufficiently protect the laboratory environment in which the apparatus is placed from being contaminated with toxic material. Moreover, in some staining processes or other treatments in the apparatus, heat is applied. This increases the risk of vaporizing reagents which then may escape to the outside of the apparatus.

In some apparatuses, a protective hood or similar plastic cover have been put over the staining apparatus in order to shield off the biological samples during the staining. In this known technique, one may risk the drying out of slides and lack of control of airspeed and temperature.

Some staining apparatuses require existing sequences to finish before inserting or changing the aggregate in some manner. In one embodiment of the invention, a staining apparatus is provided that is capable of providing pre-treatment processes, for example, to carriers containing samples which may be conducted independently and simultaneously with processing other carriers containing samples that are also undergoing pre-treatment or staining sequences asynchronously. In addition, operators often have needed particular knowledge and skills in order to assure the integrity of the process, the instrument, or the result. Thus, one embodiment of the invention reduces such effects by providing a system which is more user, operator, supplier, and/or manufacturer friendly and adaptable to real-world conditions and events.

Hence, some conventional apparatuses hitherto have not provided for adequate sample pre-treatment. Biological samples, such as tissue samples, are usually prepared before the staining can be performed and may be subjected to a pre-treatment process depending upon the type of staining process that is to be performed on the tissue. Pre-treatment processes are generally carried out manually in a laboratory and may include deparaffinization or target retrieval. In addition, pre-treatment processes may also require immersion of the slide in a buffer, or in other types of processing liquids for some predetermined amount of time and at a specific temperature. Manual sample preparation may be cumbersome because pre-treatment steps are often subject to stringent constraints and are sensitive to minute variations in experimental conditions. Consequently, small deviations in the pre-treatment protocol may lead to insufficient pre-treatment and inaccurate results.

Thus, there is a need for systems and methods to allow for the automatic real-time continuous processing of biological samples, so that once a carrier containing a sample, such as a slide, has been prepared and introduced into an apparatus, it is processed in accordance with specified protocols, in conformity with any constraints, and, with minimal, or in some cases, with no further user-intervention.

There is also a need for systems that automate the sequencing of sample processing to maximize throughput and that allow users to track and monitor the status of slides in the apparatus. Additionally, on account of the sensitive nature of the process, there is a need to provide feedback to users about processing related errors, or a lack of resources in sufficient time for corrective action to be taken. Moreover, there is a need to collect both slide and apparatus related information and share the collected information so as to improve efficiency and allow automatic interaction with other information processing systems.

At least one of the foregoing needs are met, to a great extent, by at least one embodiment of the disclosed invention, wherein in one aspect the present disclosure relates, in part, to the field of software and hardware for the control, management, tracking, monitoring, scheduling and diagnosing of automatic biological sample processing systems. In some embodiments, systems, methods and apparatus allow for the automatic pre-treatment of the biological samples on slides or other similar carriers or substrates in an automatic staining apparatus so that the entire processing of the biological samples may be performed automatically in a single physical apparatus.

In accordance with one aspect of the present invention, a method of processing a plurality of biological samples in an apparatus is provided that in some embodiments provides applying at least one reagent from a plurality of reagents to at least one first biological sample according to a sequence of steps in a first protocol, wherein at least one second biological sample can be added or removed from the apparatus prior to completion of the first protocol, and wherein at least one second reagent can be added or removed from the apparatus prior to completion of the first protocol.

In accordance with another aspect of the present invention, a method of processing a plurality of biological samples in an apparatus is provided that in some embodiments provides applying at least one reagent from a plurality of reagents to at least one first biological sample according to a sequence of steps in a first protocol. The method may also include, prior to completion of the first protocol, adding a second biological sample to the apparatus and applying at least one reagent from the plurality of reagents to the second biological sample according to a sequence of steps in a second protocol.

In accordance with yet another aspect of the present invention, a method of processing a plurality of biological samples in an apparatus is provided that in some embodiments provides applying at least one reagent from a plurality of reagents to at least one first biological sample according to a sequence of steps in a first protocol and applying at least one reagent from a plurality of reagents to at least one second biological sample according to a sequence of steps in a second protocol. The method may also include determining the first-completed biological sample, being whichever one of the first biological sample and the second biological sample whose processing is completed prior to the completion of the processing of the other biological sample and removing the first-completed sample from the apparatus without interrupting the processing of the other biological sample.

In accordance with yet another aspect of the present invention, an apparatus for automated processing of a plurality of biological samples is provided that in some embodiments provides at least one probe for dispensing at least one reagent, a plurality of reagent containers, and a plurality of biological sample carriers wherein processing of each biological sample is conducted according to a respective sequence of protocol steps, wherein a first biological sample, on a first sample carrier, for which the processing is completed may be removed from the apparatus simultaneous with the processing of a second biological sample on a second carrier, and wherein a first reagent container may be removed or replaced simultaneous with the processing of at least one biological sample.

In accordance with yet another aspect of the present invention, an apparatus for automated processing of a plurality of biological samples is provided that in some embodiments provides a means for dispensing at least one reagent and means for individually supporting a plurality of biological samples wherein processing of each biological sample is conducted according to a respective sequence of protocol steps. The apparatus may also include a means for scheduling the order of protocol steps needed for processing a plurality of biological samples, wherein a first biological sample, on a first sample carrier, for which the processing is completed, may be removed from the apparatus simultaneous with the processing of a second biological sample on a second carrier, wherein a first reagent container may be removed or replaced simultaneous with the processing at least one biological sample.

In accordance with yet another aspect of the present invention, an apparatus for automated processing of a plurality of biological samples is provided that in some embodiments provides at least one probe for dispensing at least one reagent, a plurality of reagent containers, and a plurality of biological sample carriers, wherein processing of each biological sample is conducted according to a respective sequence of protocol steps, wherein a first biological sample, on a first sample carrier, for which the processing is completed, may be removed from the apparatus simultaneous with the processing of a second biological sample on a second carrier, and wherein a first reagent container may be removed or replaced simultaneous with the processing at least one biological sample.

There are, of course, additional embodiments of the invention that will be described below.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The accompanying drawings, which are incorporated in and constitute a part of this specification, illustrate a number of non-limiting embodiments of the invention and together with the description, serve to explain the principles of the invention.

FIG. 1B is a schematic perspective view of a staining apparatus according to one embodiment of the invention;

FIG. 5 is illustrates a staining protocol using a representative chemistry application in accordance with one embodiment of the invention;

FIG. 9 shows an exploded view of the probe of FIG. 8;

DETAILED DESCRIPTION OF THE INVENTION

Figure 1A:
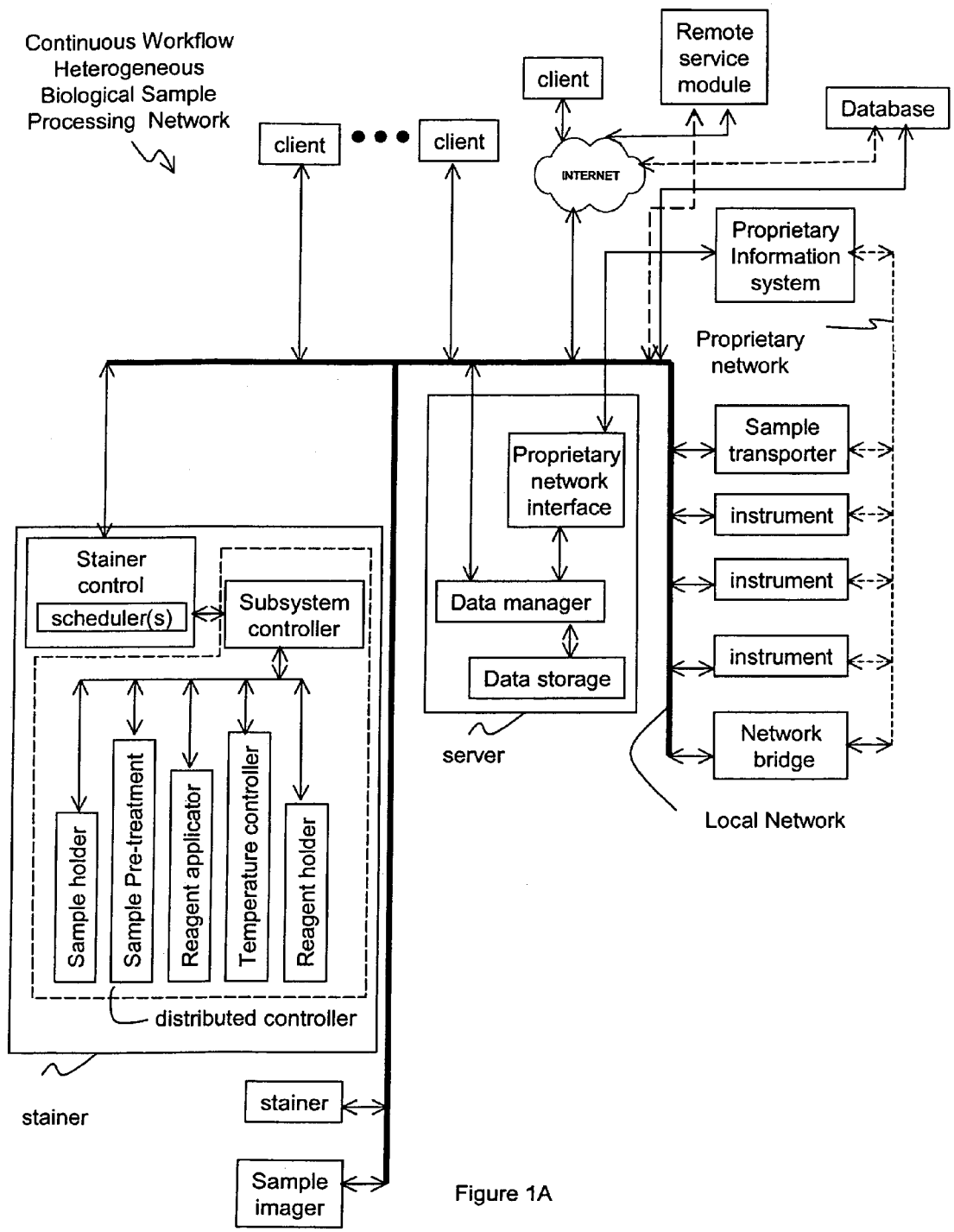
FIG. 1A is an overview of an embodiment of a continuous workflow heterogeneous biological sample processing network.

One embodiments of present invention relates to a system and method for pre-treatment of biological samples. Various modifications to the embodiments will be readily apparent to those skilled in the art and generic principles disclosed herein may be applied to other embodiments. The described examples are exemplary and embodiments should not be construed to limit the present invention to the systems, techniques, and applications explicitly described herein. The present invention is not intended to be limited to the embodiments shown but is to be accorded the widest scope consistent with the principles and features described herein.

The present disclosure relates, in part, to the field of software and hardware for the control, management, tracking, monitoring, scheduling and diagnosing of automatic biological sample processing systems. In some embodiments, systems, methods and apparatus according to the present invention allow for the automatic pre-treatment of the biological samples on slides or other carriers or substrates in an automatic staining apparatus so that the entire processing of the biological samples may be performed automatically in a single physical apparatus. In some embodiments, according to the present invention systems and methods are provided for control, including the monitoring and diagnosis of a stainer apparatus that processes biological samples accommodated on slides. In some embodiments, the biological samples are treated with a predetermined amount of reagent in a sequence according to a protocol, and the apparatus may further provide the capability for pre-treatment prior to staining. In some embodiments, systems and methods according to the present invention, may allow for the co-ordination of the actions of several such automatic staining units.

As used herein, reagent includes any fluid or gas for use in the apparatus such as chemicals, biological fluids, aqueous mixtures, antibodies, biological probes, stains and dyes, markers, chromogens, and fluorophores.

Some embodiments of the invention include a scheduler, in some embodiments referred to as a adaptive sample processing control system, such that one or more groups of samples may be processed according to one or more protocols that may be automatically identified by the scheduler. As used herein tasks refer to steps that are executed according to a protocol. In some embodiments, sample groups or individual slides may be inserted or removed during processing protocol steps by the control and monitoring accomplished by the scheduler. In some embodiments, protocols may be indicated by information on the slides. Some embodiments of the present invention also include a system and method for defining new protocols that may be applied to carriers. Protocols may be defined or adapted at the apparatus or remotely through the internet or a network as, for example, described below. Some embodiments of the invention include a system for the detection of incompatible or inconsistent protocols, and a system and method to prevent the use of incompatible reagents within a protocol or adaptation of protocols in view of mechanical failure such as temperature control failure or fluid failure such as lack of at least one reagent.

In one embodiment, the apparatus may include a means for monitoring and receiving, viewing, inputting, programming, analyzing, and editing data. For example, some embodiments of the invention provide a Graphical User Interface (GUI) to allow user input and control of the apparatus. Other embodiments include an integrated touch screen, remote clients including workstations, PCs, internet, cell phones, PDAs, and pagers, Other embodiments include monitors within network connected or remotely connected instruments. Some embodiments of the invention provide a remote monitoring system that allows remote tracking and monitoring of the apparatus including retrieval of diagnostic information about the apparatus. Some embodiments of the present invention relate to a system and method for tracking reagent usage and system statistics to make predictive determinations with regard to pre-ordering supplies.

Some embodiments of the present invention relate to a system and a method for scheduling the continuous loading and processing the slides within the apparatus so as to: record the introduction of new slides, prevent the spoilage of samples on the slides, maximize the throughput of slides, and, to track and record the sequence of events including the application of reagents and other protocol specific events that pertain to the slide. In some embodiments, the automated sample processing system may allow changes to the system while operating and may automatically adapt to changes in originally scheduled aggregate events. In some embodiments, the system may provide a suggested schedule to permit an operator to optimally enhance throughput of processed slides.

As used herein, automated is defined as a plurality of steps that are executed by substantially mechanical, computer and/or electronic means. It does not exclude some human intervention steps such as loading samples or manually replacing one of the described features or steps.

As used herein, continuous workflow is defined as allowing substantially continuous usage and/or processing of biological samples including the use of reagents. For example, continuous workflow includes high availability of samples or empty sample holders or reagents or empty reagent holders or fluids for addition or removal of at least one of these without substantially interrupting the processing and/or integrity of other samples. For example, a sample being processed or waiting for processing or completed may be available to a user on an ongoing basis without, for example, disrupting the integrity of samples in the apparatus or sample processing protocols. Substantially, as used in this context, refers to not damaging the sample or leading to an invalidated protocol. For example, substantially continuous usage includes the application of a buffer to keep sample integrity while executing other tasks. Another embodiment of continuous workflow is the ability to continue to process at least one sample or keep the integrity of a sample or protocol when the apparatus suffers at least one mechanical, electrical or software malfunction. A further embodiment of continuous workflow is the timely transmission or submission of data to a user or another element of the apparatus or apparatus network that facilitates the integrity of a sample or conformance to a protocol of the processing of a sample.

Some embodiments of the present invention relate to a system and method for the control of fluidic sub-system of the apparatus, wherein different fluids are supplied to baths or chambers in the apparatus within which slides may be processed in accordance with a protocol. Systems and methods according to the present invention provide a means to control the sub-systems to ensure the availability and flushing of the fluids in accordance with the protocol. Some embodiments of the present invention relate to a system for the software simulation of the operation of the sample processing system apparatus. Such a system allows testing, debugging and performance tuning of the sample processing system apparatus, hardware and, software. In one embodiment, the simulation capability may be used in real-time by at least one scheduler to determine the most efficient courses of action or scoring strategies.

In some embodiments of the invention, slide and reagent related information may be read electronically from labels attached to the slide and reagent containers respectively, thus obviating the need for a predetermined placement of reagent containers. In some embodiments of the invention, one type of optical identification element may be optical character recognition or a two-dimensional symbology, such as the so-called "Infoglyph™" type or other identification element such as RF tags. In some embodiments, one or more optical and/or electronic sensors may be used to retrieve slide-related information, including high resolution images of samples on the slides. In some embodiments, these images may be indexed, stored, and retrieved for processing and analysis. In some embodiments, images of the samples may be captured, indexed, and stored at various stages of the processing.

A detailed description of embodiments of the present invention follows, with reference to the accompanying drawings. In the figures, elements with similar functions are prefixed with the same numeric identifier, and individual instances are identified with a hyphenated ordinal suffix.

FIG. 1A is an overview of one embodiment of a continuous workflow heterogeneous biological sample processing network as described herein. In one embodiment, a heterogeneous network is not required. For example, one embodiment of the invention is a continuous workflow biological sample processing apparatus. Not all elements of the embodiment are required to achieve at least one of the advantages described herein. Examples of each of these elements and examples of how they interact and operate are provided herein. For example, the embodiment may be a continuous workflow slide staining system, however it is not limited to a staining apparatus. The stainer may have a plurality of sample holders and/or reagent holders. The stainer may also comprise a distributed controller which may control at least one element chosen from at least one sample holder, at least one sample pre-treatment element, at least one reagent applicator, at least one temperature controller, and at least one reagent holder. A scheduler may schedule tasks. In one embodiment, the scheduler(s) may be non-deterministic and adaptive, i.e. does whatever is next and whatever is next may change for a variety of conditions. In one embodiment, the stainer communicates with a network, such as a heterogeneous network. The network, in one embodiment, comprises a computer that will provide data storage and retrieval, data manager, and data communications. As shown in FIG. 1A, the network may include clients for monitoring & receiving, view, inputting, programming, analyzing, and editing, data to the system and it may also include other instrumentation for further handling, sorting, processing and analysis of samples. The network may also include a LIS interface that provides ability to communicate with proprietary networks. Alternative embodiments and more specific embodiments of such a heterogeneous biological sample processing network are described as follows.

FIG. 1B illustrates an example of a continuous use, i.e. continuous workflow, multiple-sample carrier, high-throughput processing instrument for staining paraffin-embedded and frozen tissue sections, cytospins, cell smears, and fine-needle aspirates. The staining apparatus 1 is just one embodiment that may automate slide preparation, including deparaffinization and target retrieval, as well as routine tissue staining methods used, for example, in immunohistochemistry, immunocytochemistry, in-situ hybridization and special stains. In one embodiment, the staining apparatus 1 may accommodate both ready-to-use and user-defined reagents and protocols. Thus, slides can be added, removed, and/or processed on an ongoing basis without disrupting the integrity of slides already in process.

A sample holder is any medium that supports a sample. As used herein sample holder includes any support, such as a carrier, test tube, chip, array, disk, or slide, that can support at least one sample. Sample holder also includes a support for a group of supports such as a rack supporting a group of slides. Sample holder may further refer to a larger scale support, such as a slide rack holder that holds at least one smaller support, such as a plurality of slide racks, each rack containing a plurality of slides. A holder may releasable hold, securely hold, and/or hold in such a way that permits movement, such as vertical, horizontal or pivoting about one or more axis. In one embodiment, the sample holder may function as a sample holding means. Alternative embodiments of a sample holder comprise one or more carousels, trays, racks, carriers, holders, compartments, or other conveyance arrangements used for the handling and processing of samples and sample carriers any of which may be at least partially removable.

Figure 2:
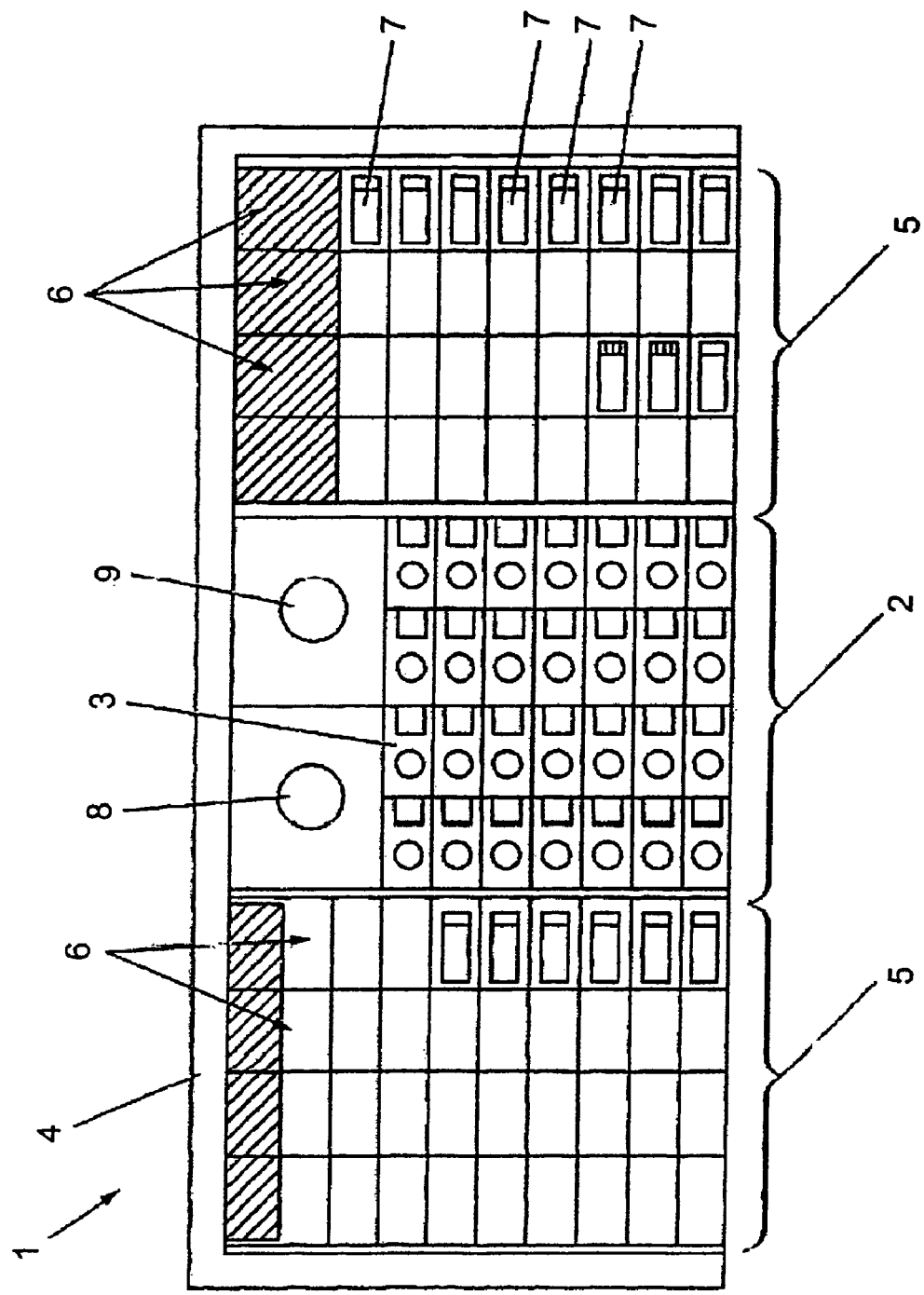
FIG. 2 is a plan view of the work area in the staining apparatus shown in FIG. 1B.

An embodiment of a staining apparatus 1 according to the invention is shown in FIGS. 1B and 2. The apparatus, for example a staining apparatus, may comprise a means for holding at least one sample, such as a slide, and a means for holding a group of samples or sample holding means, such as a group of slides or slide holders. For example, the staining apparatus 1 may comprise a frame 4 surrounding a reagent station 2 comprising an array of reagent bottle compartments wherein each compartment a reagent container 3, such as a bottle or vial, is placed, and a first and second slide sections 5 wherein a number of separate rack assemblies 6, i.e. sample carrier holders are placed, and where each rack assembly 6 accommodates a number of sample carriers 7, such as, for example, microscope slides mounted side by side in the rack assembly 6. In one embodiment, the rack assembly 6 may incorporate a slidable design feature such that the rack assembly 6 may be slidably disposed within a position of the staining apparatus 1. In the embodiment shown, each rack assembly 6 may hold up to eight sample carriers 7, but the rack assembly 6 may be designed to hold any suitable number of sample carriers 7. With eight rack assemblies 6 arranged side by side, the shown embodiments may hold up to sixty-four sample carriers 7 each having a sample, e.g. a tissue mounted on the upper side of the slide, so that reagent may be applied from above to the sample on each sample carriers 7.

A reagent holder is any medium that supports a reagent. For example, as used herein, a reagent holder includes a container, such as a bottle or vial, that can hold at least one reagent. It also includes a support for at least one container, such as a container rack. Reagent holder may further refer to a larger scale support, such as a rack holder, that holds at least one smaller support, such as a plurality of racks, each rack containing a plurality of containers. A holder may releasable hold, securely hold, and/or hold in such a way that permits movement, such as vertical, horizontal or pivoting about one or more axis. In one embodiment, the reagent holder may function as a reagent holding means. Alternative embodiments of a reagent holder comprise one or more carousels, trays, racks, carriers, holders, compartments, or other conveyance arrangements used for the handling and processing of reagents and reagent carriers any of which may be at least partially removable.

The apparatus, for example a staining apparatus, may comprise a means for holding at least one reagent, and a means for holding a group of reagents or reagent holding means, such as a group of reagents or a plurality of reagent holders. In certain embodiments, as illustrated in FIGS. 1B and 2, the reagent station 2 can be located generally at the middle of the staining apparatus 1. Alternatively, in certain embodiments, the reagent station 2 can be located at one or both ends of the staining apparatus 1, the first or second slide sections 5 can be located generally at the middle of the staining apparatus 1. In one embodiment, a sample holder or group of sample holders is independently accessible from other sample holders or groups of sample holders. Similarly, in a further embodiment, a reagent holder or group of reagent holders is independently accessible from other reagent holders or groups of reagent holders.

Independently accessible as used herein refers to, for example, an element, that is at least partially removable from the apparatus, for example, inserting or removing manually or via mechanical means. Independently accessible as used herein may further refer to an element that is accessible through at least one opening, for example, such as a slot, hole, aperture, gap, or outlet.

The apparatus, for example a staining apparatus, may comprise a means for providing at least one reagent to samples, which may include, for example, a means for delivering a reagent, such as a probe or syringe, a means for delivering fluids to, for example, a probe, such as the fluidics embodiment described herein, a means for mixing reagents prior to and following delivery to a sample, such as the mixer described herein and means positioning the sample such as bringing a probe to the sample using, for example, a robot, or moving the slide to the probe, for example on a carrousel. The apparatus may also include a means for preventing contamination or carryover of reagents or samples such as for example a wash station, an aspirator and/or air flow such as pressurized gas.

As used herein a probe refers to an apparatus to transfer, move, or apply a fluid or gas such as to a sample or container. Examples include, but are not limited to a syringe, pump, aspirator, injector, extractor and an air knife or nozzle. In one embodiment, the probe may function as means for dispensing at least one reagent. A probe may also include a sensor, detector and/or level sensor, including for example a camera or other means for detecting the presence of a sample, determining the level of a fluid in a reagent container or sample, taking a picture of a sample and/or reading information regarding a sample as further described herein. In one embodiment, a detector may refer to a sensor, measurer, camera, CCD, and/or RF-ID transponder. In one embodiment, the detector may function as a means for detection.

As used herein a mixer is an apparatus for combining, separating, agitating, diluting concentrating, mixing. Mixer may include mixing in a separate container or on a sample or sample holder or reagent holder. In one embodiment, the mixer may function as a means for mixing.

As used herein, fluid supply refers to fluid containers, such as bottles, and conduits for transporting the fluids, such as tubing, pumps, valves, and flanges. In one embodiment, the fluid supply may function as a means for delivering fluid.

A robot arm 20 for moving a probe 10 in X and Y (as well as Z) direction as indicated by the arrows X and Y may be arranged above the frame 4 of the staining apparatus. The robot arm 20 may therefore position the probe 10 above all reagent containers 3 as well as above all the sample carriers 7, and may further operate the probe 10 to aspirate portions of reagent contained in any of the bottles 3, to transfer the portion of reagent and apply it to any of the sample carriers 7 in order to provide a selected staining or treatment of the sample on each sample carriers 7. Probe 10 may also dispense and aspirate reagents in mixer 9A and be cleaned in wash station 8 as will be further discussed below. By use of suitable control means e.g. a computer (not shown) having the appropriate software and input data for the purpose, this staining apparatus 1 is able to automatically stain or treat samples requiring different staining or treatment reagents and processes.

Thus, in some embodiments, the staining apparatus 1 may allow individual sample carriers 7 to undergo processes such as deparaffinization and/or target retrieval. These procedures may be performed in compartments of the staining apparatus 1 such as within processing tanks 101 but neither, either or both may be done on an individual sample carrier 7 basis. Additionally, reagents may be loaded and/or unloaded (for example, upon sample carriers 7) on an ongoing basis i.e., without disrupting the integrity of the sample carriers 7 already processing. This concept of continuous work flow for processing sample carriers 7 may also include continuously updating the onboard reagent inventory of the staining apparatus 1.

Figure 7A:
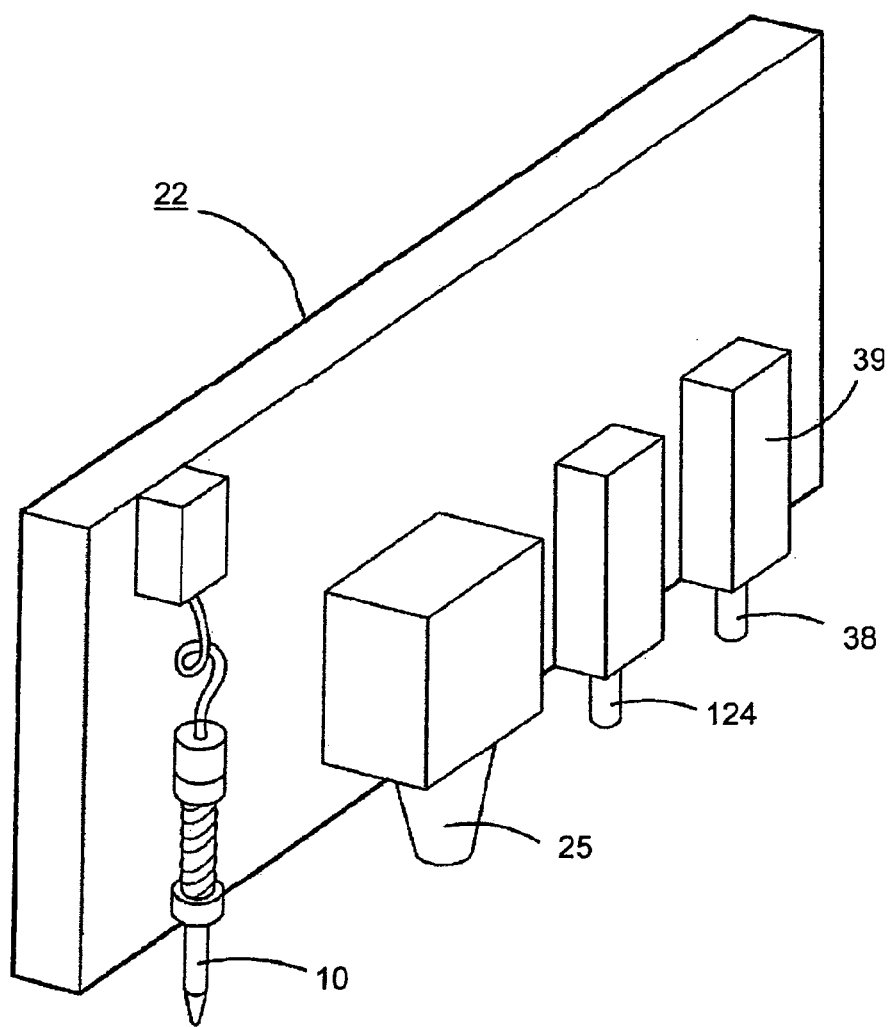
FIG. 7A shows a schematic view, in accordance with one embodiment of the invention, of a robotic head with a probe mounted thereon.

As shown in FIG. 1B and, in more detail in FIG. 7A, the probe 10 may be accommodated in a robotic head 22 and may be manipulated by the robot arm 20. In the embodiment, shown, the probe 10 is raised to an upper position (in a Z direction) where it is clear of the reagent containers 3 underneath the probe 10, but the robot comprises means in the robotic head 22 for lowering the probe 10 in order to processing the probe tip into the content of a selected reagent container 3 or mixer 9A and to aspirate a selected amount of reagent for the selected staining or treatment process. The robotic head 22 may be provided with an optical sensor 25 such as a CCD camera pointing downwards. The camera may be utilized to determine status information and/or presence of the slides and/or the reagent bottles and other features of the apparatus in the work area, for example reading a code provided on a reagent container to determine the reagent type and the reagent location within the system. The camera may also determine status of the tissue sample carriers 7, for example the location of a particular sample carriers 7, informational indicia, such as a code, that indicate information about the tissue sample presented on the sample carriers 7 or the processing protocol to be performed. The camera may also determine the presence or absence of sample carriers 7 and/or reagent containers 3 that have, for example, invalid or missing labels or codes. In some embodiments, the camera may capture high resolution pictures of a sample, such as a slide for subsequent analysis, for example, by a pathologist. Such pictures may even be transferred over a network system such as described herein. The camera may have a fixed focal length or adjustable focal length to focus on a sample at different levels and depths. The camera may be controlled remotely or automatically by the instrument, for example, using software. Examples of network connections with the stainer apparatus 1 will be explained below. Additional embodiments of the robot or camera head functionality may include transponders providing, for example, an ability to read or write Radio Frequency (RF) tags such as those which may be displaced upon sample carriers 7.

In one embodiment, the robot comprises means (e.g., a rack and pinion or a hydraulic piston) in the robotic head 22 for lowering the probe 10 in order to insert the probe tip into the content of a selected reagent container 3 and to aspirate a selected amount of reagent for the selected staining or treatment process. As schematically illustrated in FIG. 7A, the robotic head 22 may also be provided with an air nozzle 124 for blowing air onto the slide in order dry the slide or to blow away liquid. The robotic head 22 may also include a variety of other components, including, but not limited to a push tool 38, for actuating slide rotation, that may be connected to an air cylinder 39.

Figure 3:
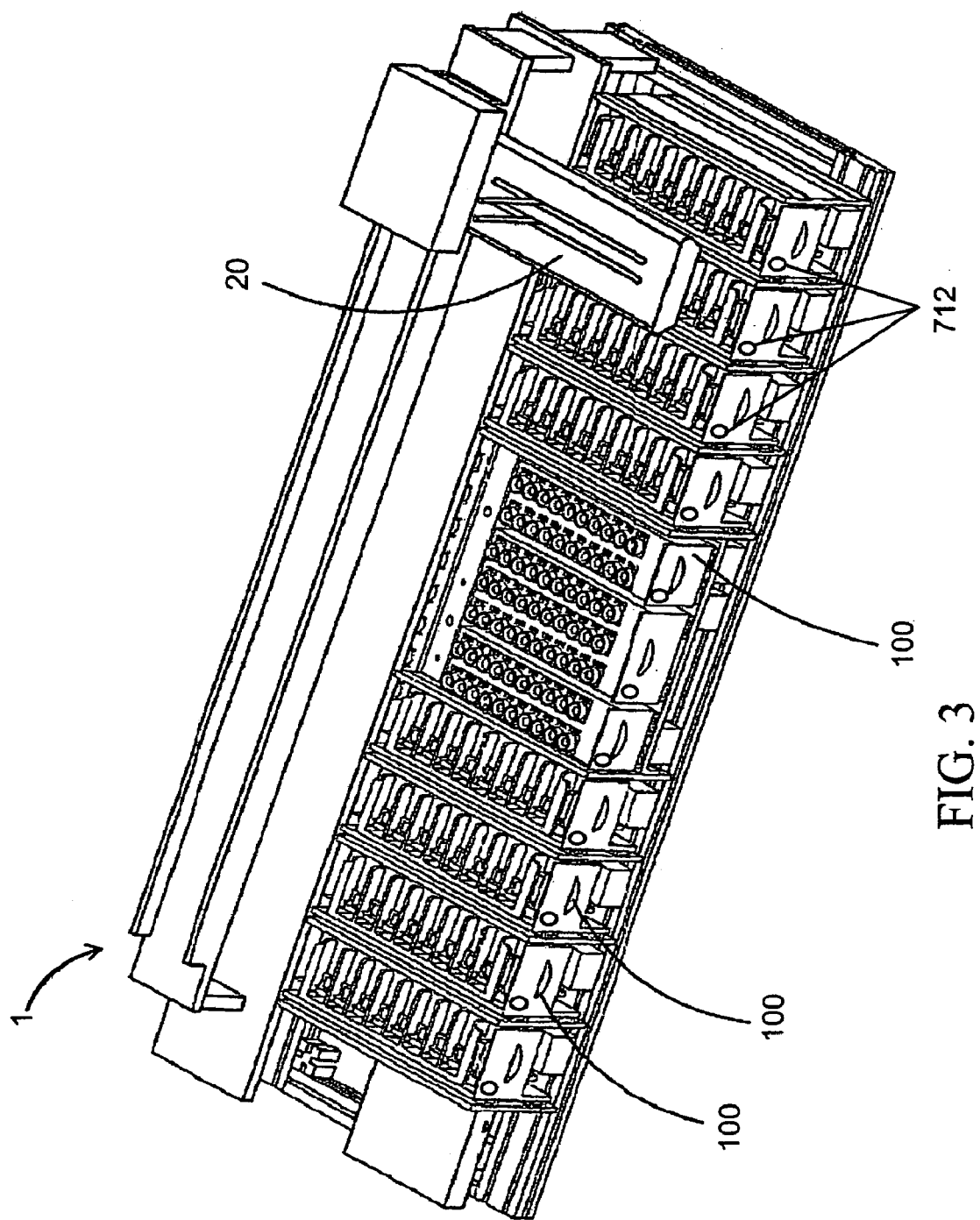
FIG. 3 is a perspective view of the work area in the staining apparatus shown in FIG. 1B showing a collection of samples with a collection of reagents according to the invention.

As illustrated in FIG. 3, the sample processing system may comprise a plurality of drawers or other sample carrier 100 used for the handling and processing of samples and sample carriers 7. Each drawer may be configured to accommodate a slide rack assembly 6 or other sample carrier retainer assemblies, such as slide retainer assemblies, modules, or magazines. Alternative embodiments may include sample processing systems comprising one or more carousels, trays, racks, carriers, holders, compartments, or other conveyance arrangements used for the handling and processing of samples and sample carriers any of which may be at least partially removable. Drawer, as used herein, would include any of these embodiments. Thus, at least one drawer may be configured to accommodate a slide rack assembly 6 or other sample carrier retainer assemblies, such as slide retainer assemblies, modules, or magazines.

Indicator elements 712 may be provided upon or within the drawers (FIG. 3) to indicate a status and accessibility of the drawers and the sample carriers or materials within each drawer for an operator of the system. In one embodiment, visual indicators, such as light emitting diodes, may be used to indicate if a drawer is available, and perhaps unlocked, during operation of the sample processing system, and may indicate conditions such as a locked or open condition of a corresponding drawer, carrier capacity status of the drawer or of a carrier retainment assembly within the drawer, and chemical inventory status of the sample processing system, such as reagent loading status or capacity. A warning indication may be given by these or other indicator elements, as well as other indicative signals. One or a plurality of sensors may be utilized to determine the status of the drawer as indicated by the indicator elements 712 and to further provide processing status as further described below. Additional embodiments may include the use of status indicators and audible features such as aural alarms to facilitate operation of the system. Thus the system may provide at least one substance in a lockable reagent retainment assembly.

Figure 24:
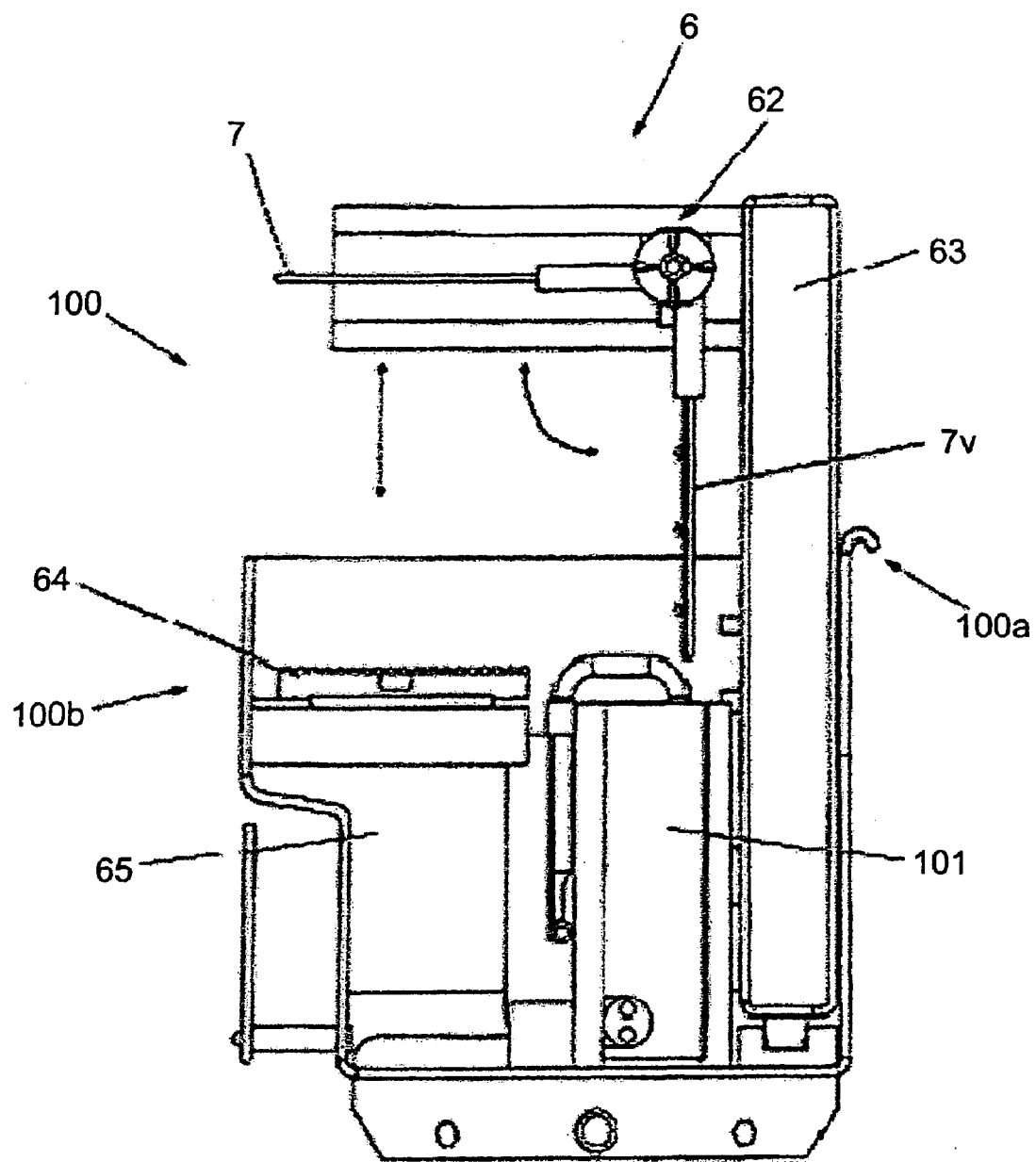
FIG. 24 is a schematic front view of an example drawer assembly including an example slide rack assembly and an example processing tank in an apparatus according to one embodiment of the invention.
Figure 27:
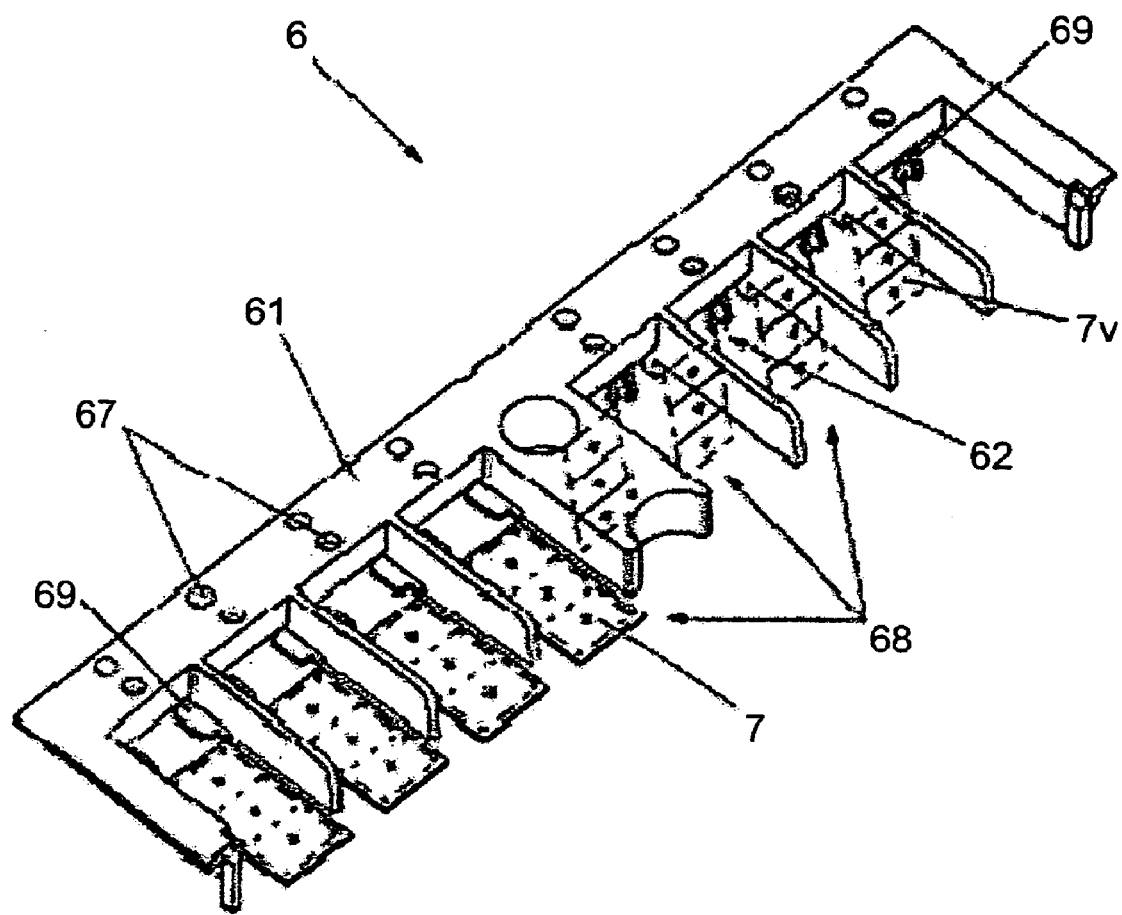
FIG. 27 is a perspective top view of an example slide rack according to an embodiment of the invention.

In some embodiments, sample carriers 7, such as slides are configurable in both vertical and horizontal positions as required for the pre-treatment and staining process, as shown in FIGS. 24 and 27. Other components in these figures will be described in detail subsequently. The ability to provide vertically-oriented sample carriers 7v (FIGS. 24 and 27) in addition to horizontal sample carriers 7 is one embodiment allowing for the automation of the pre-treatment and staining of slides in various manners, including pre-treatment and staining as accepted in conventional manual laboratory methods. The slides 7 are initially loaded into the carrier retention assemblies, such as slide racks, and drawers in the horizontal position. The slides may be horizontally supported by adjustable slide supports (shown in FIG. 28). If pre-treatment is required, such as deparaffinization, the system may, for example, rotate the slide into the vertical position and lower these samples into a processing tank 101, further described below, filled with the required fluids. The apparatus, for example a staining apparatus, may comprise a means for providing bulk fluids to at least one processing tank. Examples are provided herein. In some embodiments, the slide rack 6 is lowered to affect lowering of the slides (see FIG. 24 and FIG. 28). To perform the staining process on the slides, as described below, the system may rotate the slide to the horizontal position and a probe 10 applies one or more fluids, such as reagents, to the sample. Each slide can be rotated independently allowing for the independent processing of different samples with different requirements.

Figure 4:
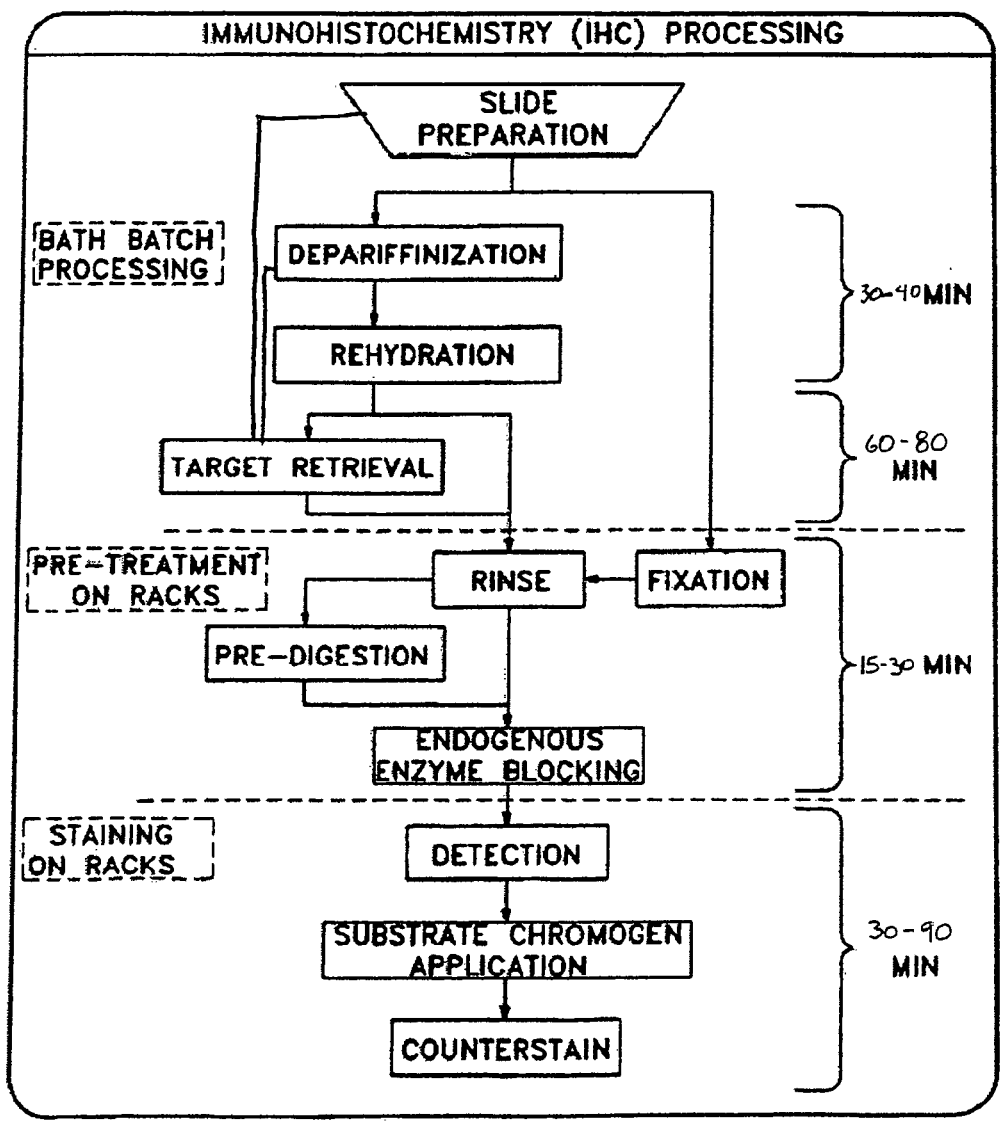
FIG. 4 is a flow chart of some representative process steps of an example in accordance with the invention.

The sample processing system may automate processing steps of samples such as histological tissue sections or cell preparations presented on slides by pre-treatment processing, such as deparaffinization. In one embodiment, the system provides onboard pre-treatment of the slides. The processing of samples may be accomplished according to some embodiments as shown in FIG. 4 and FIG. 5 consistent with features of the present invention. Variants of these protocols and processing steps, or other processing steps, may be accomplished consistent with the present invention.

Examples of two types of pre-treatment that are usually performed are—but not limited to—deparaffinization and target retrieval. In some embodiments, these processes may be performed with the slides in a vertical orientation, immersed in processing tanks of various fluids. Deparaffinization involves immersing the slides into processing tanks where a series of fluids may be sequentially introduced and removed for predetermined periods of time (potentially for about 5 or 10 minutes). The process is intended to first remove from the sample the paraffin in which it was mounted or otherwise presented, remove the paraffin solvent, and then slowly rehydrate the sample. Target retrieval, and in some embodiments epitope unmasking, may involve immersing the slides in a processing tank of heated buffer, and in some embodiments, immersing for about 20 minutes, and possibly up to 60 minutes, and then cooling, or allowing the slides to cool, for about 20 minutes or less depending on the protocol. Temperature, in some embodiments, is maintained at about 95° C. In target retrieval, a marker or other identifier is used to mark a sample portion of interest, such as a cell or structure thereof.

Figure 25:
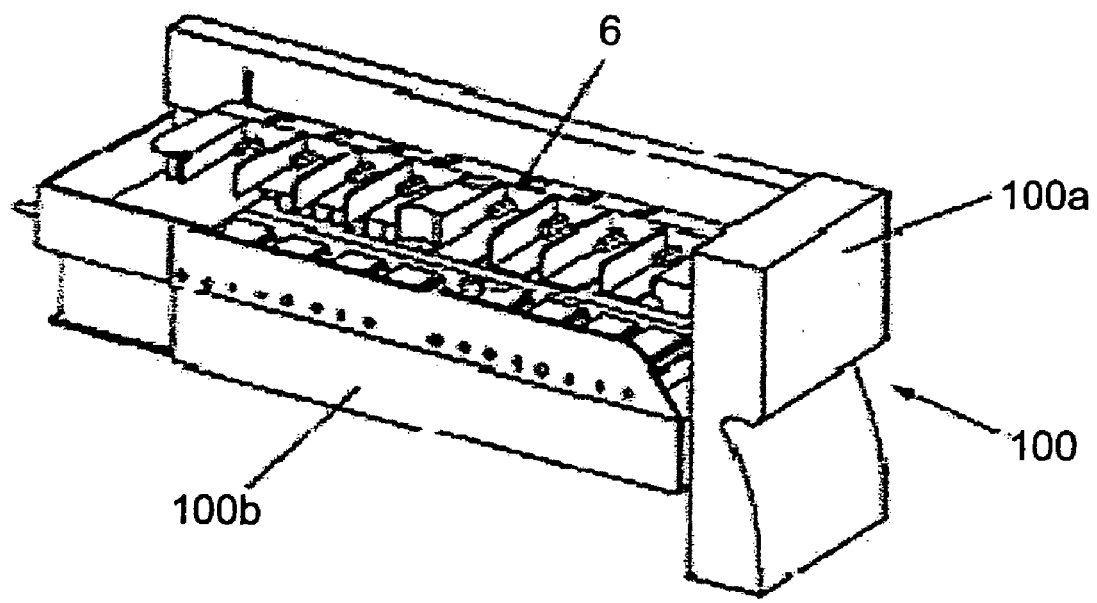
FIG. 25 is a perspective view of an example drawer assembly in a closed position.
Figure 26:
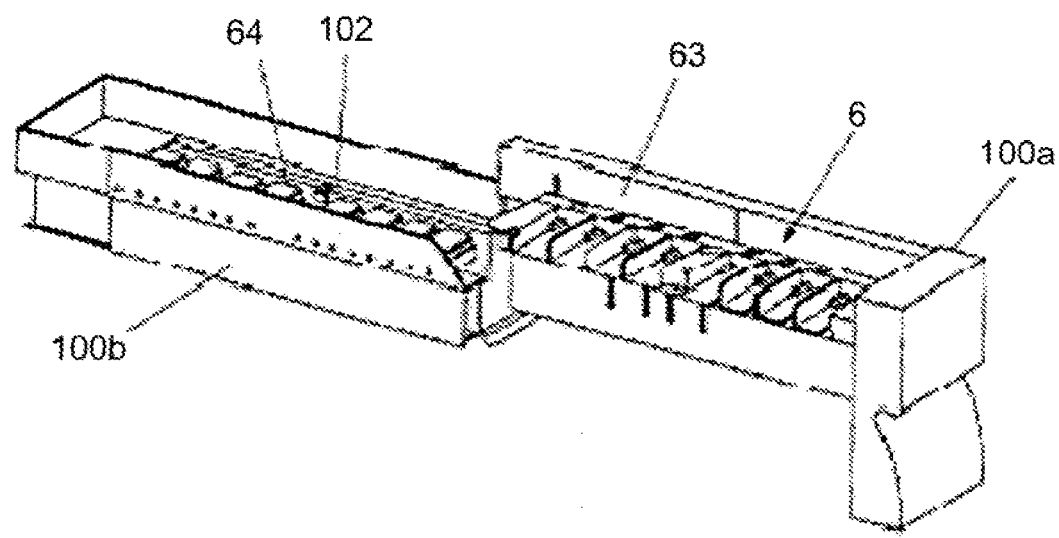
FIG. 26 is the drawer assembly of FIG. 25 in an open position.
Figure 28:
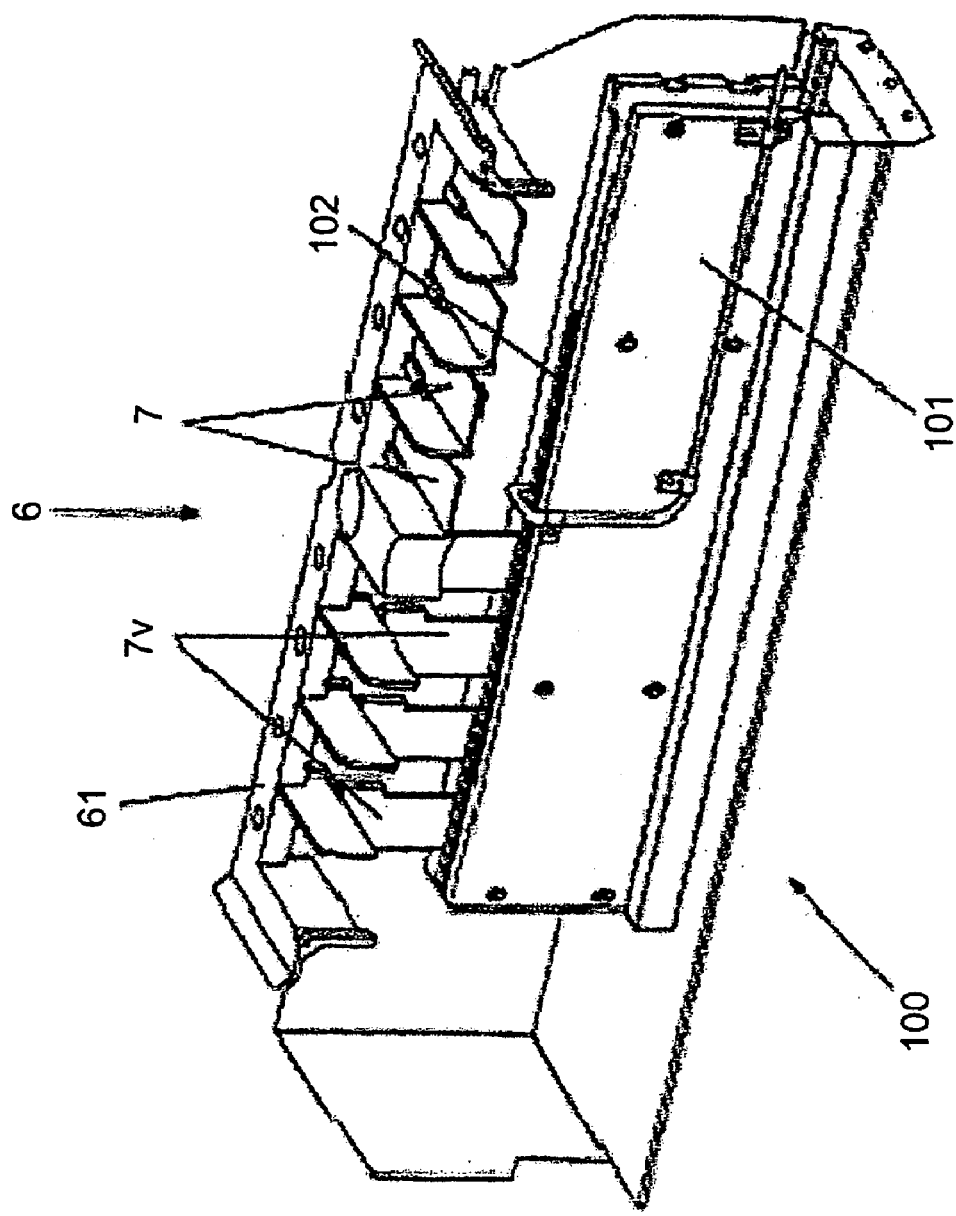
FIG. 28 is a detailed view of an example slide rack holder and one embodiment of the processing tank arranged in a drawer assembly.
Figure 29:
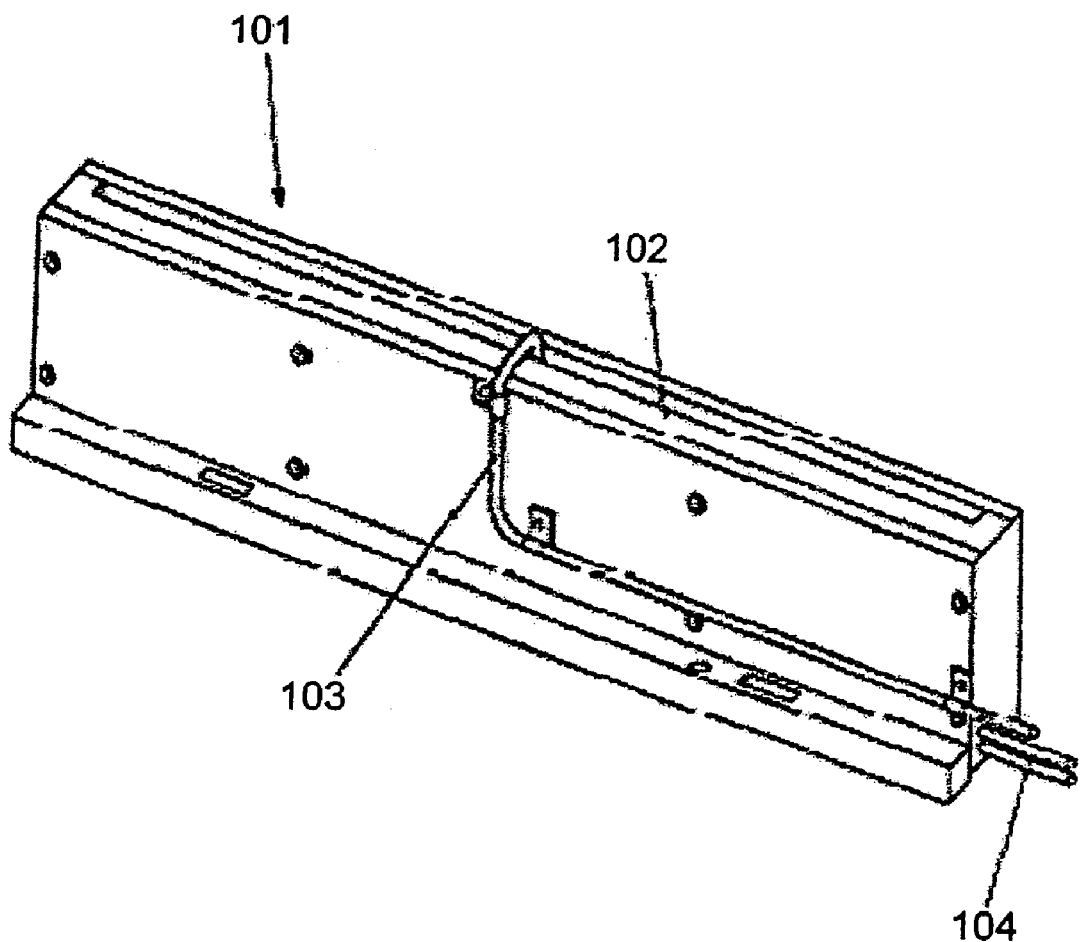
FIG. 29 is a perspective view of a processing tank according to an embodiment of the invention.

In one embodiment, the system automates, and in some embodiments mimics or otherwise corresponds to the procedure and physical attributes of the supplies used manually to perform these same pre-treatment processes. Accordingly, a processing tank 101 may be provided (as shown in FIGS. 24, 28 and 29). In some embodiments, components of each processing tank 101, as shown in FIGS. 25 and 26 are configured within a drawer 100. Other components in these figures will be described in detail subsequently. In some embodiments, the fluids volume needed to perform pre-treatment processes are maintained but instead of the slide orientation with each other being face-to-face, as in conventional systems, they are side-to-side, although other slide configurations are possible. The processing tanks provide even distribution of fluids across the face of the slide.

In some embodiments, the processing tanks 101 have processing fluid which may be utilized to heat the sample carriers 7 therein. Some embodiments provide for target retrieval or antigen retrieval fluids within the processing tanks 101 to be set to different temperatures in individual processing tanks 101. For example, heat may be applied evenly across the face of each individual sample carrier 7 by a thermal device. The precision and physical application of the heat can result in standardization and repeatability of process steps. In some embodiments, individual sample carriers 7 may be processed at different temperatures. Filling and heating tasks may be performed by a computer controlled scheduler, such as an adaptive scheduler, as further described below. Fluid volume may be adjusted to account for the presence or absence of any number of sample carriers 7 and fluid evaporation during thermal processing.

Figure 6:
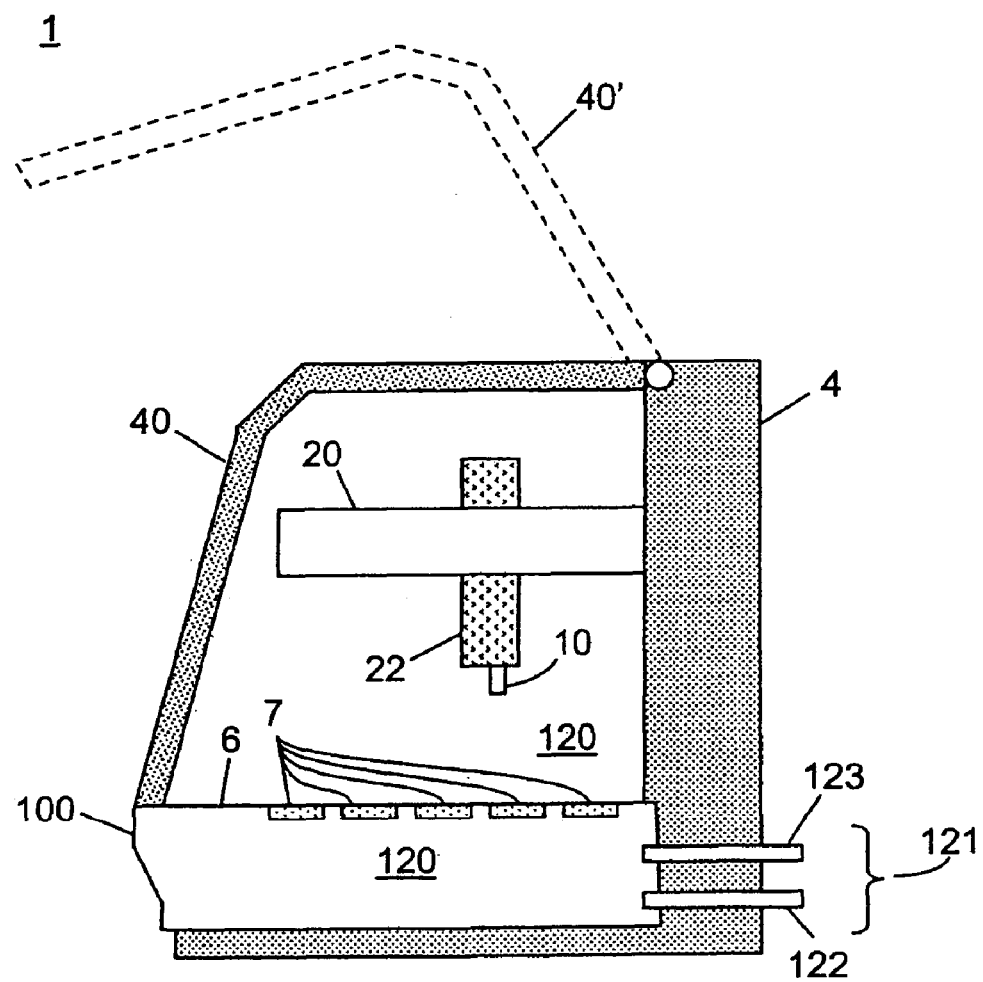
FIG. 6 is a schematic side view of the staining apparatus of FIG. 1B.

As shown in FIG. 6, the apparatus 1 is provided with an openable hood cover 40, which is pivotably attached to the frame housing 4. The hood 40 is shown in a closed position and an open position 40' (the latter of which is indicated in dotted lines in FIG. 6). In the bottom of the frame housing 4, the slide rack assemblies 6, potentially in some embodiments in one or more drawer assemblies 100 are provided. An interior space 120 is defined by this hood cover 40 and the frame 4.

In one embodiment, a climate control device 121 may be provided for controlling the pressure and potentially also the temperature and the humidity of the air in the interior space 120 such as shown inside the apparatus 1. This climate control 121 may include an outlet 122 and an inlet 123 allowing for an exchange of air in a controlled manner. Exhausted air from the interior space may be directed to a collection storage or disposed of in other manners depending on the requirements on the location of the apparatus. The exhausted air may—in particular in some staining or other processes—include volatile fumes or other toxic or unwanted fumes from the reagents and other liquids used for the processing of the biological samples.

For example, the ambient air in the interior space 120 may be drawn through the rack assembly 6 of the drawer assembly 100 in the slide sections 5. By drawing the fumes out of the interior space 120 at a location close to the heating sources and below the level in which the slides are arranged, the fumes are substantially prevented from diffusing too widely in the interior space, whereby the risk of such fumes coming into unwanted contact with biological samples, other reagents or processing liquids may be avoided.

In one embodiment, the temperature, humidity, airflow rate and/or other environmental factors can be controlled by a feedback mechanism from a sensor device, such as one or more sensors arranged in the hood or elsewhere inside the interior space and/or external sensors, which may be advantageous in order to compensate for external influences such as high temperature or extremely dry climate in local areas having extreme climate variations. Software protocols may be utilized by the staining apparatus 1 to record and/or monitor the interior temperature and humidity to ensure conformance with process specifications and tolerances.

Also, it should be understood, that the air drawn into the interior space in addition to being temperature controlled by heating or cooling, also may be humidity-controlled by spraying water droplets or using a filter device, or added other components, like nitrogen gas, carbon dioxide or inert gasses to control the environment in the hood.

In one embodiment, the inlet air is drawn through a humid filter device to ensure high and uniform humidity in the chamber. In another embodiment, the humidity is controlled by spraying water droplets or having a water surface. In yet another embodiment, recycled air is drawn through filters to remove fumes and filters to adjust the humidity. In yet another embodiment, the humidity is controlled to remain substantially above a predetermined level, to prevent drying out of the sample. Also, disinfectants, UV protectants or other compounds could be added to the inlet air to prevent microbial growth or discoloring.

Figure 8:
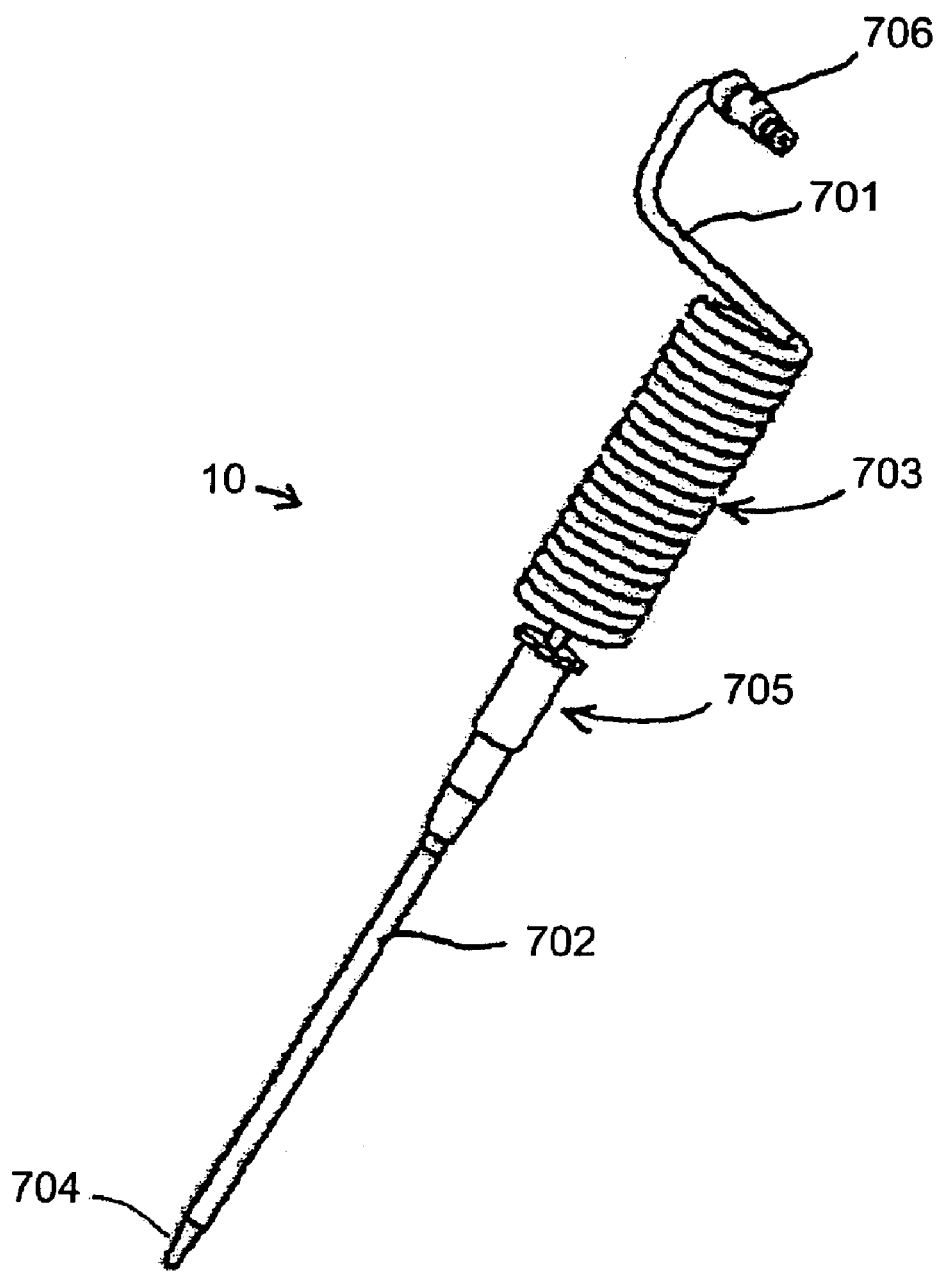
FIG. 8 is a perspective view of a probe according to an embodiment of the invention.
Figure 10:
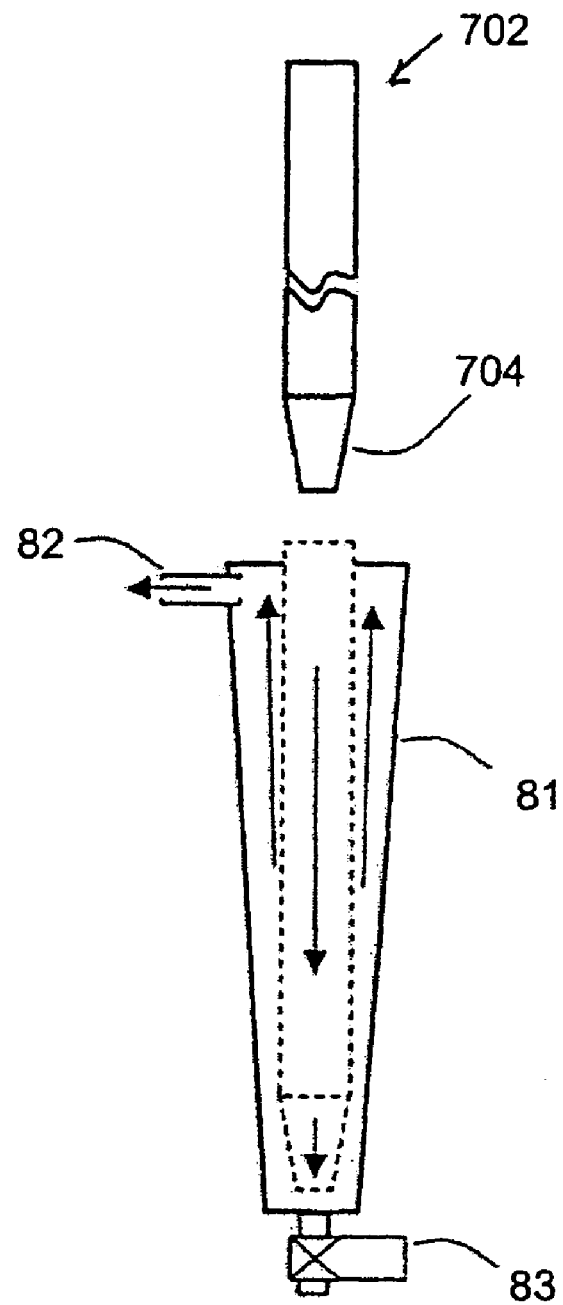
FIG. 10 shows an embodiment of a washing station.

One embodiment of a probe 10 is shown in detail in FIGS. 8 and 9. The probe 10 comprises a continuous tubing 701 having a spiral section 703, a probe member 702 having dispensing end also called probe tip 704, and a mounting end having a fitting 705 for mounting on the robot head 22. For example, the probe member 702 is a rigid tube, which may be made from a metal, such as a 300-series stainless steel, coated with a fluoropolymer, e.g. Teflon™. In one embodiment, also the inner tubing is a fluoropolymer, such as Teflon™. The materials for the probe should be able to withstand the fluids to which it will be exposed during the sample processing. Such fluids may include aqueous, alcoholic, acidic, basic, organic solvent liquids and combinations thereof.

In one embodiment, the dispensing end, or probe tip 704 (FIGS. 8-9) may be a cone. In one embodiment, the tubing 701 is arranged as an inner lining of the probe member 702 covering the total inner surface of the probe member 702. The other end of tubing 701 ends in a fitting 706 for connection to a computer controlled pneumatic system, able to provide any desired pressure, enabling the probe to aspirate, with-hold, or dispense predetermined amounts of a fluid. The rigid probe member 702 is mounted with fitting 705 in a holder 205 (see FIGS. 7B-7C) on the robotic head 22.

In one embodiment, the holder 205 is mounted in a rack and pinion drive and may be moved in a vertical direction raising or lowering the probe relative to the underlying samples.

The spirally wound section 703 of the probe 10 may comprise at least one winding and, for example, a plurality of windings that may flex as the probe 10 is moved up or down or in any other direction by the robotic head 22. Additionally, this section of tubing in the spirally wound section 703 may provide for a considerably increased internal volume in the tube, so that the probe may hold a relatively large fluid content.

EXAMPLE

In one embodiment, the inner diameter of the tubing 701 is about 1.5 mm. In one embodiment, the probe aspirates a volume of about 2.5 ml with a corresponding length of the tubing 701 that is about 1.5 m. Such length may be accommodated/achieved by including a coil section having about 20 windings and a diameter of about 20 mm providing for about 1260 mm. By adding thereto the length of the rigid probe member and the tubing section from the coil to the fitting 706, a total of 1.5 m of tubing may be obtained. Obviously, the tubing 701 may be designed to accommodate other fluid volumes. The inner diameter of the tubing is determined such that the viscosity of the fluid will secure the fluid in the probe during the movement of the probe from reagent container to a mixer and/or a slide.

In one embodiment, the robotic head is adapted to lower the probe 10 when it is aligned on top of a selected reagent container. In an embodiment, a reagent container 3 is covered by a cover through which the probe tip 704 may penetrate when so forced by the robotic head. The probe 10 being capable of automatically gaining entry into the container, allows for a "closed" container design, i.e. a reagent container that constantly through all lifetime of use is provided with a protecting cover or septum.

After having pierced the cover or septum covering a reagent container 3, a predetermined amount of the fluid in the container is aspirated into the tubing 701, and the probe 10 is raised. After having aspirated a predetermined volume of fluid into the probe, it may be advantageous to aspirate some air in order to reduce risk of losing a drop of reagent during the robotic transfer of the probe including the fluid to the staining section accommodating the slide for which the reagent is intended. The robotic head moves the probe until it is located directly above the slide, and the probe may be lowered until it is located a predetermined distance above the slide. Reagent may be dispensed, such as via syringe pump, to dispense a predetermined volume of reagent to the tissue on the slide.

In some embodiments, with the probe raised above a reagent container, an air gap may be created by aspirating air and the probe may be lowered into the reagent container again aspirating a second volume of the same reagent, raised again repeating the aspiration of air and reagent a plurality of times (typically 5-10 times). After having aspirated a plurality of predetermined volumes of reagent for a plurality of predetermined slides, the robotic head moves the probe including fluid and air to the staining section accommodating the slides for which the reagent is intended. This procedure may be very timesaving as the probe is only moved once from the reagent section towards the slide section. It is useful if the same reagent has to be dispensed onto a plurality of slides.

In a further alternative procedure, and, after having aspirated a first fluid and a first air gap into the probe, a second fluid may be aspirated into the probe tubing from another reagent container and a second air gap and so on until reagents for a plurality of slides have been aspirated. In some embodiments, greater than 50% of the length of the tubing 701 away from the probe tip 704 may be filled with an inert or filler fluid such as distilled or DI water while the fluid or reagent that is to be applied to a sample occupies only the portion adjacent to the probe tip, with an air gap or bubble between the inert or filler fluid and the fluid that is to be applied to the sample. This permits minimization of the amount of aspirated reagent, which may be advantageous for conservation of reagents that are expensive or short supply, while still permitting precise control of the dispensed volume. Thus, in some method embodiments, a volume of inert or filler fluid is first aspirated into more than 50% of the tubing; a quantity of air is subsequently aspirated, and, subsequently, a reagent or fluid to be administered to a sample is aspirated into the tubing. The reagent (or other fluid) may then be administered to the sample in a small proportion without sacrificing precision of the dispensing.

In some embodiments, the pneumatic system may be designed to control the pressure in the probe tube, providing, for example, a vacuum or a pressure below or above the atmospheric pressure according to control signals, for example, generated by a computer, and, for example, according to protocols established for the treatment of the slides inserted into the staining apparatus 1. By having a so-called "active" vacuum in the tubing of the probe according to the invention, the design of the reagent containers is important for ensuring that a predetermined amount of reagent is transferred from the container.

With the probe according to some embodiments of the invention, it is possible to provide both precision and accuracy of the aspirated volumes of reagents. This may be desired as the staining result may be deteriorated if the applied volumes differ from the recommended sizes, and this could later cause difficulties when analyzing the stained sample in a microscope and might give reason to a faulty diagnosis.

In one embodiment, whenever needed—and typically when a different reagent is to be aspirated and dispensed—the robot system may move the probe to a washing station 8 (FIG. 1, FIG. 2, FIG. 10, FIG. 14A) that is able to clean the probe 10, thereby removing all traces of the preceding reagent from the probe.

In one embodiment, the washing station 8 (FIG. 10) comprises deep receptacle 81 able to accommodate a length of the rigid probe member 702 at least corresponding to the length which may have been inserted into a reagent. Through valves (not shown), the tubing end with fitting 706 may be connected to a source of at least one wash solution or cleaning fluid, which will pass through the tubing 701 and finally be ejected from the probe tip into the washing receptacle 81. Further, the wash solution or cleaning fluid passes on along the outer surface of the probe 702 and exits the receptacle 81 through an outlet 82 to waste arranged a distance above the bottom and such as close to the top of the receptacle 81. The receptacle 81 may be emptied by opening a normally-closed bottom valve 83.

In order to dry the probe after the wash, thereby removing any traces of the cleaning fluids, a stream of air may be directed through the probe by connecting the tubing end with the fitting 706 through a valve to an air source.

In an embodiment, the reagent containers or bottles 3 are designed to fit into the reagent section of the sample processing apparatus, and to cooperate with the design of the probe.

In one embodiment, the reagent section comprises a plurality of receptacles able to receive a plurality of reagent containers. For example, a cross-section of these receptacles corresponds to a cross-section of the reagent container. Further, the cross-section may include a non-symmetrical polygon. In an embodiment, shown in several of the FIGS. 11A-11D, the cross-section is a pentagon, and more specifically a pentagon having two sides, and three angles in common with a rectangle. In other words, a rectangular cross-section may be a rectangle with one corner-section replaced by a slanted/oblique fifth side.

In one embodiment, the advantage of such a cross-section is that the containers can only be arranged in the receptacles with a specific orientation. Also, any other container of different design cannot fit into the receptacle. This may help to avoid problems with faulty supply of reagents. An alternative description of the container shape is that the containers are keyed.

This keying or mating of a container to a receptacle may include the top of the container (shown in FIG. 11A), in an embodiment, comprising two features: 1) a neck 137 with a cover providing access to the fluid content, and 2) an identification 138 relating to the content of the container, for example, including information specific to the content, such as, e.g., name of chemical substance, date of delivery, date of expiration, and any other relevant information. Alternatively, the identification could be a coded number providing access through a computer to an address comprising such information. In one embodiment, the automated robotic control of the probe movements requires that the containers are located in the predetermined positions in the receptacles in the reagent section, so that the probe, when lowered, will hit the cover of the container while, at the same time, in a further embodiment, the camera (or another sensor device) may verify the presence or absence of a reagent container and/or read the identification and ensure that the correct reagent will be aspirated.

In an embodiment, the computer system controlling the operation of the robotic system may be programmed to start a new sample processing by performing a search of all reagents, identifying the location of the various reagents and/or the identity of the reagents, such as using the probe to measure the level of all reagents. The computer system may query a central database that contains a record for each individual reagent container and verify, for example, whether a record contains the original and remaining volume of reagent in the container. In a further embodiment, the computer system may be programmed to alert the user if a reagent level is too low to accomplish the staining task for which it is set up. In one embodiment, the computer system may alert a remote location or supplier, such as through a network or the internet, that further reagents are needed. For example, reagents may be automatically provided on a subscription or on demand basis when the system recognizes a predetermined regent level. The client is subsequently billed based on the reagent and amount ordered.

In one embodiment, to accomplish this automated operation, the reagent containers remain fixedly located in the identified positions. Accordingly, in one embodiment, the design of the reagent containers cooperates tightly with the design of the receptacles in the rack assemblies wherein they are located.

In one embodiment, illustrated in FIGS. 11A-11D the container is a 50 ml container 125 having a cross-section that is a rectangle with one corner-section replaced by a slanted/oblique fifth side. The 50 ml container or bottle 125 comprises a bottom 130, five upright sides 131, 132, 133, 134,135 and a top 136 with a neck 137. In an embodiment, the top, as shown in details in FIG. 11B, has identification 138 that is, for example, a label and that identifies the content of the container.

In view of the fact that some reagents are used in various volumes or even seldom, and still others may have a short shelf-life, needing to be replaced often, there may be a need for providing the reagents in containers having different volumes. In order to be able to arrange a plurality of containers having different volumes in the same reagent station with a plurality of identical receptacles, one may, for example, provide an assembly comprising a tube-like covering or shell, called "an adapter", and an internal bottle within the adapter which may be provided in different sizes, having internal volumes of e.g., 1 ml, 2 ml, 5 ml, 10 ml, 15 ml, 20 ml, 25 ml or similar volumes. Generally, the typical reagent volume for an apparatus according to the present invention will be between about 1 ml and 25 ml.

In one embodiment, the covering is a tube-like element 200 (FIG. 11E) having the same outer cylindrical surface as the 50 ml container, i.e., the cross-section is a rectangle with one corner-section replaced by a slanted/oblique fifth side. Accordingly, the adapter 200 comprises the five upright sides 131, 132, 133, 134,135, but, being hollow, does not have a top surface.

In one embodiment, in order to provide for the computer-controlled automated aspiration of reagents, the internal bottles may be arranged in a fixed manner inside the tube-like covering 200 enabling the probe to penetrate in a well-defined manner into the fluid content of the bottle. This may be achieved by providing the covering and the inner bottles with corresponding projections 221 and indentations (not shown) respectively and/or vice versa, ensuring a well-defined position of the inner bottle inside the covering. In one embodiment, the projections should ensure a correct orientation in all directions. It may not be possible to insert the inner bottle into the adapter 200 in any way other than the intended orientation and position. In an embodiment, this is achieved through the combination of projections and indentations, the projections 221, 223 being shown in the FIGS. 11F-11H, relating to the adapter. In one embodiment, the apparatus knows capacity of bottle, for example, by reading encoded information on the bottle, which contains in part an indication of bottle capacity.

Figure 12A:
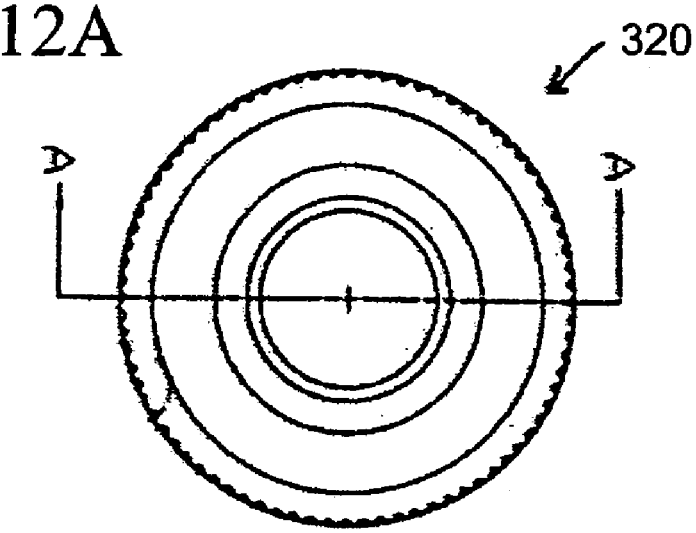
FIG. 12A shows a top view of an example cap for a container.
Figure 12B:
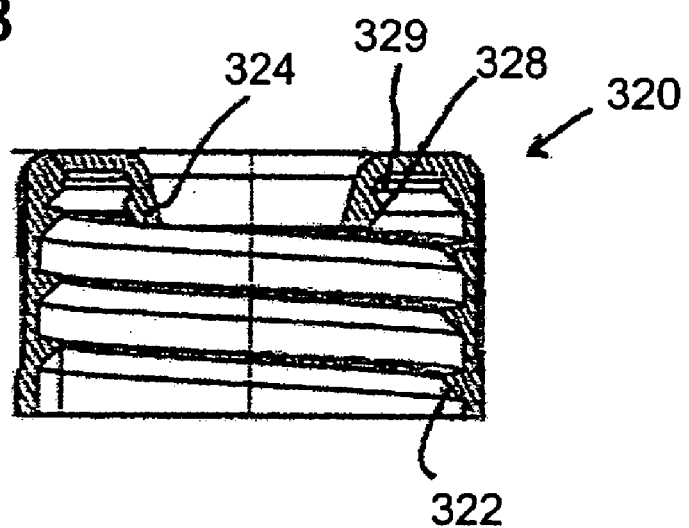
FIG. 12B shows a cross-sectional view of the cap of FIG. 12A.

In an embodiment, a cap 320 (shown in FIGS. 12A-12B) is provided, the cap 320 having an internal thread 322 that mates with an external thread of a corresponding bottle, thereby providing a closure for the bottle. The cap 320 may comprise a circular opening through which the probe may aspirate the fluid content in the bottle. In this manner, no operator has to unscrew a cap in order provide access to the content. The probe may simply reach the fluid content when the probe is lowered by the robotic system until the probe makes contact with the fluid. In one embodiment, a fluid level sensor of the probe is in electrical connection with electronic circuits enabling a determination of the fluid level in the container. Alternatively and in some embodiments, a second database method of reagent volume tracking may be used instead of or in conjunction with previously detailed electronic method. The database method may employ the use of a central networked database to track the usage of a reagent removed by the probe from a specific container and calculates the remaining available volume. In some embodiments, the same central networked database may be used by multiple instruments, such as stainer assembly 1, on the network. The system may further comprise an additional apparatus, for example, automated microtome, tissue processor, special stainer (non-antibody), in-situ hybridization stainer, fluorescent in-situ hybridization stainer, flow cytometry analyzer, flow cytometry sorter, sample transporter, slide imager, and hybridizer. In one embodiment, the additional apparatus is a means for further handling, sorting, processing and analysis of samples. Thus, reagents may be placed on any staining apparatus 1 on the network rather than be restricted for use on a particular staining apparatus 1.

Figure 13A:
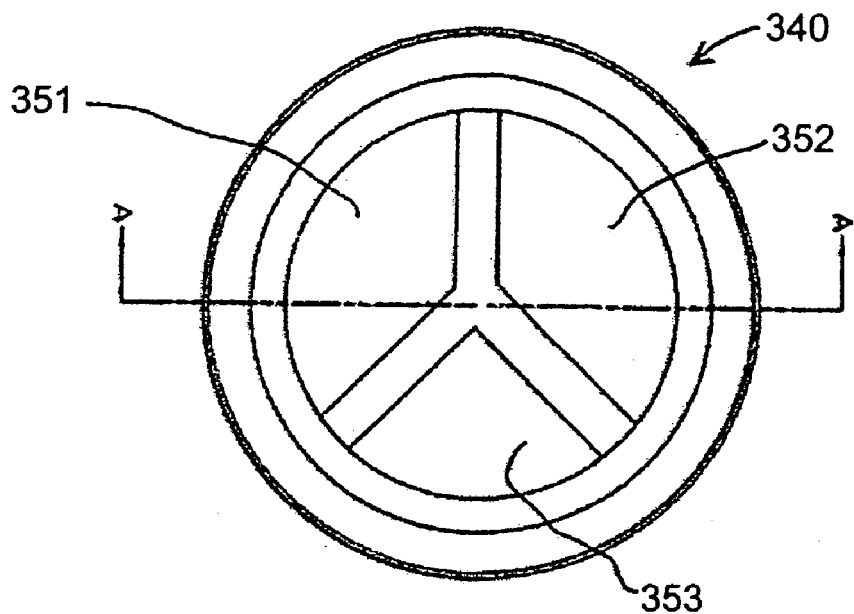
FIG. 13A shows an example septum.
Figure 13B:
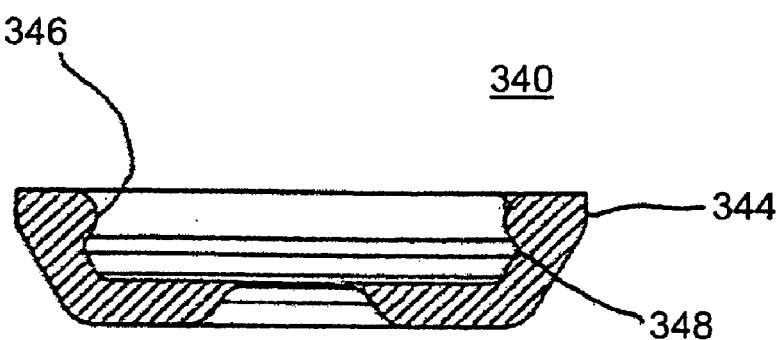
FIG. 13B shows a cross-sectional view of the septum along the line A-A in FIG. 13A.

Tight closures for the bottles may be provided in order to protect the reagent fluids from contamination as well as evaporation. To this end, for example, the circular opening in the cap 320 may include a skirt 324 including a peripheral outwardly projecting rim or lip 328 and a peripheral/surrounding indentation or groove 329 able to cooperate with and fixate a corresponding septum 340 (FIGS. 13A-13B) comprising a flexible material such as polypropylene. The corresponding septum 340 has an upward skirt 344 with an inwardly projecting rim or lip 346 and groove/indentation 348, able to cooperate with the indentation 329 and rim/lip 328 inside the cap 320. When the cap 320 is secured to the bottle neck 255, the upper end of the neck will support and force the lip 346 to stay locked in the groove 329.

In one embodiment, the septum 340 (FIGS. 13A-13B) comprises a plurality of sectors or flaps 351, 352, 353, such as 2, 3 or 4 sectors, which are free to flex upwards or downwards thereby allowing a probe to penetrate the septum. After aspiration of the predetermined amount of fluid, the probe is raised again, thereby being retracted from the reagent bottle. During retraction of the probe, the flaps will wipe off the reagent from the outer surface of the probe. After retraction of the probe, the flaps return to their original position forming an almost tight closure inside the cap on top of the bottle. This septum has several advantages: evaporation of reagent is reduced, and the wiping action of the flaps saves reagent from being carried away on the outer surface of the probe when the probe is raised for movement to the slide section.

Figure 14A:
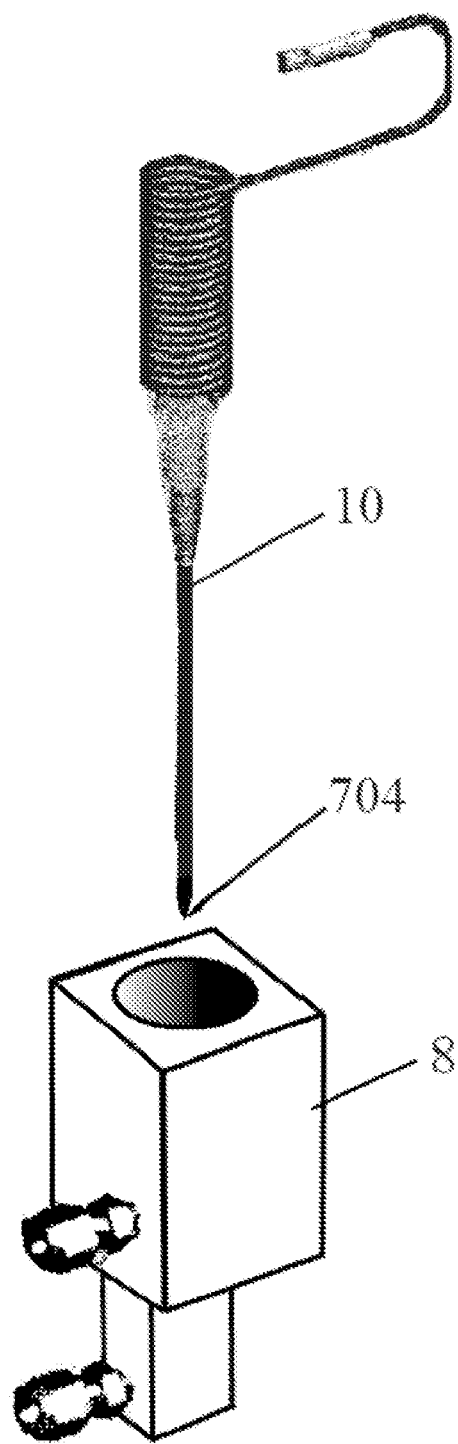
FIG. 14 is an enlarged perspective view of a detail of the work area shown in FIG. 3.
Figure 14B:
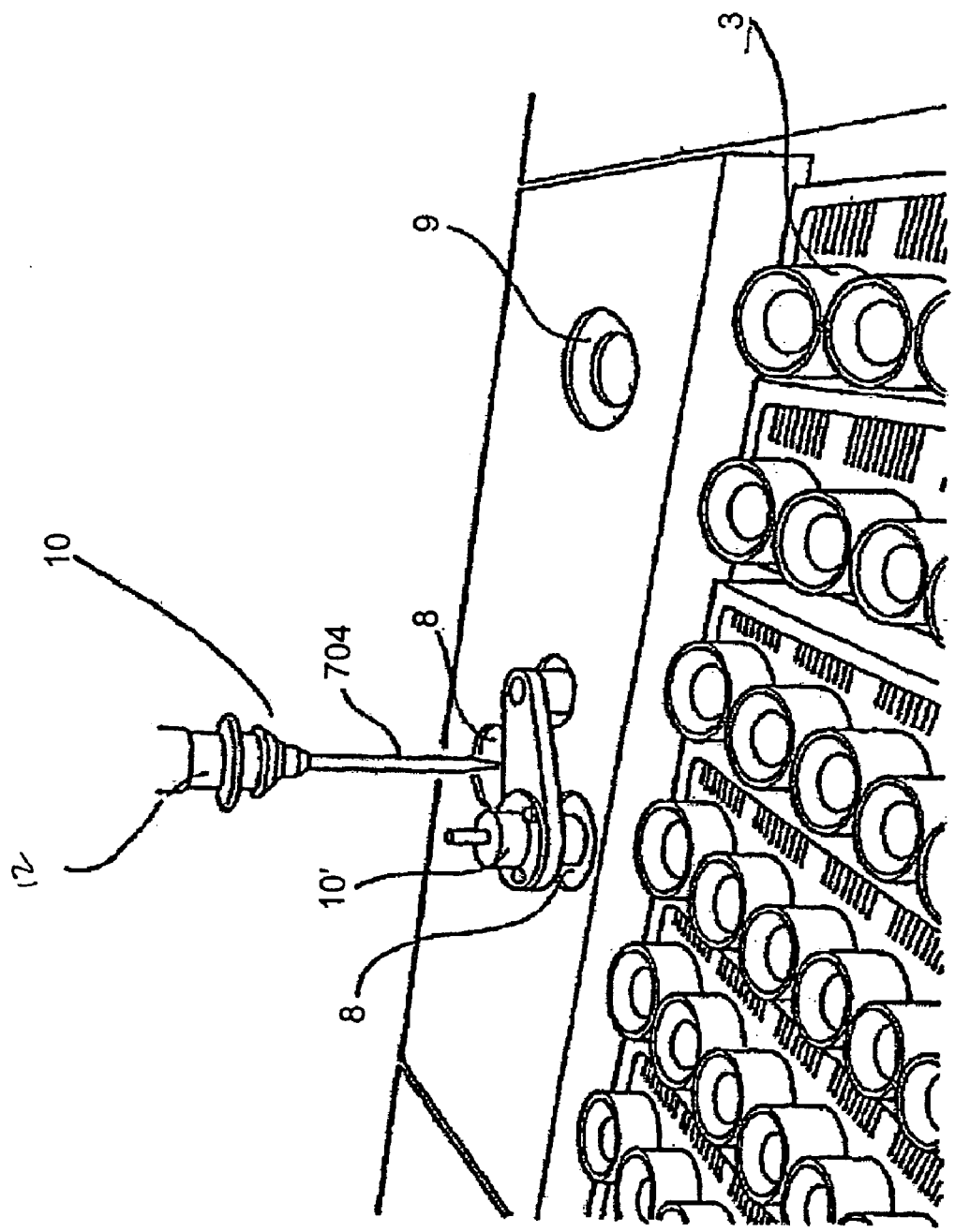

Now, referring to FIG. 14A, as illustrated in detail in that figure, the staining apparatus 1 of one embodiment of the present invention comprises, in an embodiment, at least one probe washing station 8 such that the robot arm is furthermore arranged to transfer the probe tip 704 to the washing station 8. Now, referring to FIG. 14B, as illustrated in detail in that figure, the staining apparatus of one embodiment of the present invention comprises, in an embodiment, at least one probe washing station 8 (see also FIG. 10) and further comprises, in an embodiment, a reagent mixer 9A, such that the robot arm is furthermore arranged to transfer the probe tip 704 to the washing station 8 as well as to the reagent mixer 9A. (The reagent mixer 9A will be described in detail below with reference to FIGS. 15 and 16.)

In some embodiments, in order to support a fast operation, a plurality of probes 10 (such as two, three or four probes, for example) may be provided in order to allow for dispensing different reagents without washing the probe between each dispensing. In the embodiment shown in FIG. 14B, a releasable connection 12 is provided between the probe 10 and the robot arm, enabling the replacement of the probe 10 held by the robot arm by placing the probe 10 in one of a number of free washing stations 8, where it is released by the releasable connection 12, and where a new clean probe 10' is connected to the robot arm by means of the releasable connection 12.

In the one embodiment, the staining apparatus 1 may comprise a reagent mixer 9A having a mixing cup 13 (FIGS. 15, 16) wherein two or more selected reagents may be placed by means of the robot arm and the probe 10 and mixed. The reagent mixer 9A thereby provides on-board mixing of any reagents contained in the reagent containers 3, which, for example, comprises the bottles 125 (FIGS. 11A-11D). The reagent mixer 9A, thereby, enables more staining processes, e.g. staining requiring the use of mixing of insoluble reagents, or reagents which may only be effective a short time after mixing, are facilitated to be performed automatically within the staining apparatus without the requirement of human interaction.

Figure 15:
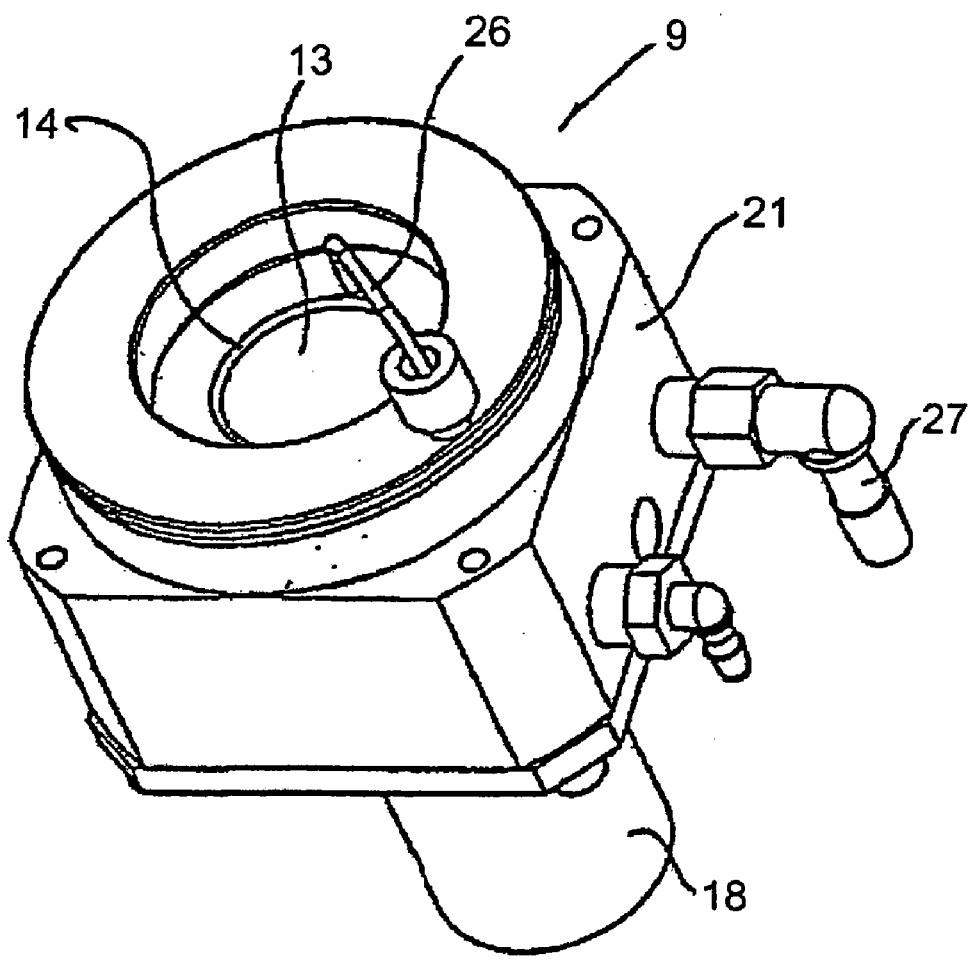
FIG. 15 is a perspective view of an example reagent mixer according to the invention.
Figure 16:
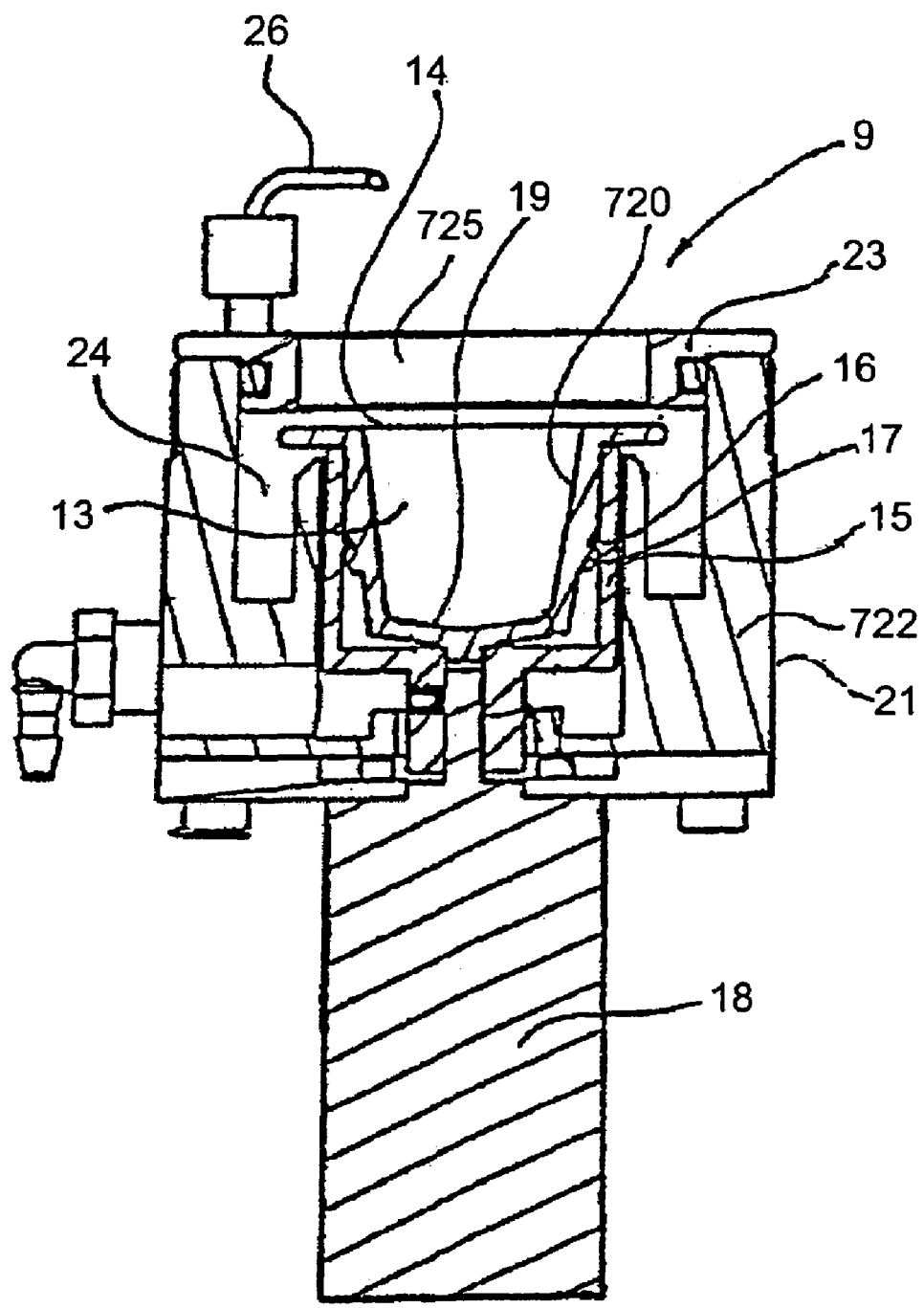
FIG. 16 is a vertical cross-section of the reagent mixer according to FIG. 15.

On embodiment of the mixer 9A is shown in detail in FIGS. 15-16, and comprises a mixing cup 13 for receiving reagents released from the probe 10. The mixing cup 13 is placed into a holder 15 by means of a complementary snap fitting means 16 and 17 arranged on the inside of the holder 15 and the outside of the mixing cup 13, respectively. A motor 18 is arranged for rotating the holder 15 and thereby the mixing cup 13, either intermittently clockwise and anticlockwise in order to provide a mixing of reagents contained in the mixing cup, or by spinning the holder 15 and thereby the mixing cup 13 in order to fling out waste reagents or cleansing liquid from the mixing cup 13.

For the latter purpose, the mixing cup 13 may be provided with sidewalls 720 extending upwardly and outwardly from the bottom 19, e.g. forming a frusto-conical cavity, and the mixing cup 13 has an upper rim 14 allowing the reagents to escape from the mixing cup 13 during the spinning process. Further, the rotating action of the cup allows air to escape from the mixture and prevent foaming. The rotating action can suppress the formation and build-up of foam by forcing the air/liquid foam down to the liquid surface.

The reagent mixer 9A furthermore comprises a housing 21 having sidewalls 722 surrounding at least the rim 14 of the mixing cup 13 and thereby forming splash faces for collecting any liquid flung out from the mixing cup 13. The housing also comprises a lid 23 for enclosing a space 24 surrounding the mixing cup 13 in order to avoid reagent spills outside the space 24. The lid 23 has a central opening 725 allowing reagents from the probe 10 to be dispensed into the mixing cup 13 from above the reagent mixer 9A as well as allowing the probe 10 to enter the mixing cup 13 for collecting the mixed reagents.

According to an embodiment of the present invention, the housing also comprises a hose connection 27 for draining waste reagent or cleansing liquid from the space 24, and a tap 26 is arranged for dispensing cleansing liquid into the mixing cup 13 when required.

In one embodiment, having the appropriate input data, the control means of the apparatus operates the robot arm to commence a staining or treatment group by firstly moving the probe to a first reagent container 3, into which the probe tip 704 is inserted. Once the probe tip is inserted into the liquid of the container, liquid is aspirated into the probe 10 in an amount corresponding to the number of samples to be stained or treated, in accordance with the input data provided to the control means.

One example embodiment may be described as follows. The probe 10 is subsequently, in a first operating mode moved by the robot arm towards the slide section 5 in which the slides 7 are mounted. The slides 7 are situated with the surface 7 horizontally oriented and the probe 10 releases the required amount of reagent on the appropriate slides in accordance with the input data. Alternatively, the probe 10 is in a second operating mode moved by the robot arm towards the reagent mixer 9 where it releases the reagent into the cup 13 of the reagent mixer 9, and is subsequently moved to the probe washing station 8, where the probe 10 is either washed or—in the alternative embodiment (FIG. 14)—released into a free washing station 8, and another probe 10' situated in another washing station 8' is connected to the robot arm. The robot arm moves the new clean probe 10' to a second selected reagent container 3 for collecting a selected amount of reagent from the second container 3, and the probe 10' is thereafter by means of the robot arm moved to the reagent mixer 9, where the reagent in the probe 10' is dispensed into the cup 13 of the mixer containing the first selected reagent. The second operating mode can, according to the invention, be commenced several times if more than two reagents are to be mixed for a specific staining or treatment process.

The reagent mixer 9 mixes the reagents in the cup 13 thereof. Probe 10 is lowered such as via the robot arm into the cup 13 of the reagent mixer 9 to collect the mixed reagents, whereafter the robot arm moves the probe 10 towards a slide section 5 containing the slides 7, at which the probe 10 releases the required amount of mixed reagent on selected slides 7 in accordance with the input data. For an embodiment wherein multiple probes may be utilized, a clean probe 10 may be picked up from the washing station 8 by the robot arm and lowered into the cup 13 of the reagent mixer 9 to collect the mixed reagents, whereafter the robot arm moves the probe 10 towards a slide section 5 containing the slides 7, at which the probe 10 releases the required amount of mixed reagent on selected slides 7 in accordance with the input data.

The robot arm with probe 10 is subsequently directed to a free washing station 8, and the probe 10 is either washed or alternatively replaced by a clean probe 10', whereafter the process in accordance with the first or the second operating mode may be repeated or continued with a new reagent or reagent mixture.

Figure 7B:
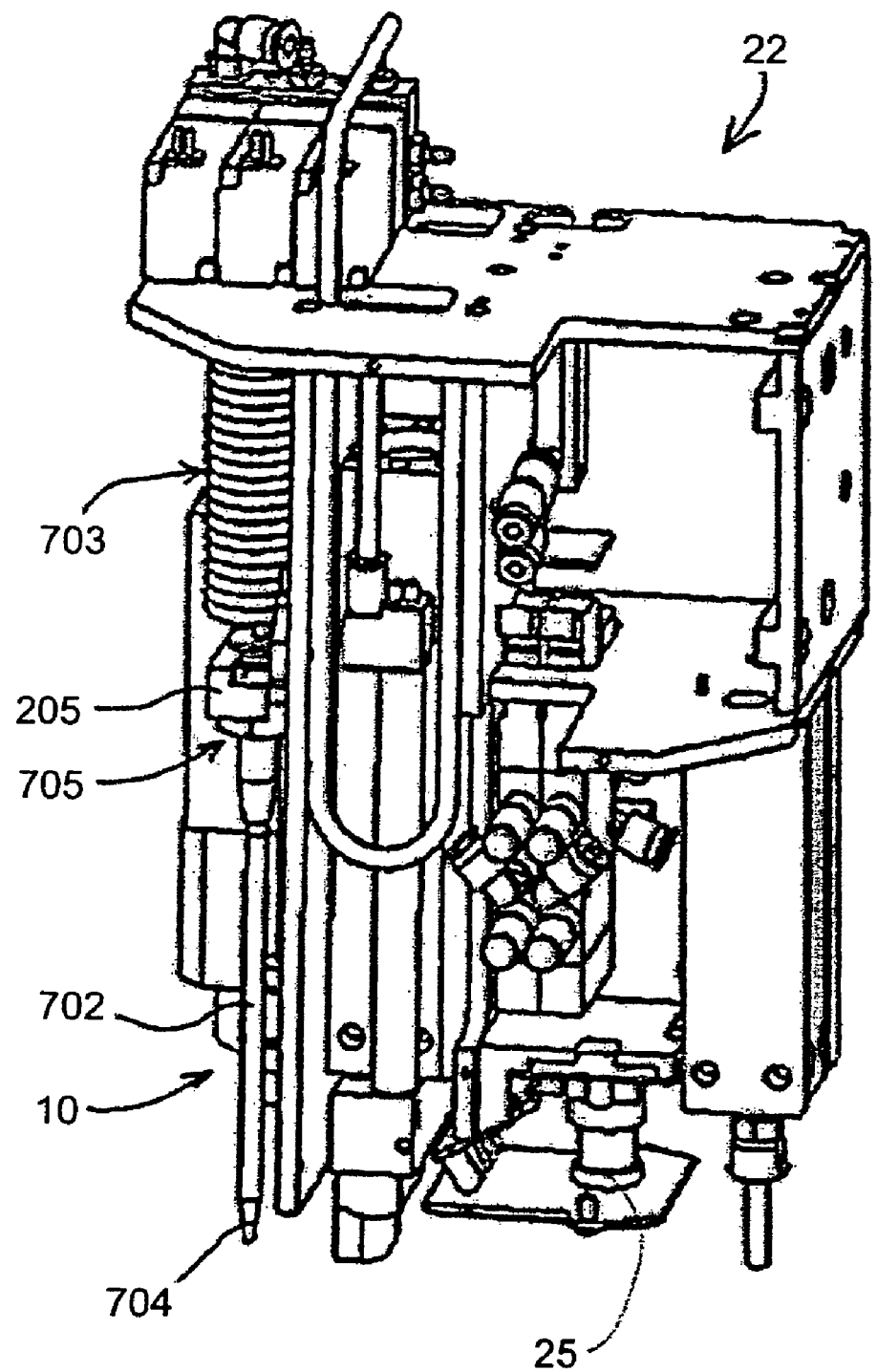
FIG. 7B shows a first view of an embodiment of a robotic head with a probe mounted thereon.
Figure 7C:
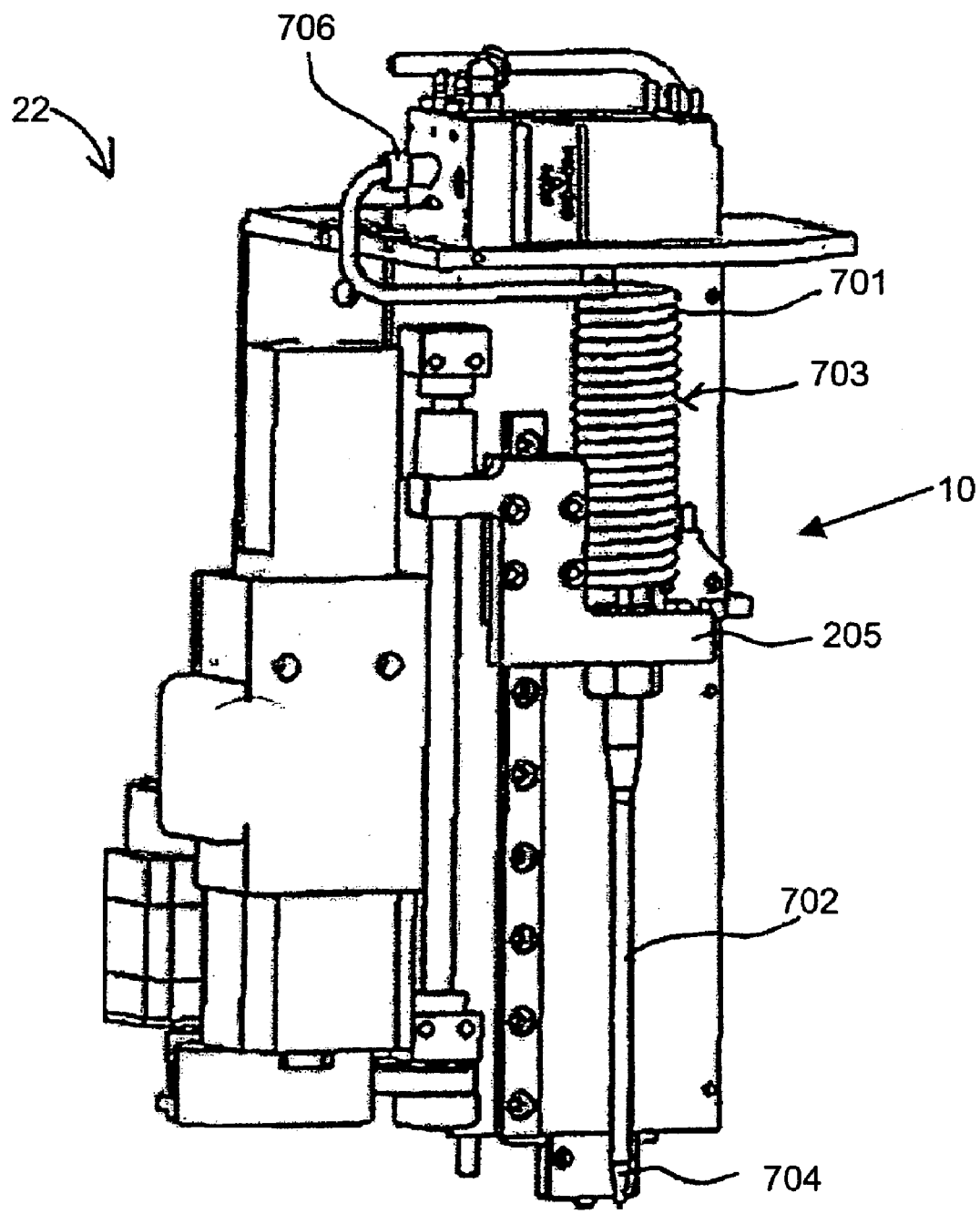
FIG. 7C shows a second view of the robotic head of FIG. 7B, viewed perpendicular to the view in FIG. 7B.

In an embodiment, the present invention may include providing an optical sensor 25 on a robotic element and may perhaps move the optical sensor to a predetermined position through action of the robotic element. As but one example, the robotic head 22 may be provided with an optical sensor 25, perhaps even a CCD camera 25 pointing downwards (FIGS. 7A-7B). The optical sensor 25 may be positioned on or, perhaps, more broadly in response to, the robotic element. After the optical sensor 25 is positioned, image data may be recorded at the location at which the optical sensor 25 is established. The camera can be used, for example, as an area locator, to locate a tissue area, to apply reagent based on location and area, to determine presence or absence of a sample carrier 7 or reagent container. In one embodiment, the camera may to record the appearance of a tissue sample and/or monitor the condition of the apparatus, such as slide alignment, slide presence, reagent bottle presence and/or alignment. The scanned image may be analyzed for reagent analysis or other analyses.

Figure 11A:
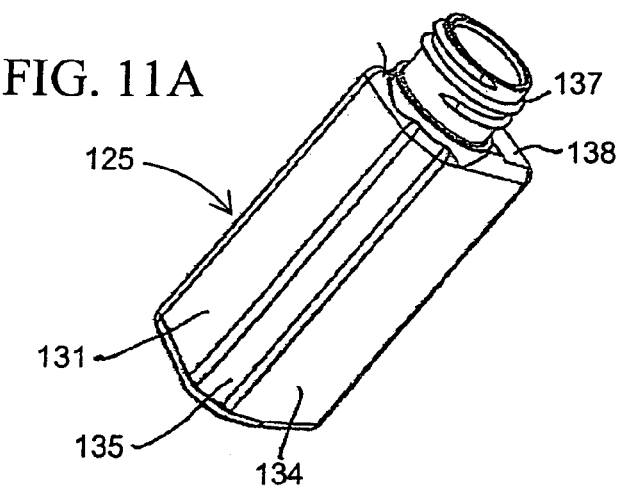
FIG. 11A shows a perspective view of an example 50 ml reagent container.
Figure 11B:
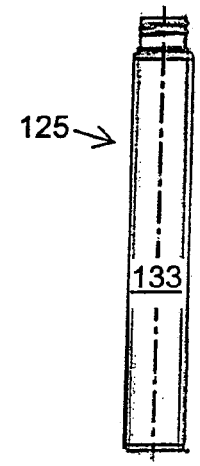
FIGS. 11B and 11C show side views of the same container of FIG. 11A.
Figure 11C:
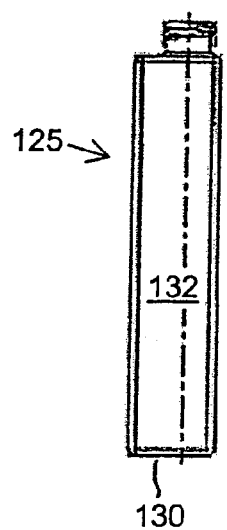
Figure 11D:
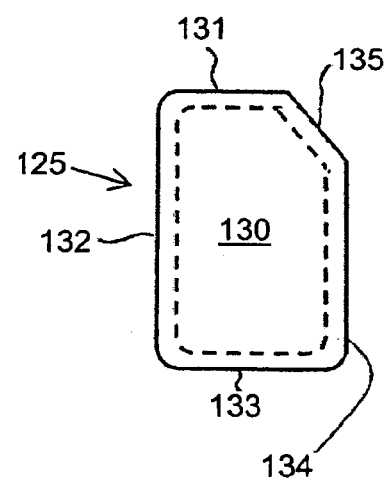
FIG. 11D shows a bottom view of the same container of FIG. 11A.
Figure 11E:
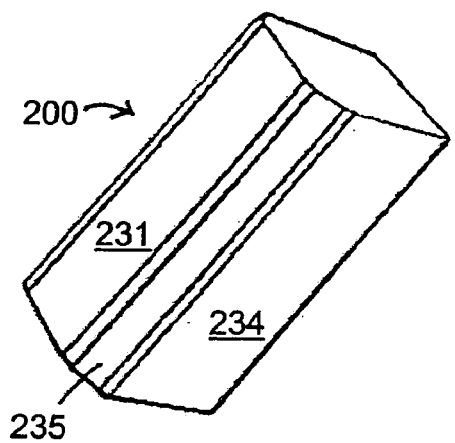
FIG. 11E shows a perspective view of an example adapter or covering for accommodation of smaller containers.
Figure 11F:
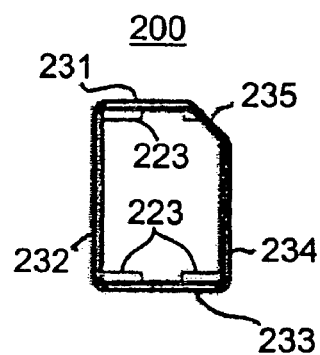
FIG. 11F shows a bottom view of the adapter of FIG. 11E.
Figure 11G:
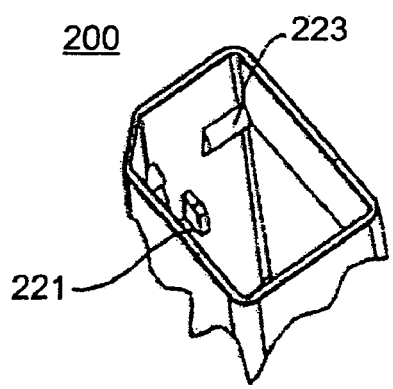
FIG. 11G is a perspective view of the adapter of FIG. 11E seen from the top
Figure 11H:
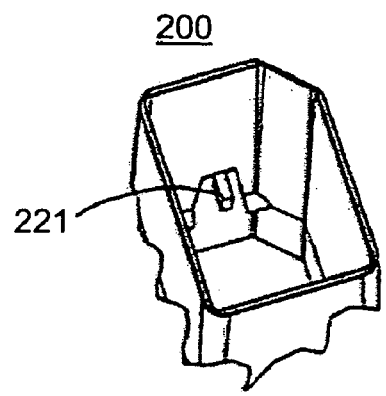
FIG. 11H shows a perspective view of the adapter of FIG. 11E, seen from the bottom.
Figure 17:
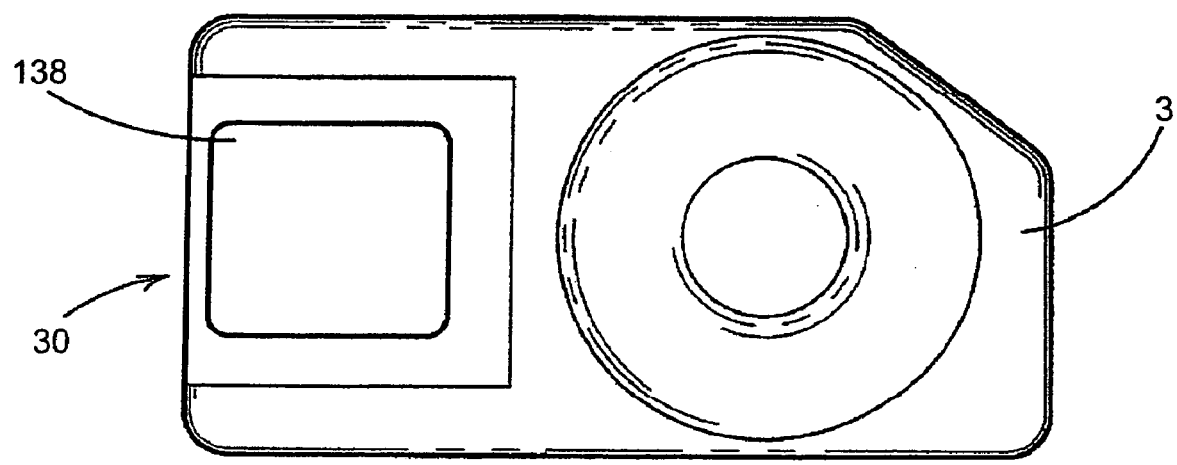
FIG. 17 is a top view of an example reagent bottle with an example optical identification means.

As shown in FIG. 17, the reagent container 3 may be provided with an area 30 on a surface on which to mount an optical identification element 138 (FIG. 11A, FIG. 17). This optical identification element may be an adhesive label carrying encoded information about the content of the container 3, such as reagent type, date of manufacture, expiry date, and/or a unique identification 0number that identifies the reagent container such as in a central networked database. The encoded information may be in the form of a data matrix code, an Infoglyph™ code or any other kind of two-dimensional (2-D) code, and could in principle also be a simple one-dimensional (1-D) code, i.e. a bar code. The aforementioned encoded information may correspond, for example, to unique identification which may be utilized, for instance, to retrieve certain data from a central database server. Additionally, the optical identification element or label 138 may also be provided with human readable text to aid the operator handling the reagent containers e.g. during loading of containers into the staining apparatus. Additional types of identification may also be employed for identifying slides and/or reagent bottles such as utilizing Radio Frequency (RF) tag or RF data carrier technology (examples, of which, are described in U.S. Pat. Nos. 6,941,202, 6,922,146, 6,883,710). Additional alternatives include but are not limited to identifying samples as described in U.S. patent application Ser. No. 11/168,987, the contents of which are hereby incorporate by reference.

Figure 18:
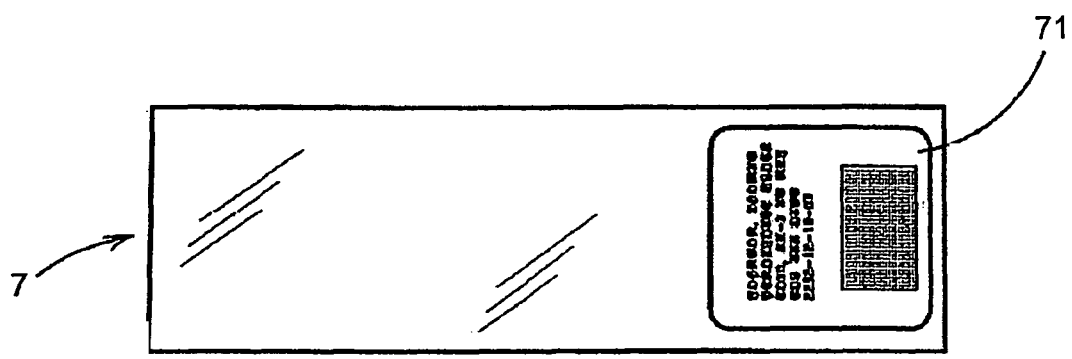
FIG. 18 is a view of an example microscope slide with an example optical identifier label thereon.
Figure 19:
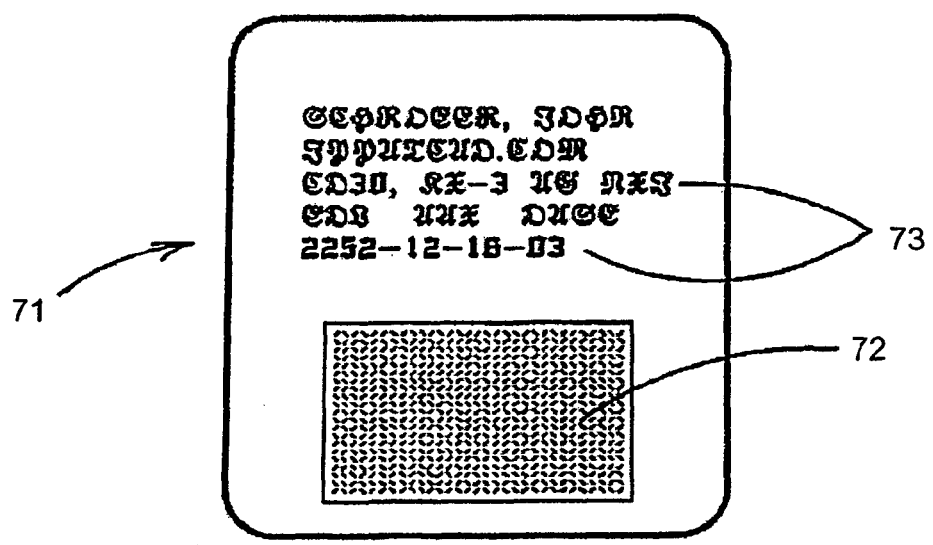
FIG. 19 is an example of a lay-out of the label of FIG. 18.

FIG. 18 shows a slide 7 with an example optical identification element, that is label 71, mounted thereon. One layout of the label 71 is shown in FIG. 19. The label 71 may be an adhesive optical identifier, which may be prepared for the particular slide and printed on a label printer (not shown) or any other suitable printing device. Some embodiments provide that every slide has its own unique identifier. The label 71 may comprise an area 72 for encoded information about the tissue sample on the slide 7, such as patient data, date and file number, the staining protocol and/or the series of process steps or a unique identification number that may identify a slide in a central networked database. Furthermore, the label 71 may be provided with one or more rows 73 of human readable text and/or blank space for the laboratory personnel preparing the slides to write on the slide label.

Figure 20:
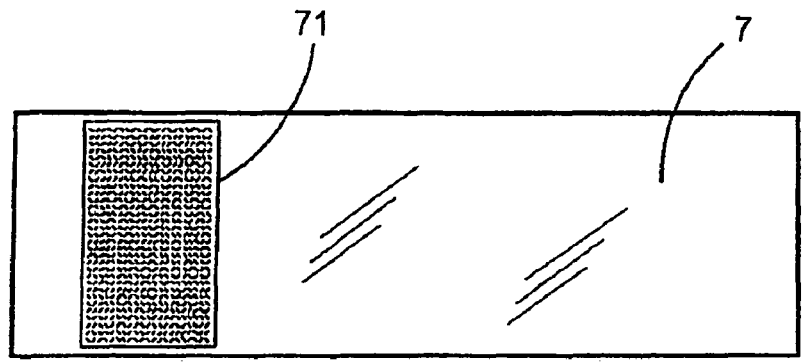
FIG. 20 is an example of a first kind of optical identifying means on a slide.
Figure 21:
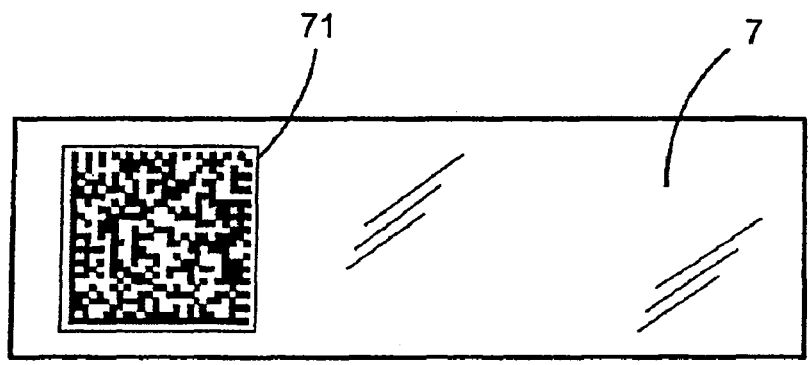
FIG. 21 is an example of a second kind of optical identifying means on a slide.
Figure 22:
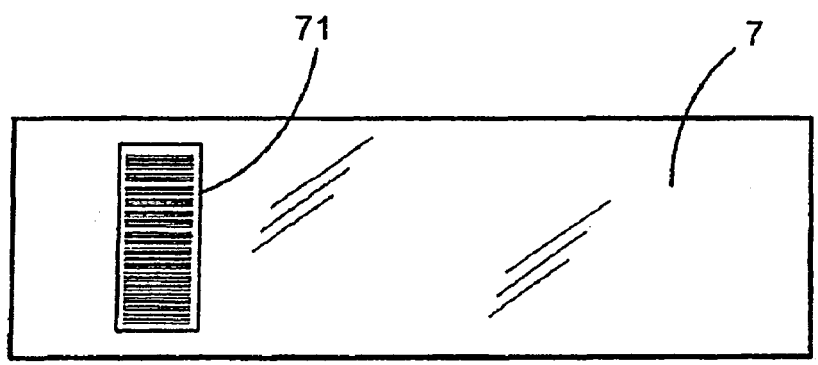
FIG. 22 is an example of a third kind of optical identifying means on a slide.

In FIGS. 20 to 22 various kinds of data encoded symbology for the label 71 (the entire label 71 as shown or only for the label area 72 (see FIG. 19)) are shown. Again, the encoded data may correspond, for example, to a unique identification which may be utilized, for instance, to retrieve certain data from a central database server.

In FIG. 20, an example of a 2-D symbology of the Infoglyph™ type is shown. This may include perhaps even an information carpet type of symbology. This type of 2-D symbology is advantageous since it can carry a large amount of optically machine readable information. Making use of a high-resolution camera, this type of symbology may be readable in a high resolution and a large amount of information can be encoded therein. The symbology may be printed with tiny diagonal lines in different directions or perhaps even colors and can easily be read by a CCD camera or the like.

FIG. 21 shows an example of a data matrix code that can be used as an alternative to the Infoglyph™ symbology. The data matrix is similarly readable with a CCD camera but may not carry as many data in the encoding as the Infoglyph™. However, it is easier to print as it may have a less high resolution making it a simple and cost effective solution if less identification data on the slides and the reagent bottles is required. A yet simpler solution is shown in FIG. 22, where the symbology is a conventional bar code. In principle, this means that only a bar code scanner is required for reading the slides and the reagent bottle information, but by using a 2-D sensor, the possibility of self-calibration and monitoring the installation of slides and reagents in the staining apparatus may be enhanced. Another solution may include using human-readable characters and optical character recognition (OCR) capabilities of the software such as by processing the CCD camera image.

In an embodiment, the optical identifiers on the slides and on the reagent bottles are the same type. This may facilitate the image processing of the identification process in the staining apparatus.

Figure 23:
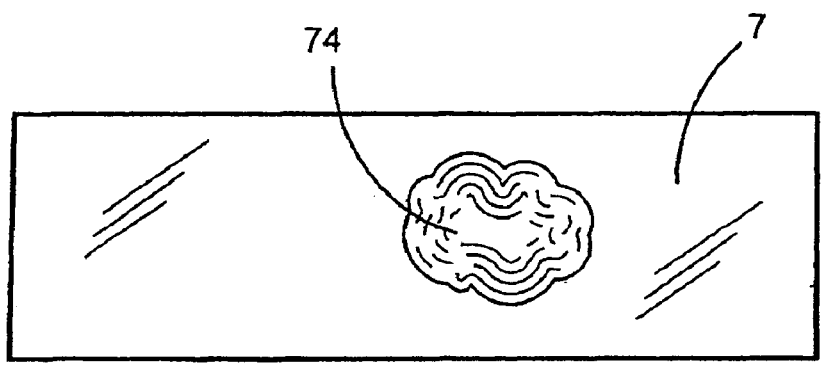
FIG. 23 is an example of a fourth kind of optical identifying means on a slide.

A different approach to identifying the individual slides or as a way of facilitating the new capabilities of confirming identification or storing confirmatory information may be to record the contour and/or the texture of the tissue sample 74 itself, such as shown in FIG. 23. Utilizing the high-resolution of the image that can be recorded by the camera, the unique features of the tissue sample itself can be used as a graphical identifier of the slide. Furthermore, an image of the stained tissue sample can be recorded so that a digital representation of the tissue sample is produced. This digital image can be sent electronically to remote locations for instant examination and/or archived for later examination. This may provide the staining apparatus with a unique flexibility in use and may introduce new and advantageous methods of analyzing the tissue samples.

Besides identifying the microscope slides and the reagent bottles in the staining apparatus, the 2-D optical sensor can also be used for self-calibration of the apparatus, e.g. after maintenance, if the apparatus has been disassembled or moved to another location. By identifying critical locations within the apparatus by capturing an image by the camera, the image processing software can compare the captured image with a reference image to determine if certain critical components in the apparatus are off-set from their predetermined positions, e.g. if a slide rack or a slide is slightly off-set, and if so, a set of correction data for the robotic motion control system may be calculated and this set of data may be used for calibrating the apparatus.

Figure 30:
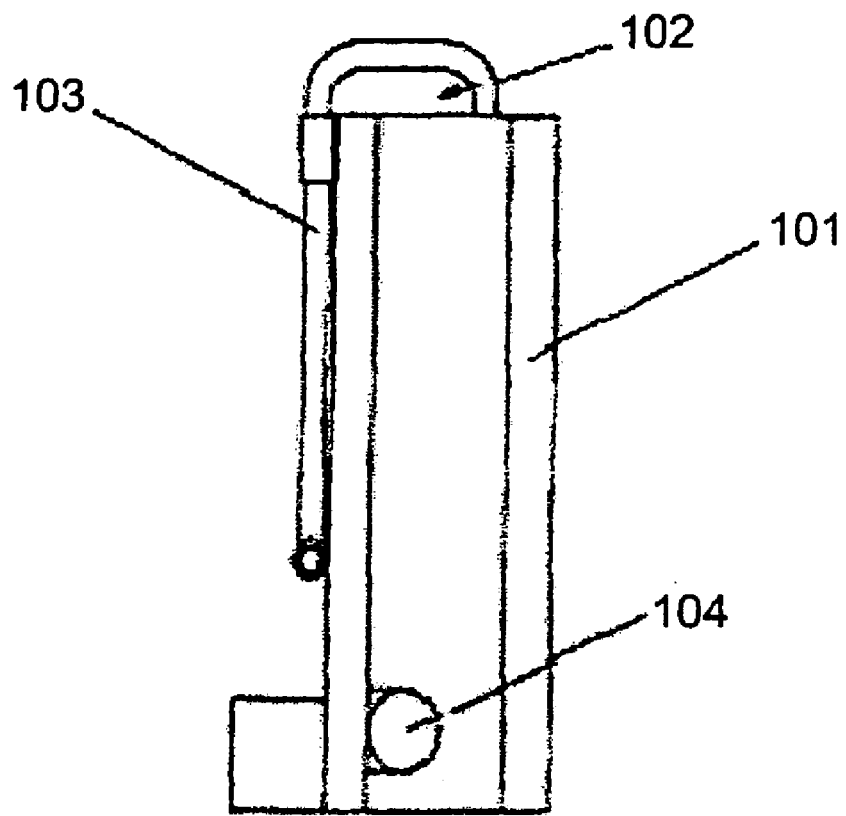
FIG. 30 is a front view of the processing tank of FIG. 29.

The discussion is now directed to the drawer assemblies and the components therein. A perspective view of an embodiment of a drawer assembly 100 is shown in FIG. 28 and a side elevation view is provided in FIG. 24. Other perspective views of drawer assemblies are provided in FIGS. 25 and 26. The slide rack assembly 6 component of the drawer assembly 100 is shown in FIG. 27 and the processing tank 101 component is shown in FIGS. 29 and 30. The drawer assembly may comprise a slide rack, module, and/or magazines. It may be observed from FIG. 24 that the slides 7 (or, more generally, sample carriers) in the slide rack 6 are loaded and unloaded in a horizontal position when the slide rack is in an upper position. The slide rack is arranged in a slide elevator 63 and the slide holder 62 is adapted to pivot the slide 7 between a horizontal position and a vertical position 7v, when the slide rack 6 is in its upper position. The slide rack and the slide rack elevator 63 are arranged as a moving part 100a of a drawer assembly 100. In a corresponding stationary part 10b, or slide staining platform portion, of the drawer assembly 100, a processing tank 101 is provided.

In certain embodiments, as illustrated in FIGS. 1A and 3, one or more drawer assemblies 100 can be slid to an open position without interrupting the operation of the staining apparatus 1. In certain embodiments, one or more drawer assemblies 100 can be removed from and/or placed into the staining apparatus 1 without interrupting the operation of the staining apparatus 1. Removal of certain drawer assemblies 100 can facilitate cleaning and/or repair of the drawer assemblies without causing the staining apparatus 1 to stop operating. As a result, in certain embodiments, the staining apparatus 1 can operate with increased reliability and minimal, if not zero, downtime.

In one embodiment, the activities of one or more drawer assemblies 100 may be directed via an embedded PC assembly, for instance, located within the electronics assembly of the staining apparatus 1. The drawer assembly components which may be controlled or monitored by a drawer assembly electronics module may include processing tank fill and drain valves, processing tank heater and thermistor, rack-present sensor, rack-up sensor, rack-down sensor, step motor for the rack elevator, slide thermoelectric devices (TEDs), temperature sensing thermistors and slide drawer lock. In one embodiment, a drawer assembly electronics module may consist of a single drawer control printed circuit board assembly (PCBA) in communication with a TED control PCBA and a slide drawer power PCBA.

By way of example, a reagent drawer electronics module may be utilized in communication with the embedded PC (such as via RS485 serial communication bus connection) in order to facilitate monitoring the activities of one or more drawer assemblies 100. The reagent drawer electronics module may also be utilized in connection with the embedded PC of the staining apparatus 1 to direct activities of the reagent drawer.

Reagent drawer components controlled or monitored by the reagent drawer electronics module may include mix well and probe wash valves, a step motor for agitation and spin, reagent bottle thermoelectric devices (TEDs), temperature sensing thermistors and reagent drawer locks. A reagent drawer electronics module may consist of a drawer control PCBA in communication with a reagent drawer power PCBA.

A design of one or more drawer assemblies 100 utilized in combination with the staining apparatus 1 may include non-interruption of slide staining processes when one or more of the drawer assemblies 100 are removed and/or replaced. Implemented software that incorporates an adaptive scheduling capability utilized by the staining apparatus 1 and the hardware configuration of the drawer assembly may facilitate continuous and uninterrupted operation of the staining apparatus 1.

In one embodiment, a drawer may be indicated as inoperative, for example, by an indicator element 712 such as an LED. Optionally, or in combination, a software program may indicate an inoperative message to an operator. In order to service the drawer, the software may be configured to signal the electronic control system of the staining apparatus 1 in order to perform preparatory functions such as turning off electricity to the respective drawer(s), stopping pumping of fluids through connections to the drawer(s), and indicating to the staining apparatus 1 system that the drawer(s) will be taken off-line. In some embodiments, the drawer assembly software module readies electrical and fluidic interfaces for disconnection and reconnection without interrupting other processes on the remaining drawers which may be occurring within the staining apparatus 1. Hence, an operator may disconnect any fluidics interface(s) to the drawer desired to be removed from the staining apparatus 1. Additional operations may include disconnection mounting hardware of the drawer assembly connected, for instance, to a frame assembly of the staining apparatus 1.

Once the drawer to be serviced is disconnected from the staining apparatus 1, it may be removed, serviced, and reassembled or, alternatively, another drawer assembly may be inserted in its place. Once another drawer assembly is inserted, appropriate fluidic, hardware, and/or electrical connections may be made to the frame assembly of the staining apparatus 1.

Upon reassembly of the drawer assembly 100 to the staining apparatus 1, the software may be accessed to perform one or more functionality tests including, for example, to verify that the fluidics valves associated with the drawer are operational, that the sensors and indicator lights are operative, that the rack elevation and its associated sensors and motor are operational, and that the processing tank temperature control elements is functioning properly. When functional, new samples may be loaded within the drawer assembly for subsequent processing. The software may be programmed to accommodate the new samples, for instance, by modifying an adaptive scheduler to process the newly admitted samples. The aforementioned replacement of one or more drawers may occur with continuous processing in the other drawers in the staining apparatus 1 with downtime localized to the drawer being serviced or replaced.

Figure 32:
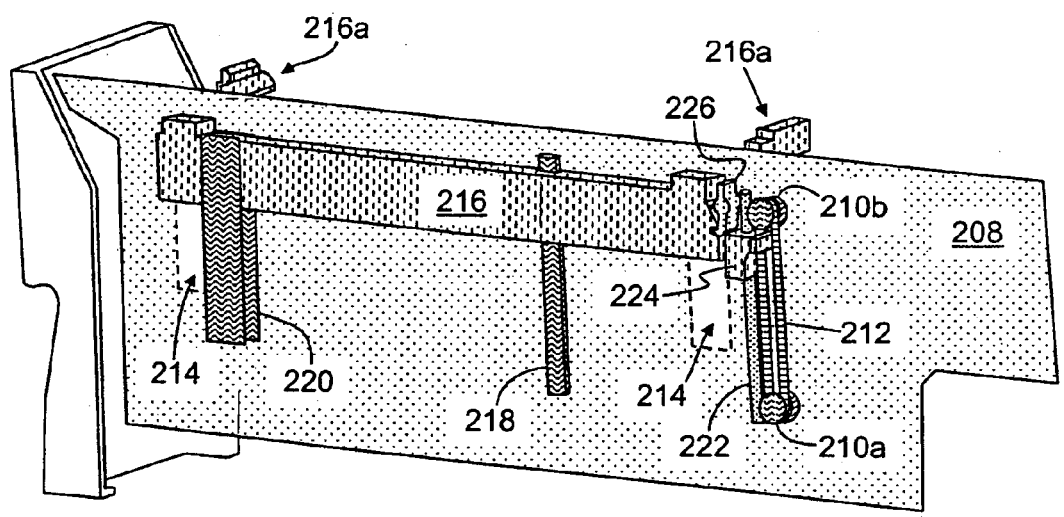
FIG. 32 is a detailed view of the slide rack elevator of FIG. 24.

A detailed view of an example slide rack elevator 63 is provided in FIG. 32. The slide rack elevator mechanism moves the rack containing the slides up and down, either into and out of the processing tank 101, or up and down into the slide staining platform position. Only those slides within a slide rack that have previously been flipped into a vertical position will be lowered into the processing tank 101. Slides that are in a horizontal position will be lowered, by slide rack elevator 63, onto the slide staining platform so as to possibly come to rest upon the top surface of a temperature control member 64 within the non-moveable portion 100b of a drawer assembly 100 (FIG. 26).

The slide rack elevator components may be mounted onto a side panel 208 of the moving part portion 100a of a drawer assembly 100. In one embodiment, these slide rack elevator components may comprise a stepper motor (on opposite side of panel 208 from the viewing position and therefore not shown) a first pulley 210a that is driven by the stepper motor, an elevator belt 212 that engages with the first pulley 210a, a second pulley 210b with which the elevator belt also engages, a clamp 224 secured to and moving with the elevator belt 212 and an elevator bar 216 attached to the clamp 224. The clamp 224 travels or rides along or upon an alignment post 222 that passes through clamp 224 and constrains the motion of clamp 224 to within one dimension (i.e., vertical). The elevator bar has, attached to it, two elevator arms 216a that pass through slots 214 in the panel and that mate with and support a slide rack 61 (not shown in FIG. 32; see FIG. 27), the slide rack being disposed at the opposite side of the panel 208 from the viewing position of the drawing. The elevator bar is constrained to move in one dimension (i.e., vertically) by alignment guides such as rail 218 and rail 220. Using the elevator mechanism shown in FIG. 32, motion of the stepper motor drives mechanical motion of belt 212 which drives vertical motion of clamp 224, elevator bar 216, elevator arms 216a and, ultimately the slide rack supported by elevator arms 216a.

In an embodiment of the present invention, an apparatus comprises eight drawer assemblies 100, as shown in FIG. 1. However, it is realized that any other number may also be provided depending on the design preferences. Each drawer assembly 100 may include (FIG. 24) a drawer slide, a slide rack elevator 63, a slide rack assembly 6 including slide temperature control members 64 which are, for example, platforms having thermo-electric modules, a processing tank 101, a drip tray 65 for collecting staining fluids and control means including indicators for various user information and process surveillance purposes.

The slide rack assembly 6 is shown in FIG. 27. The slide rack assembly 6 includes a slide rack 61, for example, with a capacity of eight slides 7 in individual slide receiving compartments 68, as shown in FIG. 27. In connection with each compartment 68, a slide holder 62 is provided. The slide holders 62 include pivoting means including slide holder clips 69 which are pivotable between a horizontal slide position and a vertical slide position and activation means 67. The slides 7, 7v are individually pivotable in their slide holders 62, as the slide holder clips 69 may be pivoted by a pushing force, via push tool 38 (FIG. 7A), of surfaces accessible through access holes 67 in slide rack 61 (FIG. 27), of which two are provided, one for pivoting from a horizontal to a vertical position and one for returning the slide from a vertical to a horizontal position.

Figure 33:
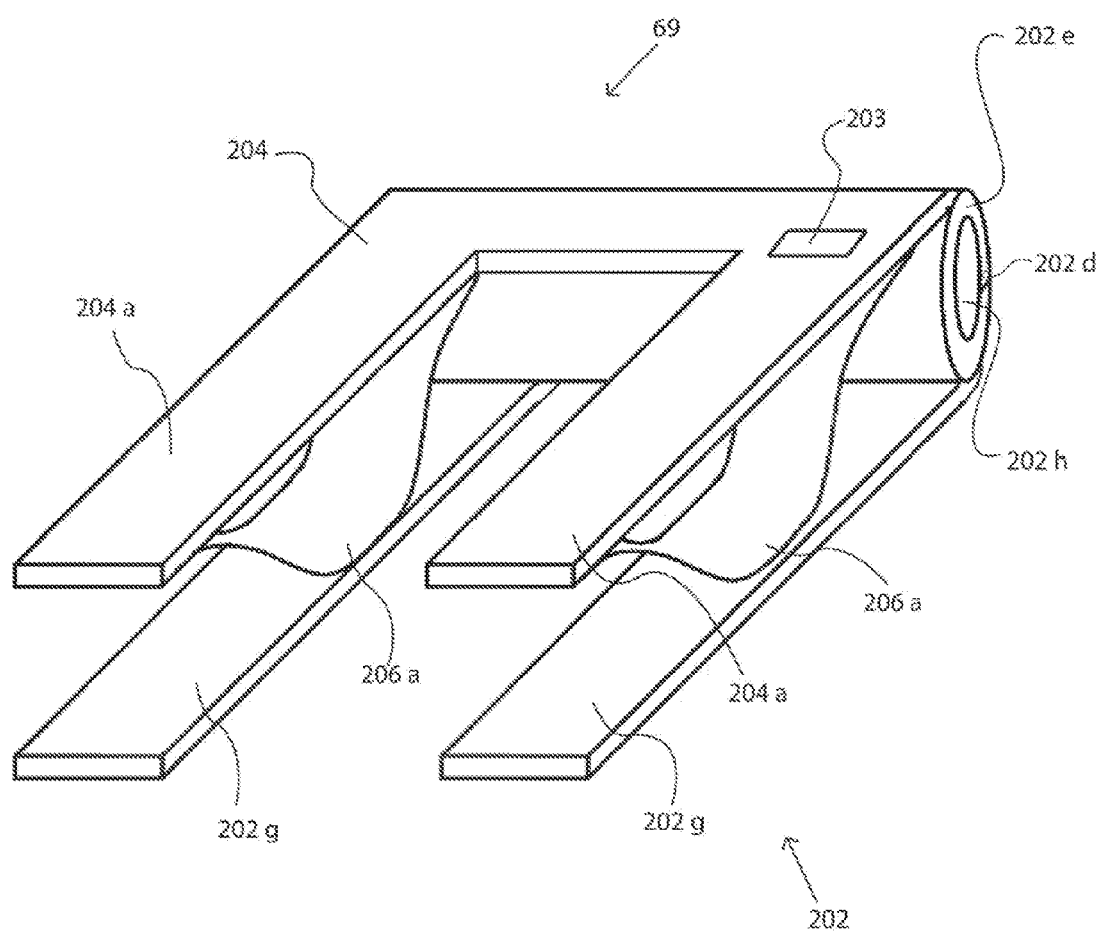
FIG. 33 is a detailed view of one embodiment of a slide holder clip as utilized within an embodiment in accordance with the present invention.

FIG. 33 provides a detailed view of an example slide holder clip 69 for use within an apparatus in accordance with an embodiment of the present invention. The slide holder clip 69 (FIG. 33) comprises a lower body member 202 having two front-facing arm portions 202a, a rear ledge portion 202p and a rearward disposed cylinder-shaped flange pivot portion 202e having a circular hole 202h therein. The slide clip holder 69 further comprises a spring clip 206 and an upper retainer portion 204 physically coupled to the lower body member 202 and retaining the spring clip 206 in place against the lower body member 202. The upper retainer portion 204 has two front-facing arm portions 204a. These arm portions 204a are rigidly formed. The upper retainer portion 204 has slide detection means 203 disposed proximal the pivot axis of slide holder clip 69 and along at least one arm portion 204a. The slide detection means 203 may be a viewing window for detecting the presence or absence of a slide 205 via the optical sensor 25. The spring clip 206 has two arms 206a that are respectively disposed above each of the two arm portions 202a of the lower body member 202 and attached to the upper retainer portion 204 along arm portions 204a. Each arm 206a of the spring clip 206 has a bow-shaped bend which is the lowermost portion of each arm 206a.

Figure 33A:
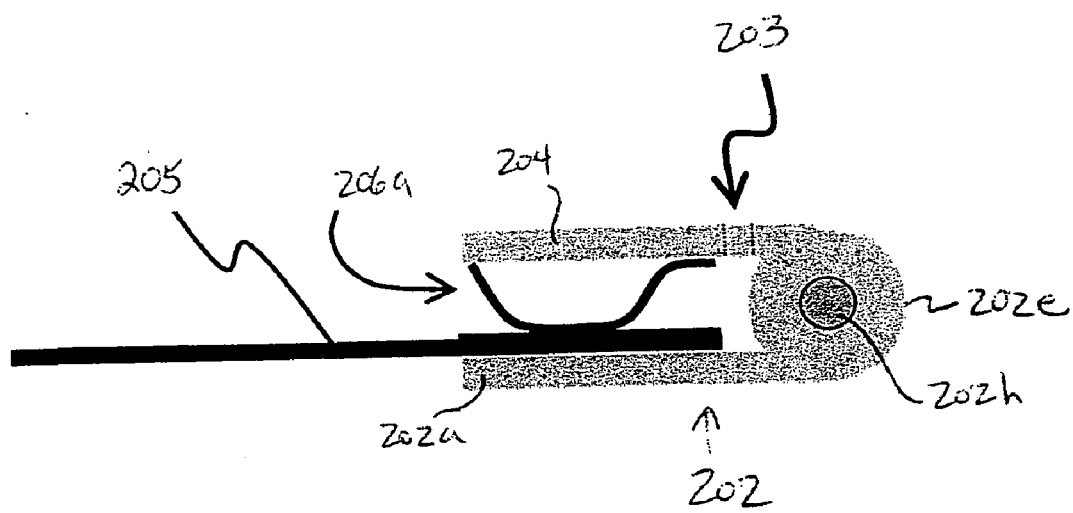
FIG. 33A is a side view of an embodiment of the slide holder clip of FIG. 33 in combination with a slide.

Referring to FIG. 33a, a slide 205 may be inserted between the arms 202a and the spring clip arms 206a (FIG. 33a), after which insertion the slide 205 will be snugly held within the slide holder clip 69. In certain embodiments, the shape of the arms 202a and the spring clip arms 206a provide for a small free pivoting motion of a slide 205 that is retained within the slide holder clip 69, the pivot point being just below the bow-shaped bends in the spring clip arms 206a, which are the main contact zones between the spring clip arms 206a and the slide 205. This free pivoting motion of the retained slide 205 permits the slide to precisely conform to the plane of the top surface of a respective temperature control member 64 within the non-moveable portion 100b of a drawer assembly 100. The ability to pivot into position in this fashion allows the slide to rest properly upon the temperature control member and thus substantially prevents the slide from being exposed to undesirable temperature gradients during a staining protocol.

The rear flange pivot portion 202e of the slide holder clip 69 (FIG. 33) has a hole 202h passing therethrough for mounting onto a support rod (not shown) that passes through corresponding holes in the rear portion of a slide rack. The entire slide holder clip 69 is able to rotate about the support bar passing through holes 202h so as to assume one of many mechanically stable positions including a horizontal position as shown in FIG. 33 (corresponding to slides 7 in FIG. 24 and FIGS. 27-28) and a vertical position (e.g., see slides 7v FIG. 24 and FIGS. 27-28). One or more detents 202d in the flange pivot portion 202e can assure that the slide holder clip 69 position will be held mechanically stable in at least the two aforementioned positions.

In certain embodiments, as illustrated in FIG. 33, the flange pivot portion 202e can define a cavity 202f. The cavity 202f can be formed by a number of processes, including the use of a counterbore. In certain embodiments, a wave spring (not shown) can be placed within the cavity 202f. The wave spring can facilitate the rotation of the slide holder clip 69 with respect to the support rod (not shown) that passes through the holes 202h. In this manner, a push tool 38 (see, e.g., FIG. 7A) can rotate the slide holder clip 69 by using a small amount of force.

The rotational motion of the slide holder clip 69 between two stable positions (e.g., vertical and horizontal) may, for example, be actuated by a push tool 38 (FIG. 7A), comprising an automated vertically moveable pin or bar (not shown) mounted on robotic head 22 that may access surfaces of slide holder clip 69 through access holes 67 in the slide rack 61 (FIG. 27) within which the slide holder clip 69 is housed. Two access holes are associated with each slide holder clip. When the slide 205 is held in a horizontal position, insertion of the push tool through the front-most access hole of each pair will cause the push tool to contact a top surface of retainer 204 (FIG. 33) such that further downward motion of the push tool against said surface will cause the slide holder clip 69 to lock into its vertical position. When the slide 205 is held in a vertical position, insertion of the push tool through the rearmost access hole of each pair will cause the push tool to contact the ledge portion 202p of the lower body member 202 (FIG. 33), the ledge facing upward in this configuration, and further downward motion of the push tool against the ledge 202p will cause the slide holder clip 69 to lock into its horizontal position. In certain embodiments, the ledge portion 202p can comprise one or more angles (not shown) to facilitate rotation of the slide holder clip 69 by the push tool.

In certain embodiments, as illustrated in FIG. 33, the slide holder clip 69 can comprise a channel 202q. The channel 202q can, in certain embodiments, be generally U-shaped in cross section. In certain embodiments, the channel 202q can locate under the edges of a slide (not shown) that is retained by the slide holder clip 69. In this manner, in certain embodiments, the channel 202q can capture various excess fluids that may run off the edges of the slide.

In further embodiments, a sample may be mounted in an apparatus of the invention as described in PCT/DK2004/000179, filed on Mar. 18, 2004, published on Sep. 30, 2004 as WO 2004/083824, or provisional application 60/682,046 filed on May 18, 2005, the disclosures of both of which are incorporated herein by reference.

In one embodiment, the slide rack is in a lowered position when the drawer 100 is loaded with one or more slides 7 and also during the staining process. After the slides 7 have been loaded, the slides 7 may be pivoted to a vertical position 7v and then the slide rack 61 is lowered by the slide elevator 63, such that the vertically disposed slides 7v are immersed into the underlying processing tank 101. The drawer assembly is also shown in the FIGS. 25, 26 and 28. The slide elevator 63 may be adapted to agitate the slides 7v while they are immersed in the tank fluid.

Figure 31:
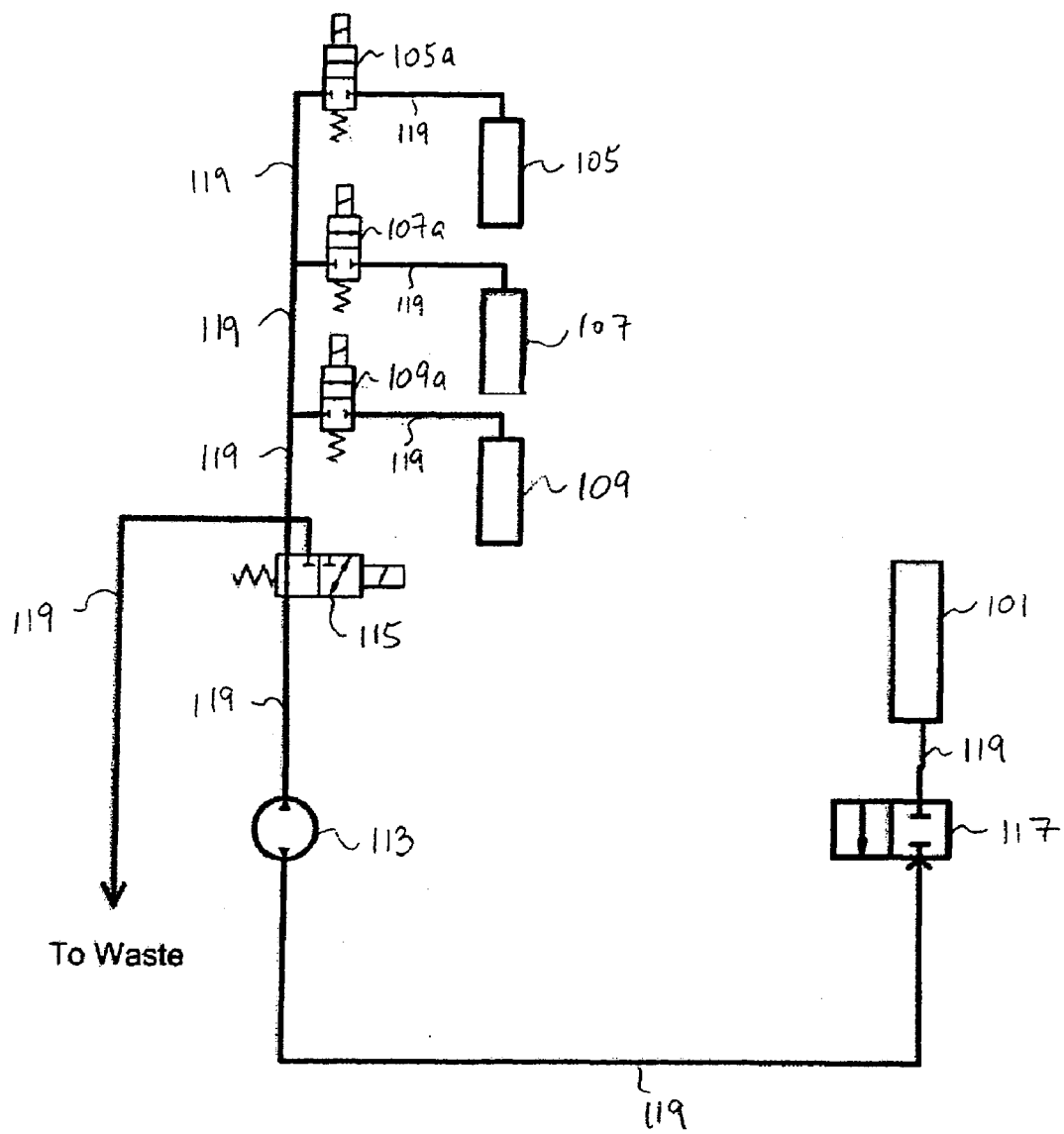
FIG. 31 is an example fluidic diagram of the handling of processing liquid for the processing tank.

Turning to FIG. 31, the processing tank 101 may be filled with a predetermined amount of a processing fluid, for instance, supplied from a supply of bulk fluid reservoir. Such reservoir may be supplied to the processing tank 101 such as through supply lines 119. The supply lines may consist of any suitable conduits and/or connection types for transferring processing fluids to and from the staining apparatus 1 including those sufficient, such as for purging functions. In the shown embodiment, three bulk fluid supplies (bulk fluid one 105, bulk fluid two 107, and bulk fluid three 109) are depicted in connection with the processing tank 101 via supply lines 119. (While three bulk fluid supplies 105, 107, and 109 are shown in this embodiment, it should be understood that any number of bulk fluid supplies, as deemed necessary, may be utilized to provide processing fluids to the processing tank 101.) Bulk fluid supplies 105, 107 and 109 may be connected to respective selector valves 105a, 107a, and 109a which may be independently enabled to regulate/control supply of processing fluid from respective bulk fluid supplies 105, 107, 109. In some embodiments, the selector valves 105a, 107a, and 109a may be controlled, such as via a control system including associated electronics, control protocols, and/or associated software algorithms in connection with the staining apparatus 1 for supplying bulk fluids to the processing tank 101.

A pumping system such as a pneumatic pumping system having a reversible gear pump 113 may be utilized to control the fluid transfer to and from the processing tank 101. Selector valve 115 may be coupled to the supply line 119 prior to the reversible gear pump 113 and after the supply of bulk fluid. An additional supply line 119 may be connected to the selector valve 115 and be utilized to dispose of waste fluids, for example, being fed to a waste receptacle. Another control valve 117, such as one associated with the processing tank 101, may be coupled along the supply line 119 between the reversible gear pump 113 and the processing tank 101.

Thus, in operation, the reversible gear pump 113 may be enabled to direct flow of processing fluids from the supply of a bulk fluid ultimately to the processing tank 101. Control of which bulk fluids are fed through the supply lines 119 and ultimately to the processing tank 101 is based upon, at least in part, which selector valves 105a, 107a, and 109a are enabled.

Additionally, the reversible gear pump may be enabled to direct flow of processing fluids in an opposite direction from the processing tank 101 such as to a waste receptacle. In this embodiment, selector valve 115 may be enabled to receive discarded processing fluid, such as from processing tank 101, and direct the fluid into a supply line 119 towards a waste receptacle. It should be further appreciated, that in some embodiments, a combination of valves 105a, 107a, 109a, 115, 117 may be enabled and/or disabled to perform a variety of functions such as supplying processing fluid to the processing tank 101, removing processing fluid from the processing tank 101, clearing operations or supply line purging functions, and/or emptying processing fluids from fluid bulk supplies 105, 107 and 109.

In one embodiment, a total of eight drawers may be provided. Accordingly, eight processing tanks may be provided in the apparatus. In one embodiment, each processing tank 101 may accommodate up to eight immersed slides 7v at one time. A primary function of the processing tank may include heating the fluid in the tank up from ambient temperature to a predetermined temperature, in a certain amount of time, e.g. 15 minutes and maintain the predetermined temperature (e.g. up to about 120° C.) without any sign of boiling for a pre-treatment processing time (e.g. 10 to 20 minutes after the slides have been lowered into the processing tank). In one embodiment, temperature is in the interval from about 40° C. to about 120° C., as determined by the requested treatment. Very often the temperature may be in the interval from 80° C. to 100° C., such as from 9A5° C. to 9A8° C. For some treatments the interval can be from 110° C. to 130° C. and even up to about 150° C.

After this process time is passed, the heat is turned off and a cool-down period may be allowed whereupon the slides 7v may be removed by raising the slide rack 61 and thereby lifting the vertical slides 7v out of the processing tank 101. The tank 101 may be used for deparaffinization, re-hydration and target retrieval, including heat-induced target retrieval. These processes are performed onboard the apparatus with the slides in a vertical orientation, immersed in individual tanks that can be filled with and emptied of various required fluids. For the target retrieval process, the fluid level in the tank may raise onto the label on the slide. The heating member may be adapted to heat up and maintain a temperature of approximately 9A5° C. for a period of up to 40 to 60 minutes.

The pre-treatment process, carried out in the processing tank, may involve immersing the slides in a series of fluids for short periods of time, e.g. 5 to 10 minutes. The process of deparaffinization is intended to first remove from the tissue sample the paraffin in which it was mounted, and then remove the paraffin solvent, and then through a series of reagents progressively re-hydrate the sample. The process of target retrieval may involve immersing the slides in a tank of heated buffer for incubation periods of up to 20 to 60 minutes. During this time the processing tank temperature may be maintained at a temperature, such as 9A5° C.±2° C. at sea level, when measured from top to bottom of the slide. Cooling of the fluid may be performed, and slides may be allowed to remain in the fluid or in a water bath during cooling.

An automated sample processing system in accordance with embodiments of the present invention may control one or both of the staining protocol as well as the pre-treatment, if any, administered to each slide, depending upon slide-specific information entered by the user. If the sample on a particular slide requires only deparaffinization, but not target retrieval, then the following sequence of steps, for example, may be performed:

flip slide to vertical position;
    lower slide into processing tank;
    supply processing tank with deparaffinization fluids, in sequence according to deparaffinization procedure;
    maintain slide in deparaffinization fluids for required time;
    drain processing tank;
    repeat steps 3-5 for all fluids required in deparaffinization procedure;
    supply water rinse to processing tank;
    drain rinse water from processing tank;
    raise slide out of processing tank;
    flip slide to horizontal position;
    run desired staining protocol for sample on slide, if any slides in the rack are undergoing target retrieval, rather than begin staining, the other slides will be kept at a specific temperature and will be kept hydrated by period application of a buffer via the robot and the adaptive scheduler.

If the sample requires only target retrieval, but not deparaffinization, then the following sequence of steps, for example, may be performed:

flip slide to vertical position;
    lower slide into processing tank;
    fill processing tank with buffer solution for target retrieval;
    heat buffer solution and immersed slide at desired temperature for desired time, according to target retrieval procedure;
    drain processing tank;
    supply water rinse to processing tank;
    drain rinse water from processing tank;
    raise slide out of processing tank;
    flip slide to horizontal position;
    run desired staining protocol for sample on slide.

If the sample requires both deparaffinization and target retrieval, then the following sequence of steps may, for example, be performed:

flip slide to vertical position;
    lower slide into processing tank;
    supply processing tank with deparaffinization fluids, in sequence according to deparaffinization procedure;
    maintain slide in deparaffinization fluid for required time;

drain processing tank;
repeat steps 3-5 for all fluids required in deparaffinization procedure;
supply water rinse to processing tank;
drain rinse water from processing tank;
fill processing tank with buffer solution for target retrieval;
heat buffer solution and immersed slide at desired temperature for desired time, according to target retrieval procedure;
drain processing tank;
raise slide out of processing tank;
flip slide to horizontal position;
run desired staining protocol for sample on slide.

As shown in, for instance, FIGS. 29 and 30, the processing tank 101 may be elongated with an opening slot 102 through which the slides 7v may be inserted. This results in a relative small tank volume, which in turn allows for relatively rapid heating of the fluid in the tank and/or relatively low power consumption for heating up and maintaining the temperature of the fluid in the tank. In one embodiment, the tank 101 is filled and drained via a fluid connection tube 103 and the heating member 104 may be located in the lower section of the tank. The tank 101 may moreover be provided with insulating sidewall members on both sides to accelerate the heating thereby decreasing the heating times. The tank 101 may also be provided with sensor means (not shown) for registering the fluid level in the tank and a sensor for registering the temperature of the fluid, and feeding these data to the control system of the apparatus.

The pre-treatment fluids or reagents may be stored in a number of individual containers, where some containers store fluids that are dedicated for deparaffinization, some for target retrieval and containers with 100% alcohol, 9A5% alcohol, distilled water and buffers or other desired fluids in accordance with the protocols. The containers may be advantageously provided with different volumes corresponding to the required amounts of the specific fluids for the performance of the pre-treatment processes on the apparatus.

Fluids may be transferred in both directions between any container and any tank. In one embodiment, the operational sequence of the fluid transfers is determined by the control system of the apparatus. The deparaffinization reagents may be reused and periodically cycled from clean to dirty. Used dirty deparaffinization fluids and tank rinse fluids may be discarded by the user or by the control system as hazardous waste. Target retrieval buffer and water are labeled "single use" fluids in the control system and transferred to waste after use.

The method according to the invention may include temporary storage of at least one biological sample on a sample carrier 7, such as a slide, in an appropriate liquid in the processing tank, for instance, after finishing the requested treatment until the biological sample on the slide can be removed for further off-instrument processing. Typically, this use of the processing tank may be specifically advantageous in relation to an overnight staining, e.g. completed in the middle of the night.

Figure 35:
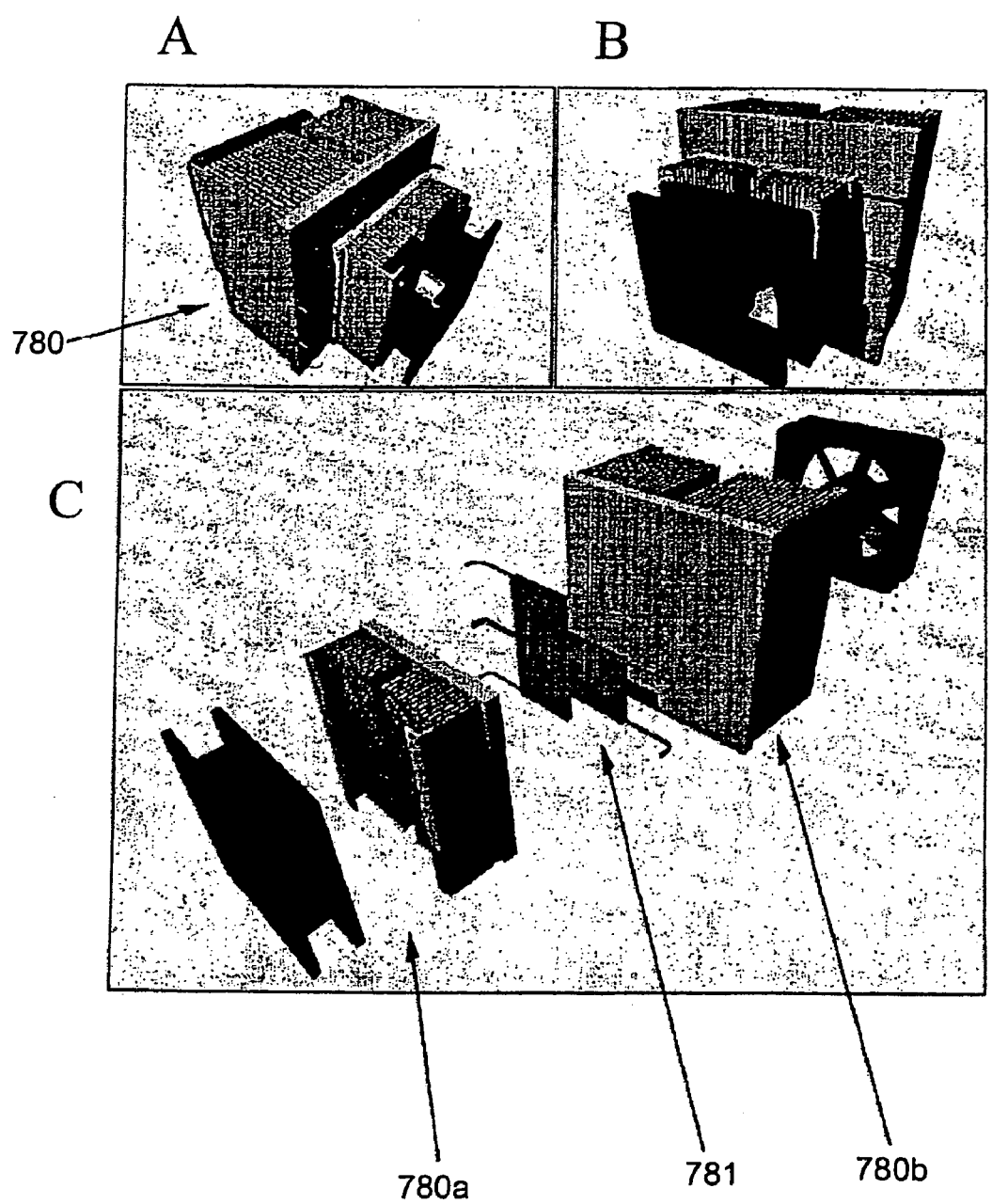
FIGS. 35A-C are additional views of examples of temperature control aspects of one embodiment of the invention.

The apparatus, such as a stainer, may comprise a temperature controller for temperature control of samples, reagents, and/or processing environments such as a processing tank or the air inside a stainer. In one embodiment the temperature controller may function as a means for controlling the temperature. Examples include, thermoelectric or Peltier devices, air, gas, and liquid cooling including cooling where heated and cooled fluids and/or gases are controlled in combination to achieve a desired temperature, resistive heaters, ambient heating, radiant heaters, adiabatic cooling, and adiabatic heating. Configurations of the temperature regulation system may include a Peltier device or Peltier temperature control, and in configurations such as shown in FIG. 35, a heat sink/fan pair 780a on the inside of the system's temperature-controlled interior volume. The other heat sink/fan of the pair 780b may be on the outside of the controlled volume, where it is exposed to the ambient environment of the laboratory. One or more thermoelectric devices (TED's) 781 perhaps including the electrical junctions themselves may be located on the boundary between the interior and exterior. The TED or TED's may generate a hot portion and a cold portion and may aid in moving heat into or out of the desired location. The "hot" portion may be configured to distribute heat from the exterior of the controlled interior volume. If the temperature of the "hot" portion of the TED is controlled to maintain a low temperature, such as with a controlled paired heat sink/fan, the corresponding "cold" portion of the TED, may be configured within the controlled interior volume, may be colder by a corresponding amount, and may act in conjunction with a paired heat sink/fan as a controlled refrigerator, and may even actively reduce the temperature of the interior volume, or may achieve protocol tolerances as further described below. Such an item may serve as a temperature reduction element for various locations or purposes as described below.

As mentioned above, the internal temperature of the system may be controlled by a scheduler. Some applications may provide temperatures at 18° C.+6° C.; in other embodiments the internal ambient temperature may be maintained at about 24° C.+ an incremental range, such as a non-integer incremental range. One temperature regulation system of the present invention may comprise one or more heat pumps, and in some embodiments two thermoelectric heat pumps (heat pump 780 shown in FIGS. 35A and 35C). The temperature regulation system may feature each heat pump module having a heat sink and fan on either side of the TED.

Figure 34A:
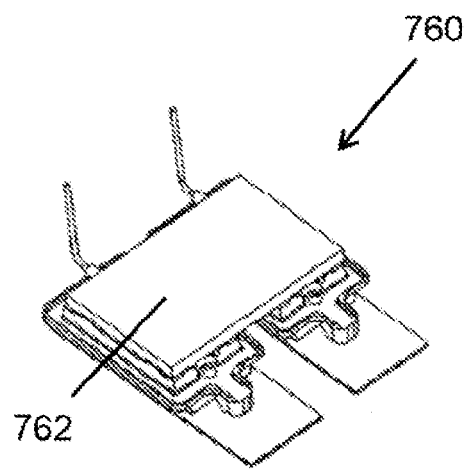
FIGS. 34A-B are views of examples of temperature control aspects of one embodiment of the invention.
Figure 34B:
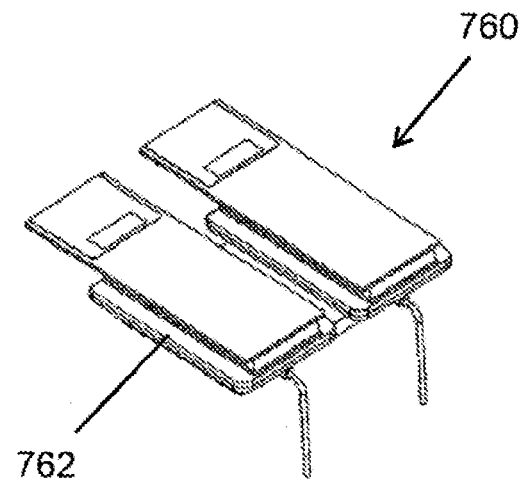
Figure 36:
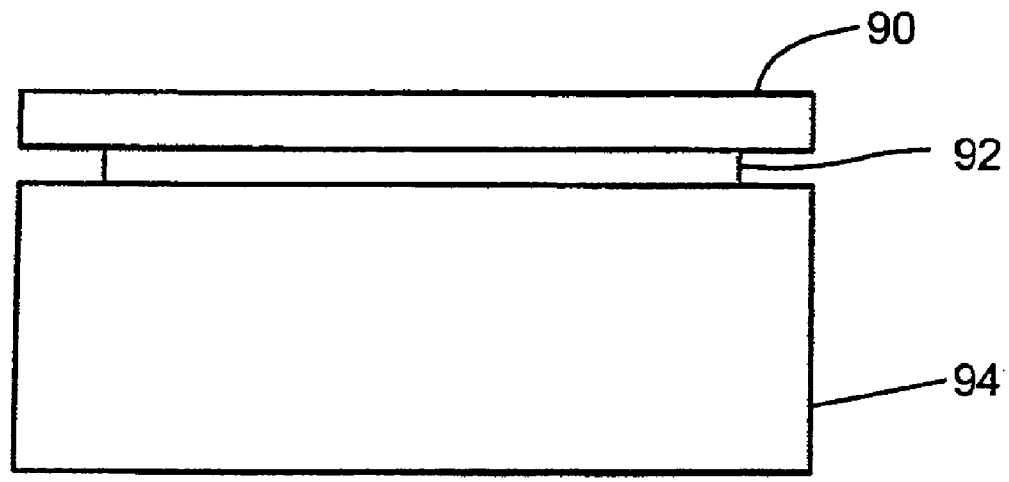
FIG. 36 is a block diagram of a temperature regulation design according to an embodiment of the invention.

Embodiments of the invention may comprise a means for sample temperature control such as a sample carrier temperature regulation systems. In some embodiments a sample carrier temperature regulation system is configurable with one or a plurality of sample carrier supports, and corresponding methods of sample carrier temperature regulation. Some embodiments may comprise a Peltier grid, such as grid 760 shown in FIG. 34, that may be used as a component of or as a slide temperature control member 64 (FIGS. 24, 26), to heat or cool a slide during processing of the samples. Thermal elements 762 may heat the slides, in some embodiments from ambient to about 120° C. in about 3 minutes. Sample carrier temperature regulation systems may comprise, in some embodiments, one or more sample carrier supports such as a slide support plate 9A0 as shown in FIG. 36, configured with temperature regulation elements, such as one or more temperature regulation elements, and in some embodiments a laminated thermal element 9A2 as shown in FIG. 36, and a cold plate 9A4 shown in FIG. 36.

In one embodiment, the sample carrier temperature regulation system may reach target temperature even when ambient temperature is about or greater than target temperature, or about or less than target temperature.

Figure 37A:
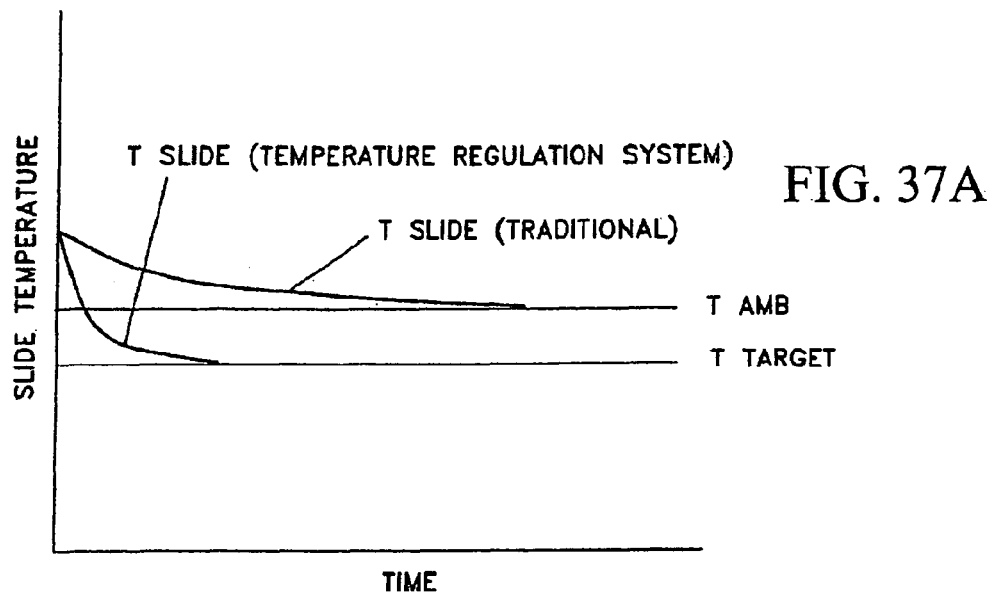
FIG. 37A is a comparison chart of exemplary temperature changes for an embodiment of the present invention and potential temperature changes of a traditional system in relation to a protocol temperature target, wherein ambient system and sample carrier temperatures may be initially above the protocol temperature target.
Figure 37B:
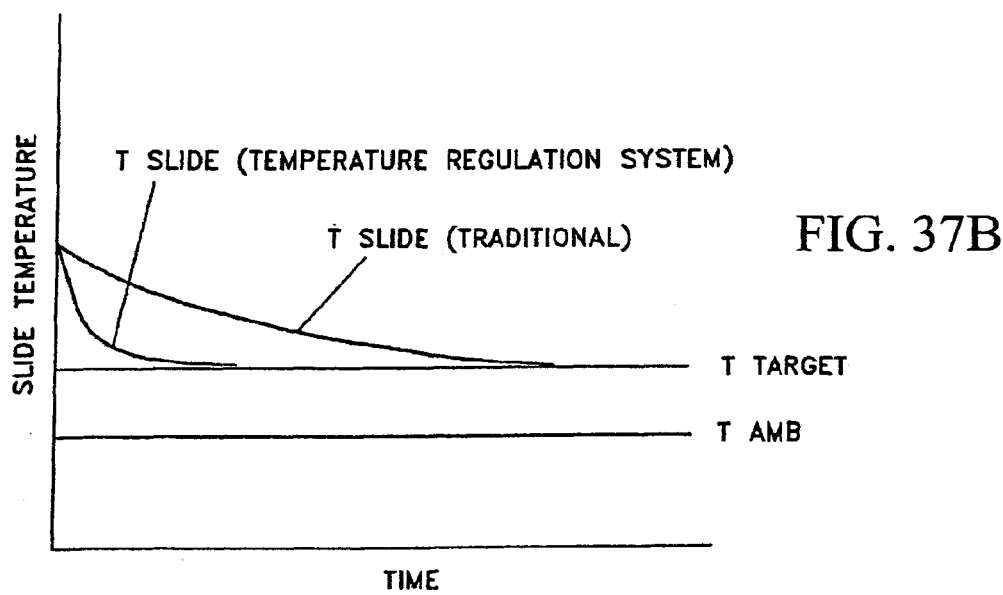
FIG. 37B is a comparison chart of exemplary temperature changes for an embodiment of the present invention and potential temperature changes of a traditional system in relation to a protocol temperature target, wherein sample carrier temperature may be initially above the protocol temperature target and ambient system temperature may be below the protocol temperature target.

The various embodiments of the disclosed temperature regulation system and the sample processing control system feature the capability to control system temperature, and in some embodiments, slide temperature and reagent temperature. The combination of features may allow active heating and cooling of sample carriers, and in some embodiments potentially utilizing a controlled Peltier device or temperature control, a conductive device or temperature control, or a combination of temperature control features. One example of a temperature control sequence may allow a controlled (e.g., adjustment or maintenance within a particular set parameters such as rate of change or the like) or even accelerated increase and/or decrease in slide temperature, perhaps including independently a ramping up and/or down of the temperature. The system may be considered as including a controlled temperature element or a controlled active temperature element, such as a controlled active temperature reduction element or the like. Another example of a controlled temperature sequence is shown in FIGS. 37A and 37B. These figures generally illustrate and compare temperature changes of the present invention and a type of traditional system. They illustrate target temperature tolerance, the time necessary to reach values, and ambient temperature aspects. In some embodiments, energy may be delivered at the same or about the same rate by the temperature regulation system as a traditional system. Energy may also, however, be removed or added, and perhaps even removed or added faster or slower than a traditional system, as traditional systems may dissipate energy to the ambient. A shorter or longer period for temperature effects, such as sample carrier cooling, may result. Active temperature regulation, in some embodiments heating and cooling, may be provided in some embodiments to provide such results.

In some embodiments, when a temperature disturbance greater than the target temperature occurs, such as by the effect of warm sample carriers, the present invention may utilize a conductive temperature regulation system, such as a substrate temperature regulation device, so as to dissipate excess energy, as previously described.

In one embodiment, the temperature may be controlled within the required temperature tolerance for the sequence and controlled to maintain lesser values of rates of temperature change (dT/dt) during the sequence. The temperature range for a slide processed in accordance with conventional processing may exhibit greater values of rates of temperature change and may have temperatures beyond required tolerances for a significant portion of a sequence. As a result, the uncontrolled temperatures may be detrimental to the outcome for a protocol, such as the staining example previously described in relation to traditional technologies. An excessive low or high ambient temperature, and particularly an uncontrolled temperature, may cause a slower rate of temperature change and therefore may require a longer time to reach a desired temperature value as may be required by the protocol. The software may monitor and record individual sample temperatures throughout the staining process to ensure conformance with process temperature specifications and marks the database record of any sample whose temperature falls outside of specifications during processing.

Figure 38:
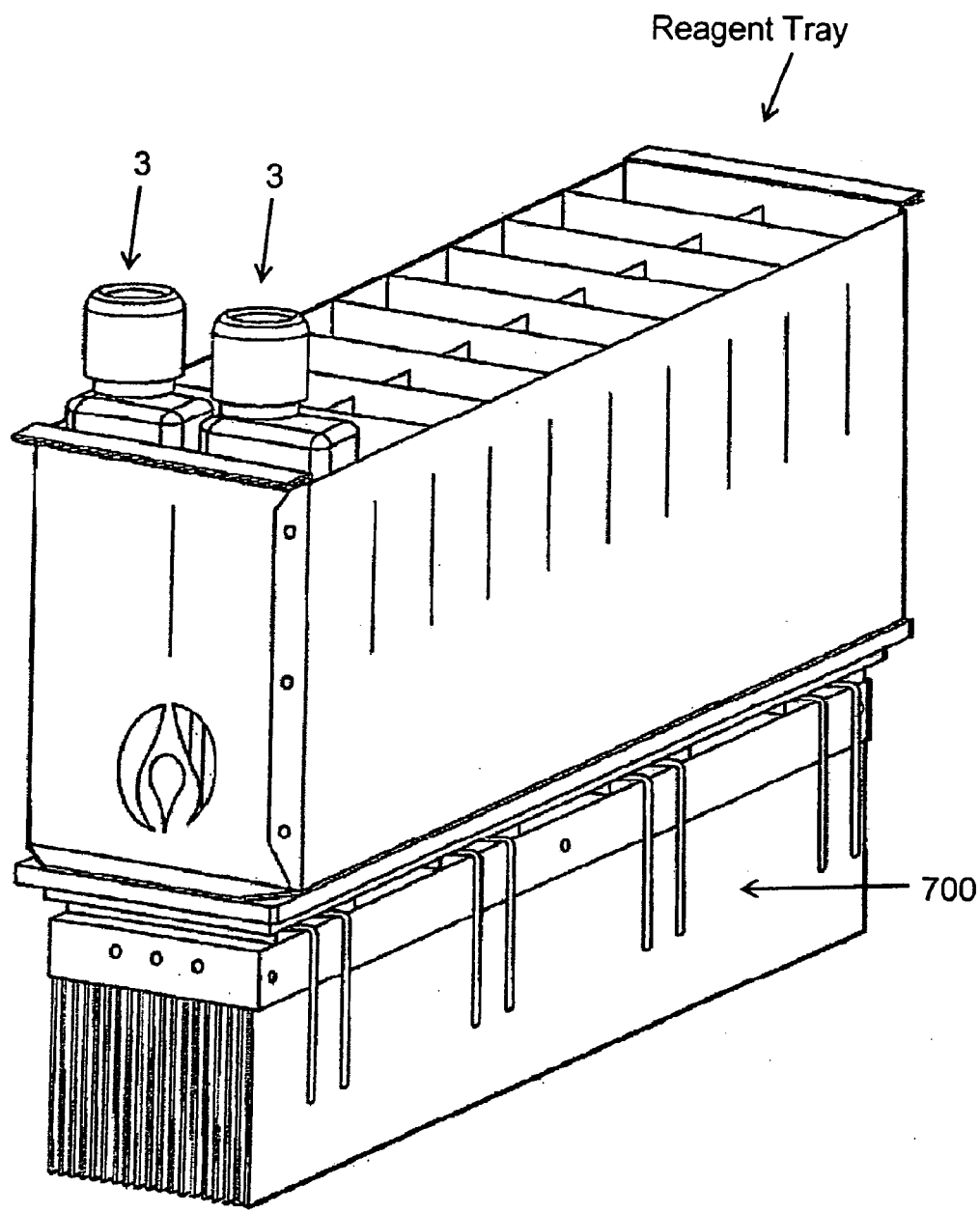
FIG. 38 is an isometric perspective view of an example of reagent container temperature control aspects of an embodiment of the invention.

The various embodiments of the disclosed temperature regulation system may feature the capability of controlling reagent temperature alone or in addition to sample temperature. One embodiment of a reagent temperature regulation system is shown in FIG. 38 and may include a conduction temperature regulation system. A reagent temperature regulation system may have conductive regulation elements 700 perhaps mounted below the reagent tray. The conductive regulation elements may feature thermoelectric regulation features such as Peltier-type temperature regulation. Naturally, a sensing element may be provided as part of arm 20 or in another sample processing configuration, may be incorporated to sense temperature, perhaps instantaneously. This may assist in maintaining temperature tolerances and in controlling rates of temperature change. Photodiode devices, electric conductivity devices, IR sensors, sensors acting through septa of a container, or other sensors may be included to sense values such as reagent containers or slides collectively or individually.

Temperature control of the temperature regulation system may be provided to take advantage of the active heating and cooling capability of the above described temperature regulation system. Accordingly, in some embodiments temperature control may be provided to at least actively regulate temperature within protocol tolerances. The temperature regulation system of the present invention previously described may be accordingly configured to increase or reduce temperature, and in some embodiments actively increase or reduce temperature. The scheduler may provide a corresponding controlled increase or reduction of temperature, and in some embodiments actively controlled increase or reduction of temperature. It may also reduce the rate of an increase or decrease in temperature change (as compared to the often-used maximum power type of approach) such as by intermittently powering or lower powering the device or the like and may thus provide a reduced rate of temperature change element. Corresponding methods of the invention may comprise methods of temperature control of sample processing systems, comprising the step of regulating temperature within protocol tolerances, and in some embodiments, actively regulating temperature. Further methods of temperature control of sample processing systems are disclosed comprising one or more steps of actively increasing temperature, actively reducing temperature, or a combination of such steps. Additional capabilities of the staining apparatus 1 may include hardware and software configurations to provide additional features for processing samples as described here, and in more detail in other sections of the specification. These features may include: flexible software with multiple-language capability; slide programming with capability to create and edit custom staining protocols; tracking and storing of a variety of data; generation of case, reagent, and real-time operation data reports; tracking reagent usage and instrument maintenance; configurable to link to laboratory equipment such as Laboratory Information Management Systems (LIMS) or Laboratory Information Systems (LIS); allowable for multiple-stainer management through network connectivity; configurable to enable the administration and monitoring of several staining apparatus 1 instruments from one or more "manager" computers with no one-to-one correspondence between managers and instruments.

In one embodiment, the apparatus may include means to communicate with a network, including bi-directional communication, which may provide a channel for timely notification and manual or automatic intervention. For example, digital and analog modems, fax, wireless and cellular technology, including text messaging and e-mail, satellite communications, audio, infrared, ultrasonic and fiber optic. Embodiments of the invention may also provide Local Area Network (LAN) connections to allow staining apparatus 1 to communicate with other devices, including, for examples, remote devices, other staining apparatuses, other laboratory instruments, laboratory and third party information systems, and computers. Network connections allow staining apparatus 1 to send and receive status information including information about slides, process-status, protocols, reagents, fluids, diagnostics and other information that may be required by remote users. In some embodiments the staining apparatus 1 may also include an embedded computing system with processors, memory, hard drives, graphics and other electronic sub-systems that allow software, firmware and other program code to be run and executed.

Thus, in some embodiments, data may be retrieved electronically from another computer system, over a network, from a Laboratory Information Management System ("LIMS"), or from another laboratory instrument. Patient data may include a patient identifier, sample related data, other identifying information and may include information regarding a medical provider or other services to which results data may be sent. Slide data may include a slide identifier and a protocol associated with the slide. In some embodiments, slide data may be printed on a label in a machine readable format such as an Infoglyph™ and applied to a slide containing the sample.

Figure 39:
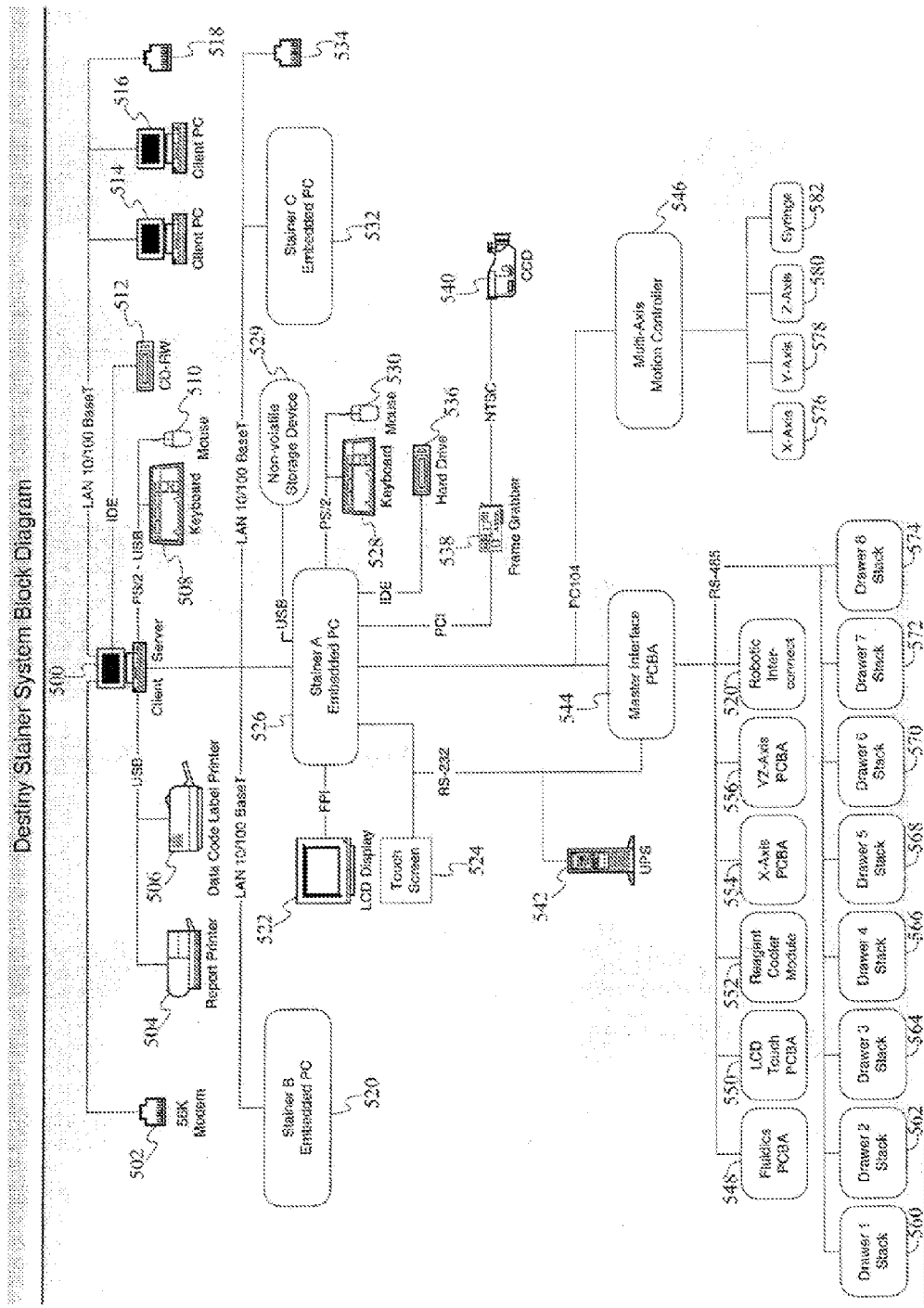
FIG. 39 is an illustration of a stainer configured to a networked system in accordance with one embodiment of the invention.
Figure 40:
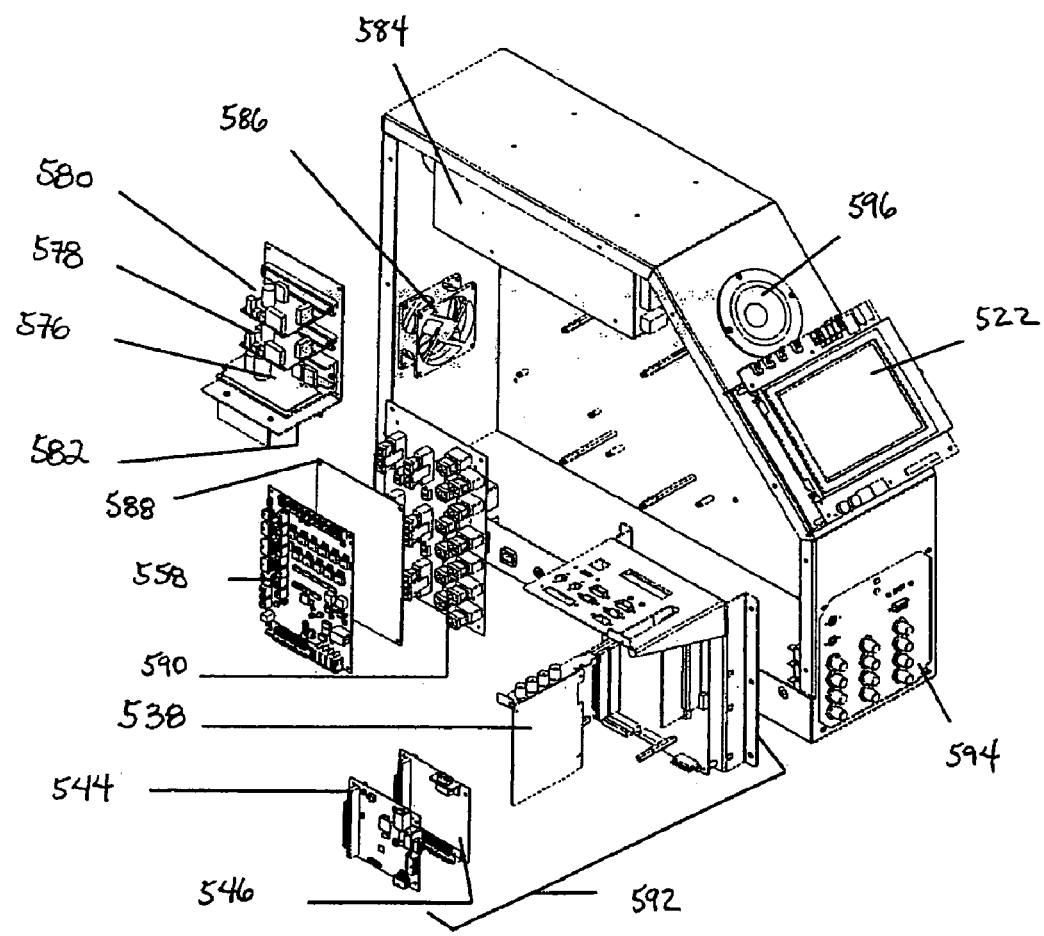
FIG. 40 is an exploded view of an embodiment of an electronics assembly sub-system of a stainer assembly.
Figure 41:
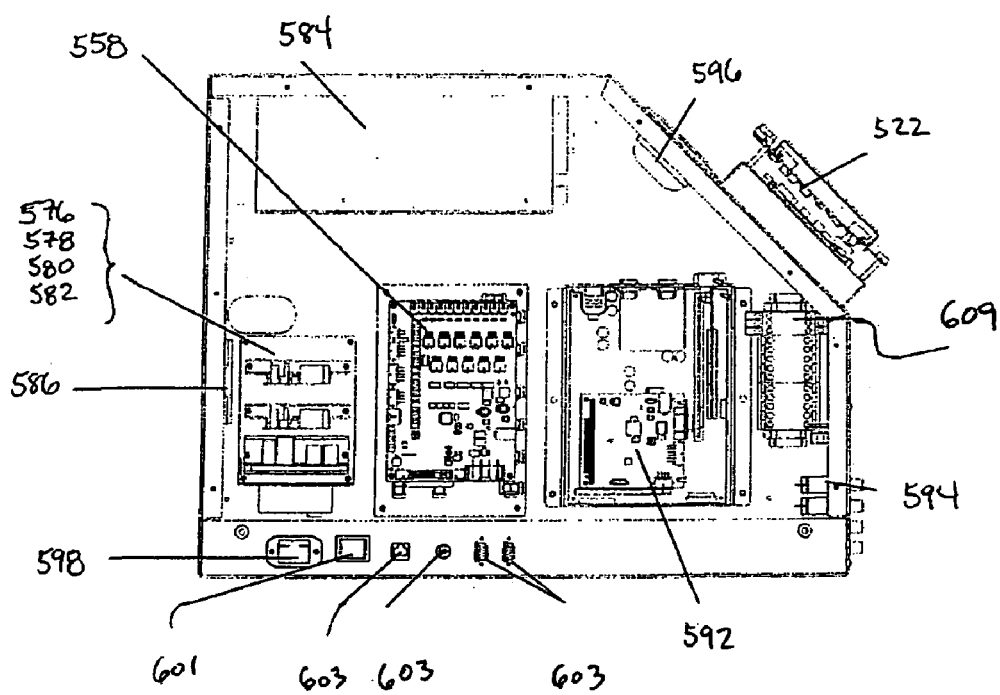
FIG. 41 is a side view of an embodiment of an electronics assembly sub-system of a stainer assembly.

As shown in FIG. 39, control of the processing samples may be accomplished with a distributed electronic architecture which includes components that may process or operate substantially in parallel with each other. Distributed parallel processing of some low level functions, such as drawer monitoring or control, may enhance the continuous workflow of the staining system by facilitating timely performance of processing tasks and by permitting continued operation of functioning assemblies simultaneous with isolation of assemblies that may be experiencing a malfunction. The sample processing system may include a sample processing system manager 500, such as a computer server in communication with one or more staining apparatuses 520, 526, 532. One computer may perform both client and server functions or such functions may be partitioned. Staining apparatus 526 is depicted having an embedded PC 592 which is further connected to a master interface printed circuit board assembly (PCBA) 544. FIGS. 40-41 show additional components of an embodiment of the electronics assembly subsystem of the staining apparatus 526. An AC power supply 584 (220 VAC) may be mounted to the subsystem. The power supply 584 changes AC power to +24, +12, and +5 VDC. In some embodiments, all PCBAs in the staining apparatus 526 use 24 VDC and 12 VDC except the embedded PC board which uses 5 VDC directly from the power supply and receives power-delivery-status signals. The power supply module may consist of one AC input module, a 5 VDC module and two 12 VDC modules wired together in parallel, and two 24 VDC modules wired in parallel. The grounds may be tied together with jumpers at the power supply module.

The embedded PC assembly may be powered by 5 and 12 VDC. In one embodiment, control software resides on the embedded PC. When an operator turns on the staining apparatus 526, the embedded PC boots up and may check the server computer 500 for software updates. If necessary, the updates may be downloaded. Once the embedded PC is booted up, it allows power to be sent to the VDC modules on the instrument. This also helps to ensure that the staining apparatus subsystems will not operate accidentally. Thus, the embedded PC assembly may consist of a CPU, such as a 1.22 GHz Pentium II processor, and a conventional storage apparatus, such as a hard drive 536, coupled thereto such as via IDE connection. A video graphics card, such as a frame grabber card 538, may also be connected to the embedded PC and further coupled to a video device such as a camera or optical lens 540. The Frame Grabber Card 538 converts video signal, such as from the Robotic Interconnect PCBA 558, to a digital signal so the embedded PC can read it. Additional input devices, such as a keyboard 528 and mouse 530, for examples, may also be connected to the embedded PC to input information. A non-volatile storage device 529, such as a USB flash drive module for non-volatile storage of critical instrument-specific settings, may be further connected to the embedded PC such as via USB connection or other suitable connection type.

Converted power may be routed from the power supply module 584 to the power distribution PCBA 590 in order to distribute all DC power to the instrument subsystems of the staining apparatus 526. The power distribution PCBA 590 sends approximately 5V from the main power supply to the embedded PC, which may be the only PCBA in the system that gets 5 VDC directly from the power supply 584. Prior to distributing power throughout the system, the power distribution PCBA 590 may run all VDC power through separate circuit breakers. Each reagent and stainer drawer may have a dedicated circuit breaker, for example, located in the circuit breaker assembly 594.

The master interface PCBA 544 may be integrated within the embedded PC stack 592. It may be wired to the power supply 584 and continuously monitor the status of the power supply 584. The master interface PCBA 544 may operate as an intermediary between system PCBAs 548-574 and the embedded PC of the staining apparatus 526. System PCBAs 548-574 may be connected to the master interface PCBA 544 in order to communicate with the embedded PC through the master interface PCBA 544. In one embodiment, the aforementioned connection may utilize RS-485 busses to allow communication with the embedded PC. Additionally, the master interface PCBA 544 may have a capability to shut off the VDC modules that are controlled from the software on the embedded PC. This protocol may insure that the stainer subsystems will not operate accidentally.

The multi-axis motion controller PCBA 546 may also be located on the PC stack 592 and may serve to control motors associated with the robot. The multi-axis motion controller PCBA 546 may be configured to work with the robotic interconnect PCBA 558. In one embodiment, the multi-axis motion controller PCBA may be connected with the robotic interconnect PCBA 558 via a connection such as a 68-pin SCSI cable. Thus, the multi-axis motion controller PCBA 546 may send a signal through the robotic interconnect PCBA 558 to direct step the motor drivers X (576), Y (578), Z (580), and the syringe pump (582) step or motor driver. The robotic-controller step pulse goes to the step or motor drivers which in turn send current into step coils and cause the motors to move one step pulse. Signaling apparatus such as encoders on the shafts of the step or motors may send signals back to the multi-axis motion controller PCBA 546 which in turn may analyze the encoded signals.

The robotic interconnect PCBA 558 operates to break out signals from the multi-axis motion controller PCBA 546 to the step or motor drivers and distributes the signals. The X-cable track connects the robotic interface PCBA 558 with the X-interconnect PCBA 554. The YZ cable track connects the X-interconnect PCBA 554 to the YZ PCBA 556 that controls the robot.

The robotic interconnect PCBA 558 may also contain valve drivers that control additional system valves such as including the front door interlock 609 and pneumatic valves to the robot. The robotic interface PCBA 558 may also decode video signal from the CCD camera 540 on the lead Z-head. The video signal may be directed from the camera 540 to the differential video driver on the YZ PCBA 556 which changes the signal to a differential signal and sends it back through the robot track to the robotic interconnect PCBA 558 with a differential signal decoded and then sent to the frame grabber PCBA 538. The frame grabber PCBA 538 converts video signal received from the robotic interconnect PCBA 558 to a digital signal so the embedded PC can read it.

The fan motor board 588 may control the electronics enclosure fan 586 and the upper-plenum fan that draws hot air through the top of the unit and out of the exhaust vent. It monitors tachometer output from the fans and sends information back to the embedded PC. The fan speeds may be controlled by software. The fan monitor board 588 also controls three circuits that power the drawer fans. One circuit pertains to fans on drawers 1-4, another pertains to fans on drawers 5-8, and one pertains to the reagent drawer fans. The electronics assembly sub-system may further comprise a power receptacle 598, on/off switch 601, and one or more communications ports 603 such as NIC receptacles or serial ports.

Turning to FIG. 39, an LCD display 522 may be linked to the embedded PC of the staining apparatus 526. In one embodiment, a flexible peripheral interface bus (FPI) is utilized to connect the LCD display 522 to the embedded PC. Likewise, a touch screen 524 or speaker 596 may also be connected to the embedded PC of the staining apparatus 526. The staining apparatus 526 may also receive backup power via an uninterrupted power source (UPS) 542. In one embodiment, the UPS 542 may be connected to the staining apparatus 526 via an RS-232 connection.

In one embodiment, to facilitate continuous workflow, the staining apparatus 526 provides a distributed controller which imparts a variety of functionality to each slide carrier or group of slide carriers such as the drawers depicted in the staining apparatus. Such functionality may include one or more actions, driven by PCBAs 548-558, for example performed upon one or more drawers, for example, drawers 560-574. In order to help facilitate independent functionality, PCBAs 548-558 each act as its own low level micro-controller.

As used herein, a distributed controller is an apparatus that distributes control functions to and from a plurality of controllers, for example, an apparatus that comprises a controller that communicates with at least one other controller that controls an element, such as temperature controllers, electromechanical valves, sensors, transducers, input and output means, pumps, indicators, mechanical locks, mechanical transporters, and motors, such as robotic motors. Another example is an apparatus that comprises a controller that communicates with at least one other controller that controls a group of elements such as a joint controller. In one embodiment, a controller that communicates with controllers that control at least one of the reagent holder, the biological sample holder, a temperature controller. A controller is for example, any circuit, electronics, hardware or software, such as a PCBA, that can controls an element. In one embodiment, the controller may function as a controller means.

Figure 47:
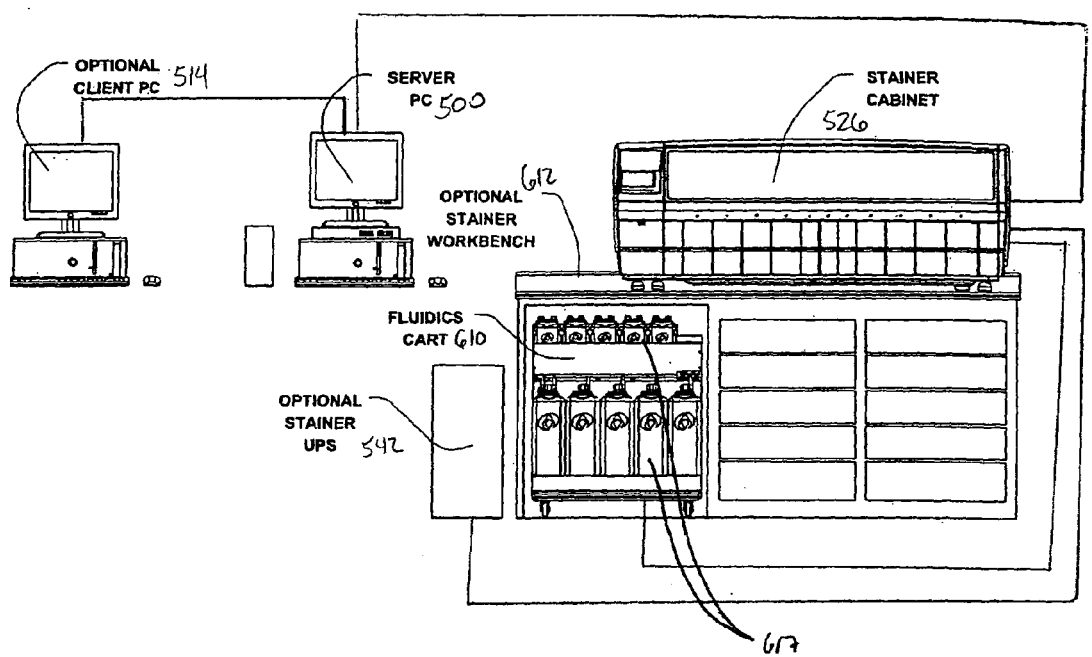
FIG. 47 illustrates an embodiment of a stainer in combination with a fluidics supply.

The fluidics PCBA 548 may provide control of a connected fluidics systems to the stainer assembly 1. As shown, for example, in FIG. 47, stainer assembly 526 may also include fluidics, Local Area Network ("LAN") and power connections 542, which includes controls and connections for fluidics, for networking and for power. As shown in FIG. 47, embodiments of stainer assembly 526 may include a fluidics subsystem with a fluidics cart 610 with labeled electronically readable containers 617 that store bulk fluids such as slide buffers, fluids for flushing conduits, probe cleaning fluids, de-ionized water etc. In some embodiments, fluids may be delivered to locations, such as processing tanks, within stainer assembly 526 at points in time when they may be needed, using conduits (not shown) from fluid containers 617 on fluidics cart 610. In some embodiments, multiple conduits may be provided for fluid delivery and the conduits allocated to fluids as needed, based on resource allocation and scheduling algorithms in accordance with treatment protocol-related constraints. In some embodiments, fluids drained from stainer assembly 526 may be held in a separate labeled fluidics container 617 in fluidics cart 610 for bio-hazardous material.

Each PCBA 548-558, having respective functionality, may be connected to the master interface PCBA 544 which monitors and controls the functionality of respective PCBAs 548-558. As described earlier, each drawer assembly (1-8) 100 may contain a respective drawer assembly electronics module 560-574 which acts as its own respective micro-controller to control all operations of the respective drawer. Thus, in the embodiment shown in FIG. 39, drawers 1-8 having respective independently operable drawer assembly electronics modules 560-574 may be further connected to the master interface PCBA 544 and ultimately connected to the embedded PC assembly of staining apparatus 526. Thus, each one or more functions of PCBAs 548-558 may be implemented upon one or more drawers 1-8 having respective drawer assembly control modules 560-574 in continuous and independent fashion. Continuous and independent operation of the drawers while performing desired tasks may increase the efficiency of the staining process(es) by allowing multiple functions to occur without interruption.

Fluids used, for example, in pretreatment and staining for deparaffinization, target retrieval, rinsing, and application on slides may be supplied to the staining apparatus 526 via a provision of bulk fluids consisting for example, of common liquids. In one embodiment, a fluidics cart may be provided to hold containers for bulk fluids and waste. The fluidics cart may be designed to manage the transfer of bulk fluids to-and-from the staining apparatus 526. FIG. 47 shows one embodiment of an assembly of a fluidics cart 610 in connection with staining apparatus 526. In the example shown, the staining apparatus 526 rests upon a staining workbench 612. Fluid connections are run to the fluidics cart 610.

In one embodiment, a processing or staining step may take place in a processing tank or on the sample such as on a microscope slide. Similarly, a pretreatment step may take place in a processing tank or on the sample such as on a microscope slide.

In one embodiment, the apparatus may include means for storing such as hard disk drive, removable media, flash memory, network attached storage, internet connected storage, CD and DVD, and storage area networks, and distributing data such as protocols for processing slides, logs of completed and failed processing steps, errors during processing, processing status, or results of processing such as sample images. The embodiment shown, for example in FIG. 39, depicts the staining apparatus 526 in communication with a number of process systems and perhaps a number of computers, such as workstations 514, 516 and a server 500 (the latter residing either separately or as part of a workstation), may be achieved by use of a local area network (LAN), such as a group of computers and associated devices and peripheral components such as communications connections (e.g., modem connections) 502, 518, printer devices (e.g., report printer and data code label printer) 504, 506, input devices (e.g., keyboard and mouse) 508, 510, storage and/or recordable device such as CD-RW 512 that share a common communications line or perhaps wireless link and may even share the resources of a single processor, memory, or server within a small geographic area (for example, within an office building or complex) and may be accessed from outside the facility from a remote location e.g. via the Internet. Connection may also be established to a laboratory network, facilities intranet system, or even a laboratory information system (e.g., LIMS) such as through a bridge. Temperature values, historical actions, and particular timing activities may be captured and stored for local or remote access through the use of such a system. This information may include every action undertaken on every slide, quantities and usage for every individual reagent bottle, historical usage and maintenance information for instrument components, detailed diagnostic data, configuration values, etc.

Figure 42:
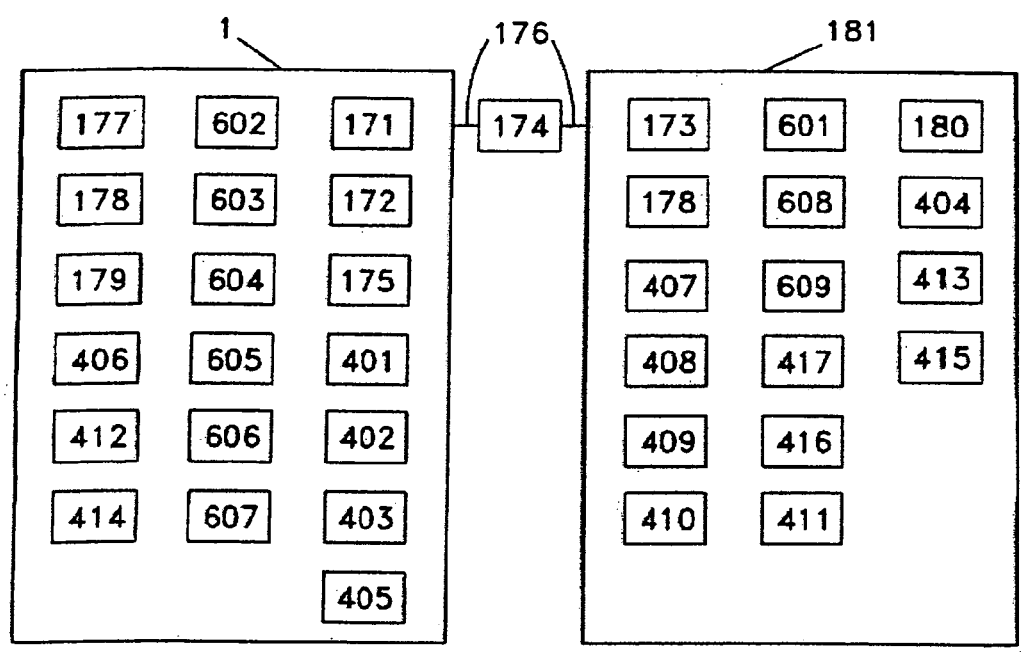
FIG. 42 is a block diagram showing one embodiment of the internal software features.

In one embodiment, the apparatus may comprise scheduling means such as hardware or software scheduling means for prioritizing, scheduling and executing tasks, such as testing protocols. For example, the sample processing system 101 is configured to achieve an appropriate sequence of events that achieves a desired result to some degree. In achieving this sequence in an automated fashion to some degree, the sample processing system is deemed an automated sample processing system and achieves automatic processing of at least one sample. This automated sequence as well as other aspects of the invention may be controlled by hardware, software, or some combination of them to accomplish a desired sequence with limited human intervention. Regardless how achieved, the automated control may be provided by a process operation control system 171 to direct the various activities. As shown in FIG. 42, this (as well as other functionalities discussed) may be software programming or subroutines; again, it may also include hardware or the like. In processing a slide, the automated sample processing system may serve as an automated slide processing system.

The automated sequence may involve a significant number of steps. In fact each process can itself require many automated movements to achieve its goal. Each of these type of operations or actions may be relevant to understanding an instrument's operation. Further, each of these types of operations or even a lesser set of significant events may be considered important details of the sample process operation. As explained later, it may be valuable to capture information relative to a significant number of these actions such as all of these operations, some subset of these operations, one-half of these operations, one-third of these operations, or the like. Further, even the nature or type of the events that may be of interest may be varied. In general, any event that may indicate the propriety of operation or processing may be a subject. Naturally in order to achieve automated processing it may be necessary to schedule the various sample process or process operations desired. This can, for example, be achieved by an item of software or the like that acts as a multiple event scheduler 401. In accordance with the desire for an automated processing system, embodiments of the present invention may include robotic sample process functions or a robotic motion system 172 responsive to the process operation control system 171 to achieve the desired operation steps. An independent fluidics scheduler may also be enabled to run concurrently with the robotics adaptive scheduler as will be discussed further below.

As mentioned above, there may be a large number of process steps accomplished. As may also be appreciated from the nature of the processes envisioned, there may be uses of many different substances or the like. Whether involving a substance or merely a physical action, these types of items may be considered as relating to operationally influential exteriorly-consequential information. The item may be operationally-influential in that it either its operation or failure in operation may directly or indirectly influence some type of conduct. This conduct may be exteriorly-consequential in that it may be a conduct that does not take place within the process system itself but external to it. As such the present invention may provide the capability to monitor that information. This capability may even be considered as an operationally-influential exteriorly-consequential information monitor 402 as shown generally in FIG. 42. Thus the present invention may include an ability to monitor information of a broad nature.

Figure 48:
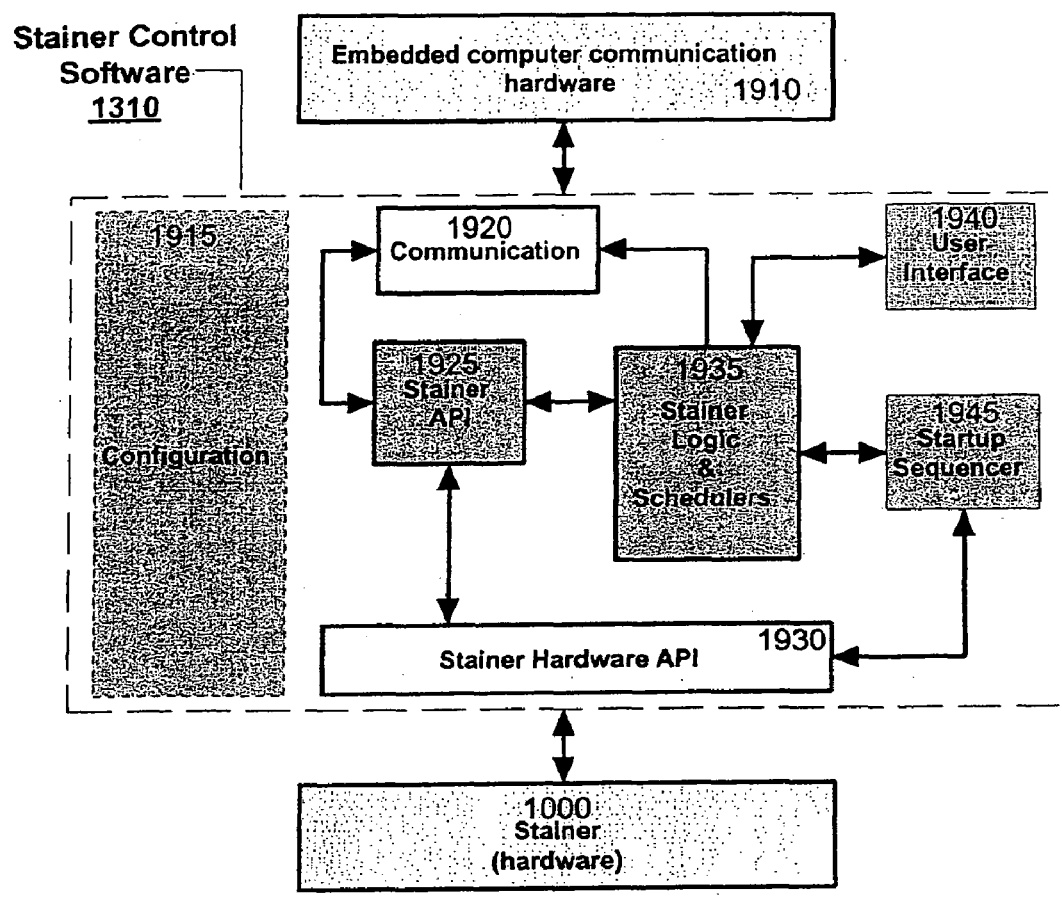
FIG. 48 is a block diagram illustration of an embodiment of Stainer Control Software.

FIG. 48 illustrates an embodiment for an exemplary software architecture for the Stainer Control Software 1310. In some embodiments, SCS 1310 may run on a computing system embedded within stainer 1000 and control and coordinate the operations of individual stainer 1000 with other system components. In some embodiments, SCS 1310 may consist of a number of unique autonomous threads or sub-processes. Each thread performs specific tasks and manipulates a number of objects to control and monitor physical device states.

As shown in FIG. 48, exemplary architecture for SCS 1310 includes communication module 1920, which interacts with embedded computer communication hardware 1910 on stainer 1000, in order to communicate with SMS 1320. In some embodiments, communication module 1920 also receives information and messages from stainer logic and schedulers module 1935 and may also exchange information with stainer API module 1925. In some embodiments, stainer API module 1925 provides an interface for control of stainer hardware at a high level. In some embodiments, stainer API 1925 will translate the high level commands it receives into a sequence of lower level stainer hardware API module calls in order to accomplish the objects of the received command.

In some embodiments, stainer API module 1925 consists of a group of functions and procedures that perform the process of pre-treating and staining slides 7. In some embodiments, methods performed by Stainer API 1925 are high level in nature and may rely upon many lower level objects to perform their tasks. For example, stainer API may direct robot 22 to aspirate a specific reagent. As a result, stainer hardware API 1930 may direct robot 22 to probe washing station 8, to allow probe 10 to be washed prior to reagent aspiration. The probe washing command in turn may translate a command into a sequence of even smaller steps performed by multiple individual components on stainer 1000.

Stainer hardware API module 1930 controls low-level functionality on various devices and components within stainer 1000. For example, stainer hardware API module 1930 may poll sensors to ensure that all reagent rack doors are closed prior to commencing operation on stainer 1000.

In some embodiments, both stainer API module 1925 and Stainer Hardware API 1930 can also simulate the actions of each of the devices in their control. For example, Stainer API 1930 may model the time taken by probe 10 to apply reagent to a slide, and/or the decrease in available volume of fluid in reagent container 1080. The completion time and/or buffer availability information may be sent quickly to communication module 1920, for onward transmission to SM 1330. The simulation of the actions of system components allows stainer API 1925 and stainer hardware API 1930 to operate in a simulation mode, where no physical actions are actually taken by system components. In some embodiments, stainer API 1925 will return results based on its simulation model to SMS 1320 and SM 1310, which may be unaware that stainer API 1925 is operating in a simulation mode and continue to perform their usual functions. In a simulation mode, the system may be debugged and new procedures tested quickly without risk to or use of system components and expensive reagents. In some embodiments, an accelerated simulation mode may be available, wherein an entire simulation run may be executed in a very short time.

In some embodiments, exemplary stainer logic and schedulers module 1935 contains the logic and decision criteria needed to trigger, initiate, suspend, report, or terminate actions performed by stainer 1000. In some embodiments, stainer logic and schedulers module 1935 also performs automated background tasks such as waste pull and monitoring. In some embodiments, logic for the control and coordination of robotic and fluidic schedulers in stainer 1000 may also be contained within this component. In some embodiments, robotic head 22 on stainer 1000 moves to ensure that reagents are applied to or removed from a slide 1045 within the time period specified by a treatment protocol. In some embodiments, a robotic scheduler controls the movement of robotic head 1032 to ensure that treatment protocol-related constraints are met. In some embodiments, bulk fluids needed by stainer 1000 are stored in containers 1299 on fluidics cart 1295 and can be delivered to processing tanks within stainer 1000 at appropriate points in time. In some embodiments, the conduits conveying the fluids to the processing tanks may be limited and shared by several fluid containers. Accordingly, the allocation of conduits is scheduled to ensure that all fluids are ready for delivery when needed, and that the conduits are adequately flushed to eliminate residues. In some embodiments, a fluidics scheduler controls the allocation of the conduits to fluids.

Exemplary configuration module 1915 holds configuration settings for stainer 1000 including device types, positions, speeds, accelerations, set points, etc. Other SCS modules may request operating parameters from configuration module 1915. For example, stainer logic and schedulers module 1935 may request the speed of robotic head 1032 from configuration module 1915 to calculate a viable schedule for movement of robotic head 1032.

Exemplary startup sequencer 1945 orchestrates stainer 1000 through a safe and orderly startup when it is powered on. In some embodiments, the system will enter a normal running mode after successful completion of the startup sequence. In some embodiments, startup sequencer 1945 may perform one or more of the following functions: system initialization including language selection; preparation of internal data structures and the GUI; checking the operating system and firmware versions and characteristics; locking all loaded drawers; checking and performing tests on motion controller hardware and electronic boards in the stainer; homing the robot; washing the probes; rinsing processing tanks; connecting to a specified System Manager Server or locating SMS on a LAN synchronizing date and time with other system components; and starting the schedulers. In some embodiments, exemplary user interface module 1940 provides operational information updates to the built in LCD display and to accept operator input.

Figure 49:
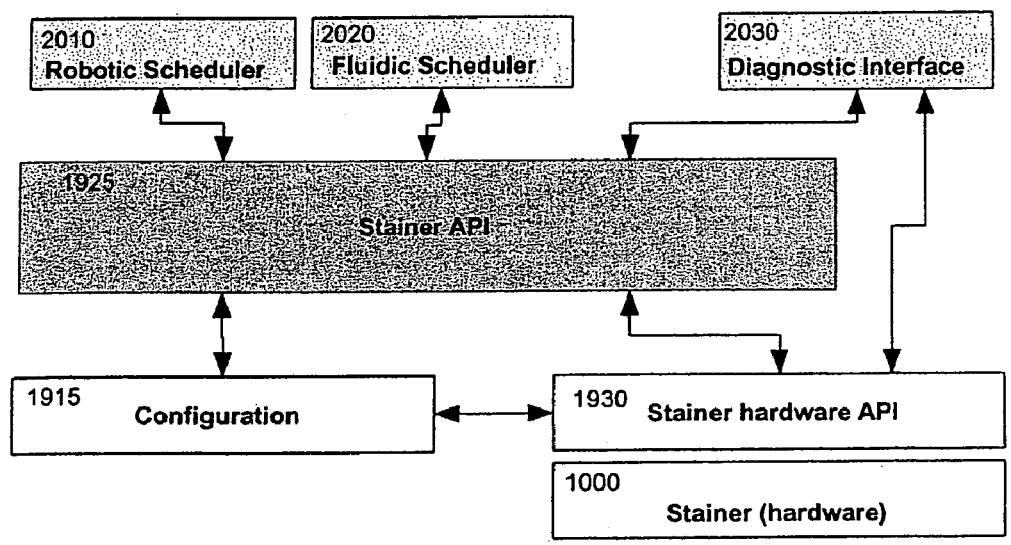
FIG. 49 is a block diagram illustration of an embodiment of a Stainer Control Software (SCS) Application Program Interface (API).

FIG. 49 shows an embodiment for the interactions of an exemplary Stainer Applications Programming Interface ("API") 2000 for control of functions of stainer 1000. In some embodiments, stainer API 1925 provides a high-level system control and monitoring interface to perform operations for slide processing and pretreatment. In some embodiments, stainer API 1925 may serve as an interface for robotic scheduler 2010 and fluidic scheduler 2020 to invoke and exchange information with routines in diagnostic interface 2030.

In some embodiments, stainer API module 1925 provides a mechanism to access diagnostic interface 2030, which may be part of communications module 1920. Diagnostic interface 2030 facilitates access to hardware on stainer 1000, where machine and component status can be queried and various commands related to diagnostics executed. In some embodiments, diagnostic interface 2030 may exchange data and control information with support module 1610 to facilitate remote monitoring, diagnosis, and support of functions and operations of stainer 1000.

Robotic scheduler 2010 and fluidic scheduler 2020 work through stainer API 1925, which also handles all interfaces to the low level devices through stainer hardware API 1930. For example, in some embodiments, robotic scheduler 2010 may look ahead to determine the robotic head's next rendezvous (the location and point in time where the robotic head will be needed next) and may elect to park the robotic head close to that location by issuing an appropriate command through stainer API 1925.

Thus, in some embodiments stainer assembly API may provide access to several routines and functions that are useful for operations relating to the processing and pretreatment of slides. Some of these routines may invoke other routines provided by stainer assembly hardware.

Figure 50:
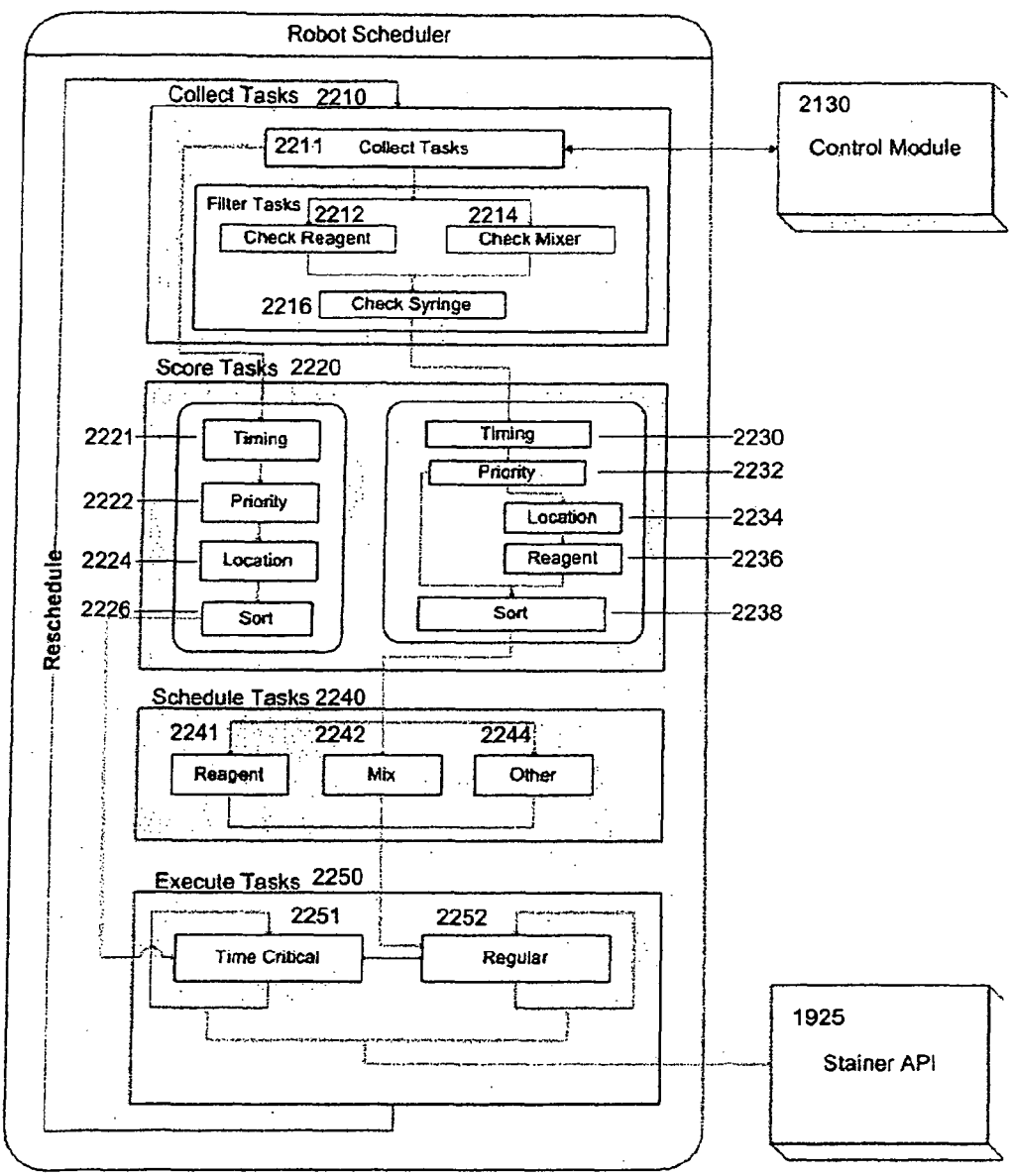
FIG. 50 is a block diagram illustration of an embodiment of a Stainer Control Software robot scheduler

FIG. 50 shows an embodiment of a block diagram showing interactions between components of an exemplary robot scheduler 2010. The SCS scheduler, including robotic scheduler 2010 and fluidics scheduler 2020, are responsible for conducting staining (robot) operations and pre-treatment (fluidics) operations on stainer 1000. In some embodiments, robot scheduler 2010 may use dynamic algorithm that continually readjusts the staining tasks that need to be executed, based on system changes, user actions, and a continuous feedback loop. Embodiments of fluidics scheduler 2020 may also use a dynamic algorithm capable of continually monitoring system changes and scheduling new pretreatment tasks as they are requested. Features provided by the dynamic, self-adjusting scheduling algorithm facilitate the continuous workflow processing of slides. In some embodiments, robotic scheduler 2010 and fluidic scheduler 2020 are instantiated as autonomous threads on stainer 1000 startup and continuously operate to control actions of stainer 1000.

In some embodiments, robot scheduler 2010 manages the coordination of robot actions, including aspiration and mixing of reagents, for the staining of each slide 1045 within the dynamic environment in stainer 1000. Robot scheduler 2010 analyzes impending steps for each slide, as defined by the treatment protocol for the slide, then intersperses the steps across all slides 1045 and scores (prioritizes) them. In some embodiments, stainer 1000 may contain multiple slide drawers, each of which can contain several slides 1045, and each of these slides 1045 may have its own individual treatment protocol necessitating an individually tailored pretreatment and/or reagent application schedule. From the viewpoint of robotic scheduler 2010 tasks are performed on each of the slides 1045 in stainer 1000 according to the programmed protocol and to the priority of a task or group of tasks, which priority may be adaptively updated, according to user inputs or stainer 1000 conditions.

In some embodiments, robot scheduler 2010 ensures that robot 1032 has enough time to rinse probe 10, aspirate and/or mix reagents, travel to the location of a slide 7, and apply the reagent to slide 7. This sequence of tasks may be repeatedly performed for each slide 7 present in the stainer. Robot scheduler 2010 therefore looks at the next task to be performed for each object such as a slide, and prioritizes, or scores, tasks and groups of tasks so that they may be executed in an optimal sequence If robot scheduler 2010 determines that a task may be postponed, the task may be pushed down and re-scored later. In some embodiments, robot scheduler 2010 will work on the highest scored task first and then proceed to other tasks in order of priority. In some embodiments, the highest scored task may be the most time critical task. In some embodiments, if robot scheduler 2010 determines that robot 22 does not have sufficient time to aspirate and apply reagent to a slide 7, a buffer may be applied to slide 7 to preserve the sample and the task marked to be re-scored later.

In some embodiments, the speed at which robot 1032 can perform actions and number of slide slots provided in stainer 1000 are matched to ensure that the spoiling of slide samples on account of treatment protocol violations is extremely rare or non-existent. In the unlikely event that robot 1032 is unable to perform its actions within the specified period or incubation tolerance for a treatment protocol step (for example, due to a transient mechanical problem), the violation is logged, but processing of slides 1045 is continued. When the processing of slides 1045 in a slide rack 1065 containing spoiled slide 1045 has been completed, a qualified technician can review the log to determine the nature and seriousness of the treatment protocol step tolerance violation, and also view the resulting stained sample to determine if the results are acceptable.

In some embodiments, robot scheduler 2010 will continually monitor all system events and re-adjust scheduler in response to any changing events to allow all slides 1045 to complete properly. In some embodiments, scoring and scheduling may be performed in accordance with algorithms described below. In some embodiments, robot scheduler 2010 and fluidics scheduler 2020 may operate to maximize throughput of stainer 1000, as measured by the total number of slides 7 successfully processed in a given period of time. In some embodiments, robot scheduler 2010 may recompute schedules to respond to dynamic changes in the load of stainer 1000 such as may occur when new slide racks are loaded and rack priorities are changed. In some embodiments, robot scheduler 2010 may handle expected and unexpected failures and errors by trying to isolate affected subsystems and save slides 1045 from spoiling. The ability to isolate affected subsystems in order to accommodate continuous workflow is facilitated and enhanced by the distributed architecture and substantially independent operation of some electronic and mechanical assemblies such as the drawer stack printed circuit board assemblies describe in other sections of the application.

As shown in FIG. 50, embodiments of a robotic scheduler 2010 may include collect tasks module 2210, score tasks module 2220, schedule tasks module 2240, and execute tasks module 2250. In some embodiments, collect task module 2210 interfaces with a control thread to obtain a list of all pending robot tasks. Robot tasks include all tasks that utilize robot 22 or tools associated with the robot, such as reading a reagent label using the camera, tipping a slide, or dispensing reagent on a slide 7 using syringe pump and probe 10. In some embodiments, tasks that need to be performed next are identified and collected while all the others are filtered out.

In some embodiments, score tasks module 2220 calculates a numerical score for each collected task based on several predefined categories, such as rack priority, incubation expiration time, or reagent availability. In addition, each category may be ranked by its relative importance. Once scored, the tasks are sorted in descending order of task scores, so that high scoring tasks are prioritized and appear at the top of the sorted list.

In some embodiments, schedule tasks module 2240 selects and groups tasks to be performed next, and generates additional tasks for the syringe pump, probe 10, or mixer 9A subsystems in the context of their current state. In some embodiments, sequence tasks module 2240 may optimize the slide staining process by reducing idle delays. In some embodiments sequence tasks module 2240 may operate to increase responsiveness and flexibility to so that tasks may be re-scheduled under the dynamically changing conditions. Execute tasks module 2250 interfaces with the Stainer API module 1925 to physically execute scheduled tasks. In some embodiments, execute sequence tasks module 2250 may preempt scheduled tasks with other time-critical tasks due for immediate execution.

In collect task routine 2211, a list of all currently pending robot tasks gathered from the top of each subsystem queue is obtained from control thread 2130. In some embodiments, objects 2160 may be associated with slides 7, slide drawers, reagents, and reagent racks. For example, a slide object pertaining to a slide 7 may include queues of pending tasks associated with the slide. Likewise, slide drawer object, reagent object, and reagent rack object may include queues of pending tasks associated with slide drawers, reagents, and reagents racks respectively. In some embodiments, queues may be implemented as first-in first-out lists. For example a slide queue might contain a task to dispense reagent, and a slide drawer queue might contain a task to read all slide labels in the rack.

In some embodiments, check reagent routine 2212, check mixer routine 2214, and check syringe routine 2216 are used to filter out tasks associated with reagents, mixers, and syringes respectively, where prerequisites for the tasks are lacking. Thus, tasks whose prerequisites cannot be satisfied because of reagent, syringe, or mixer unavailability are filtered out. For example, if reagent A is not present in reagent rack then a task requiring reagent A may be filtered out. Filtering ensures that the list of tasks submitted for scoring, sorting and scheduling are those that can run to completion if scheduled. In some embodiments, data associated with a task could include the task's earliest execution time, latest execution time, task command, and task status.

In some embodiments, collect task routine 2211 may classify tasks as time-critical or regular tasks. Time-critical tasks may need to be executed at specific times with very tight tolerances. Regular tasks are not time-critical and their tolerances are considerably more generous. In some embodiments, collect task routine 2211 may also create, use and update lists of time critical and regular tasks available for scheduling. In some embodiments, buffer and water rinse tasks may be classified as time-critical. A buffer rinse protects samples on slide 7 from drying out therefore applying or re-applying a buffer rinse at specified intervals is considered time-critical. Accordingly, if a buffer solution on slide 7 is near its expiration time and there is insufficient time for dispensation of the next reagent, a new buffer rinse task may be created.

In some embodiments, score tasks module 2220 calculates a numerical score that is used to prioritize potentially executable tasks for execution. In some embodiments, tasks submitted for scoring are analyzed taking into account the type of each task (e.g. rinse or dispense), their spatial properties such as slide location, temporal properties such as reagent incubation period expiration, other properties such as rack priority, and properties relating to system or subsystem state such as the reagent currently in a syringe.

Figure 51:
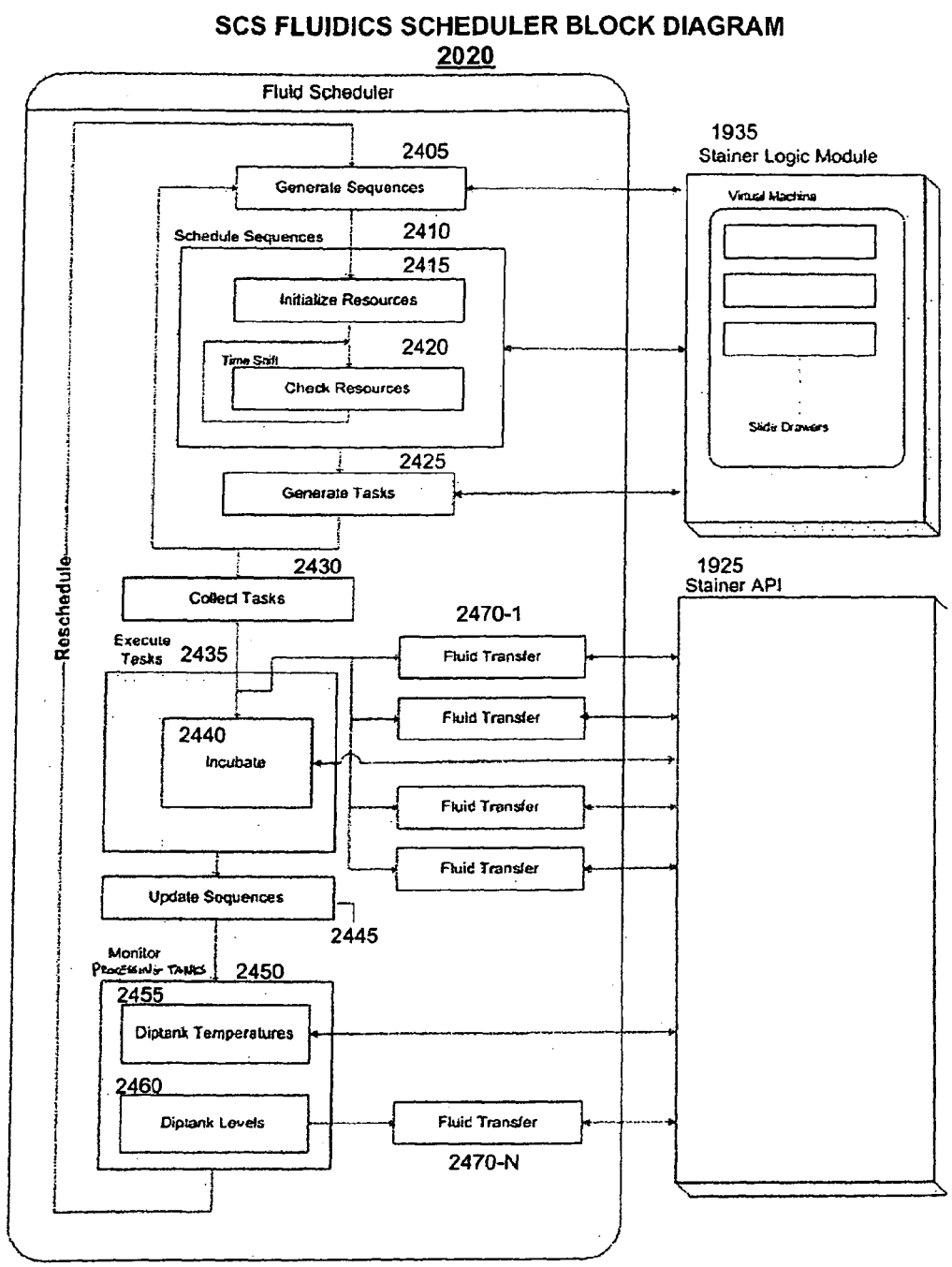
FIG. 51 is a block diagram illustration of an embodiment of a Stainer Control Software fluidics scheduler

FIG. 51 shows an embodiment of a block diagram of an exemplary fluidics scheduler 2020. In some embodiments, fluidics scheduler 2020 may be an autonomous process and implemented as one or more threads, which run in a continuous loop within the context of SCS 1310. In some embodiments, a fluidics scheduler thread may run independently but may query other components for the data it needs to create schedules and to coordinate task execution related to the schedules. In some embodiments, stainer 1000 may have a limited set of conduits to convey fluids to and from the bulk fluids cart, or to remove waste from the stainer. Additionally, conduits and chambers within stainer 1000 may need to be periodically flushed to ensure that there is no reagent or fluid cross-contamination. Embodiments of fluidics scheduler 2020 operate to ensure that the conduits are available to fluids in a manner that ensures that fluids will be delivered to or removed from appropriate locations in stainer 1000 at points in time when they are needed. Fluidics scheduler 2020 allows the time-sharing of conduit resources to facilitate various operations performed by stainer 1000.

In some embodiments, the fluidics subsystem may have multiple conduits each of which may be controlled by multiple individual valves and pumps. Accordingly, fluidics scheduler may create and implement schedules permitting multiple actions to be taken in parallel, such as directing fluids along different fluid paths simultaneously. In some embodiments, individual control systems associated with the conduits may be inherently parallel. For example, a valve may stop the flow of fluid in one conduit, while another conduit is simultaneously removing waste fluid from the stainer. Therefore, in some embodiments, fluidics scheduler 2020 may direct the execution of individual actions by coordinating a dynamic collection of autonomous threads, each responsible for executing distinct individual tasks.

In some embodiments, a single run through fluidics scheduler 2020 may consist of checking each slide drawer object for a pending pretreatment request, generating a sequence of fluidics actions for each such request, and then directing the execution of any sequenced action when its scheduled time has arrived. Fluidics scheduler 2020 may then loop back and repeat the cycle above.

In some embodiments, slide drawer object may provide information related to a slide drawer 100 including drawer identification information, drawer state, drawer pretreatment related information, drawer pretreatment sequence, drawer deparaffinization treatment protocol steps, drawer target retrieval treatment protocol steps, pending tasks, and processing tank fluid level which may be used by fluidics scheduler 2020 in making scheduling decisions. In some embodiments, a schedule may include task related information such as an identifier, task originator, task command, task status, source and destination containers, fluid type, task start time, and duration. In some embodiments, fluidics scheduler 2020 may use a list of shared fluidics resources, and interface with stainer API module 1925 and stainer logic and schedulers module 1935. In some embodiments, exemplary task commands could include pause, fill processing tank, empty processing tank, incubate in processing tank, heat processing tank, cool processing tank, flush processing tank, replenish processing tank and wait in processing tank. In some embodiments, commands may be executed by appropriate calls to stainer API module 1925. Each command may perform numerous lower level individual steps to carry out the command. For example, an empty processing tank command requiring a fluid transfer, may cause necessary valves to be opened, the pump to be started, the pump stopped when fluid transfer has completed, and the valves closed when the action has terminated.

To illustrate the operation of fluidics scheduler 2020 an exemplary sequence of operations is described. For example, when a rack of slides is newly loaded into stainer 1000 and determined to require deparaffinization, fluidics scheduler 2020 obtains the needed treatment protocol steps and uses them to generate a comprehensive sequence of fluidics states. Accordingly, a five minute incubation of slides 7 in a processing tank 101 filled with solvent fluid may be needed. The incubation step is mapped into three distinct fluidics states: filling the processing tank from a solvent bottle, incubating the slides 7 for the specified five minute duration and draining the processing tanks 101 contents. During the period when the two fluid transfer phases are in progress, other processing tanks cannot use the conduit that is being used to effect the fluid transfer. However, the processing tanks may make use of any free conduits to perform needed fluidic transfers. In some embodiments, some conduits may have dedicated functions. For example, one conduit may be dedicated for solvents, another for alcohol, and a third for water. Other resources such as the processing tank heating system, which may be needed for the five minute incubation period, are nonexclusive-use resources. Thus, a number of processing tanks may be heated simultaneously. After sequences have been generated resource conflicts are resolved to create a schedule. In some embodiments, fluidics scheduler may ensure that the pretreatment process is not interrupted after it has been commenced.

As shown in FIG. 51, exemplary fluidics scheduler 2020 includes generate sequences module 2405, schedule sequences module 2410, generate tasks module 2425, collect tasks module 2430, execute tasks module 2435, update sequences module 2440, monitor processing tanks module 2450. In some embodiments, execute tasks module 2435 in exemplary fluidics scheduler 2020 may also generate several fluid transfer task execution threads 2470-1 through 2470-N to direct the performance of tasks scheduled for execution.

In some embodiments, generate sequences module 2405 interfaces with stainer logic and schedulers module 1935 and examines active slide drawer objects 2162 to determine whether there are pending requests for pretreatment or processing tank rinse. If a pending request exists then generate sequences module 2405 may use the appropriate treatment protocol to generate a sequence of steps for scheduling and execution. In some embodiments, the sequence of steps may relate to deparaffinization and/or target retrieval. An exemplary sequence of steps generated by generate sequences module 2405 may include information such as steps related to processing tank filling and draining, processing tank rinses, whether slides 1045 are tipped during the process, and the resources for each step in order to provide the scheduler with sufficient information to make decisions. An exemplary sequence may include steps such as: fill processing tank with target retrieval fluid; turn on the processing tank heater and heat for I minutes; turn off heater and cool for J minutes; drain processing tank to waste; fill processing tank with water; incubate in water for K minutes; and drain processing tank to waste.

In some embodiments, schedule sequences module 2410 schedules drawer pretreatment sequences in order to optimize the use of shared fluidics resources. In some embodiments, schedule sequences module 2410 may develop a schedule in order to reduce the duration of pretreatment phase for each drawer. Sequences may be run in parallel if they use different resources, or use the same resources at different time intervals. In some embodiments, currently executing fluidics sequences may get priority with respect to claims on shared resources.

In some embodiments, utilization factors may be associated with each resource. When a resource may be shared its utilization factor is increased proportionately upon every allocation. When a resource is exclusive its utilization factor is 1 (100% utilization) whenever it is allocated. In some embodiments, each shared resource requested by the scheduled sequence may be checked at critical points by calculating its total utilization factor. In some embodiments, if a resource allocation would cause the utilization factor for a resource to exceed 100% at any point in time, the sequence being scheduled may be time shifted to resolve the conflict. Schedule sequence module operates iteratively and is based in part upon time at which pretreatment requests were made by each drawer.

In some embodiments, schedule sequences module 2410 obtains all sequences already scheduled and in progress. Next, shared resource data is initialized by initialize resources routine 2415 based on the sequences already in progress. In some embodiments, each new sequence submitted for scheduling is examined for any shared resource conflicts by checking each resource using check resource routine 2420 iteratively. If another conflict is found, the sequence is time shifted again by an appropriate amount and all shared resources are rechecked. The process continues until a conflict free schedule is generated. In some embodiments, time shift amounts are calculated precisely to coincide with the points in time at which the utilization factors of the shared resources change. In some embodiments, shared fluidics resources could include fluidics paths (including bottle and processing tank valves, routing valves, pumps, and conduits), processing tanks, and heaters. In some embodiments, the scheduling process is repeated for each newly generated sequence that needs scheduling.

In some embodiments, generate tasks module 2425 generates executable tasks from newly scheduled sequences. In some embodiments, it translates the sequence for each newly scheduled drawer from a format suitable for scheduling into a list of tasks with a format suitable for execution. The output of generate tasks module 2425 could include actual task commands, a scheduled start time, a fluid id, and source and destination information.

In some embodiments, collect tasks module 2430 creates a list of ready-to-execute pretreatment tasks for all active slide drawer objects 2162. In some embodiments, all slide drawer objects and their associated fluidics tasks may be monitored to identify ready-to-execute tasks, which are those tasks whose scheduled time has arrived.

Execute tasks module 2435 executes scheduled tasks. Fluid transfer tasks are executed indirectly by interfacing with stainer API module 1925 via dynamic task execution threads direct the performance of physical actions on valves and pumps. Other tasks, such as incubation, may be executed directly by starting their countdown timers. In some embodiments, task execution module may spawn several individual fluid transfer task execution threads 2470-1 through 2470-N that may execute in parallel to direct simultaneous fluid transfers along different paths. In some embodiments, each task submitted for execution is examined. For non-transfer tasks, where physical actions are not taken, the start of a new state may be recorded. In some embodiments, for tasks with physical actions, the applicable function in stainer API module 1925 may be invoked. In some embodiments, to execute a fluid transfers, task execution module may dynamically launch an appropriately initialized task execution thread. Each task execution thread will cause performance of lower-level actions by calling an appropriate function in stainer API module 1925.

In some embodiments, fluidics transfer functions provided by stainer API module 1925 may have a set of locks to prevent more than one task execution thread from gaining access to exclusive resources such as valves and pumps.

In some embodiments, task execution threads 2470-1 through 2470-N may each execute a fluidics transfer thus allowing multiple simultaneous or overlapping fluidics transfers in stainer 1000. In some embodiments, threads 2470-1 through 2470-N may directly interact with stainer API module 1925 to perform any lower level actions. Errors caused by equipment failure, or other external events encountered while executing an API function may also be handled by task execution threads 2470-1 through 2470-N. In some embodiments, errors may be handled by retrying the fluid transfers, pausing, or halting further processing tank processes, or disabling the processing tank.

In some embodiments, update sequences module 2445 monitors timers, such as incubation timers in stainer 1000, records the completion of non-fluid transfer tasks, updates tasks and sequences as they complete, and detects conditions that create a need for rescheduling. When tasks finish executing the task sequences for the drawers that originated the completed tasks may need to be updated to reflect the actual machine state of machine so that completed tasks are not repeatedly performed. Accordingly, update sequences module 2445 examines all currently executing tasks and updates the originating sequence to reflect completed tasks. In some situations, a task that cannot be completed because of abnormal conditions may be rescheduled.

In some embodiments, exemplary monitor processing tank module 2450 executes non-scheduled, periodic actions and tasks such as monitoring processing tank levels and temperatures, and replenishing evaporated target retrieval fluid with de-ionized water to prevent slides 7 from drying. In some embodiments, deviations from the acceptable incubation tolerances may be logged by monitor processing tank module 2450. In some embodiments, the level of target retrieval fluid in the processing tanks undergoing heating is also periodically monitored. For example, when the level of de-ionized water in a processing tank drops due to evaporation, it is replenished with more de-ionized water in order to prevent slides 1045 from drying out. In some embodiments, the transfer of de-ionized water to the processing tank may be accomplished through a task thread, which may interface with stainer API 1925.

Returning to the aspect of monitoring or capturing information, an embodiment of the system may be designed to monitor replenishable supply information, such as the status of buffers, reagents, stains or the like. By monitoring for a potential need for replenishable supplies the system may not only provide the replenishable supply information monitor 403 shown in FIG. 42, but it may also relieve operators of some concerns. It may also remove at least one possibility for human error. Significantly, the system may also act to automatically notify any number of people relative to the information monitored. With respect to replenishable supply information, the system may notify a user, an operator, an administrator, or even a supplier of an actual, potential, or impending need to replenish supplies. The system may also preclude initiation of processing for introduced samples until the supplies specifically required to process those samples are in place. As such the system may be considered as including an automatic notice element 404, or an automatic operator replenishable supply notice element, an automatic supplier replenishable supply notice element, or the like.

In a similar fashion, an embodiment of the system may monitor or capture information that is of interest to the continued or continuous operation of the device. As such it may be monitoring instrument maintenance information. This may include, but is not limited to monitoring part cycle information, ranging from a gross information such as age of the device, estimated number of cycles, to even monitoring specific information such as monitoring individual part cycle information (e.g., how many times and actual valve was turned on or off, etc). By including an instrument maintenance monitor, an instrument maintenance information monitor 405, a part cycle monitor, or an individual part cycle monitor 406, the system may facilitate not only enhanced reliability and continuous operation, but it may permit preventative maintenance such as maintenance based on product cycles or mean times between failures. Naturally, it may also use the automatic notice element 404 such as providing an automatic maintenance notice element to inform a wide range of persons of such issues. It may also provide a means for remote off-site connection to monitor the status of instrument components.

Of course, a large variety of information may be monitored; embodiments of the system may monitor or capture information that relates to material requirements, such as expiration dates, lot information or the like. Thus the present invention may include a material requirement information monitor 407 so that it acts to automatically monitor material requirement information. This may be a product expiration information monitor 408 that may even act with respect to an upcoming expiration and may even cause the set of automatically advance notifying a person by providing an automatic advance expiration notice element. For items that may be very important there may even be multiple notices either concurrently or sequentially and as such the system may include a multiple advance expiration notice element. Another type of information that may be monitored is historical usage information such as information of a statistical or past nature. Thus the system may include an historical usage information monitor 409. From this, predictive estimates may even be made such as a likely date upon which to order an item or the like. Through monitoring predictive usage information, this may be one way the system may be able to provide an automatic predictive need notice element or even a predictive usage information element 410. It may also provide for a user statistical information monitor so that it can assemble and monitoring user statistical information and act on this such as by comparing to other historical or statistical information or the like. The present invention may also be configured to monitor sample process efficacy information such as by assuring particular protocols are followed or the like and may thus provide a process efficacy information monitor 411. Monitored information may be extrapolated to permit a totalizator 413 capability by adding up individual usages to know amounts left or otherwise impacted by operation. This may include totalizing usage information for an item such as a reagent or an individual part's cycles. Such a capability may serve as a totalization usage information monitor, a reagent totalizator, or a part cycle totalizator. The system may also report cost per test and other such synoptic information that may be important to the economics and efficiency of instrument operation from a practical perspective. By having a data capture element 414, the system may generate data that may include or permit analysis or use of a variety of aspects, including but not limited to: number of occurrence data, part operation data, amount of usage data, and amount of material used data. Such data may, of course, have a like element, perhaps a subroutine, to do or generate the various function or data involved.

The automatic processing may be achieved by designing a system with automated process operation capability or sequencing through at least some steps without human intervention. This may be controlled by or act in response to a process operation control system 171. This may be provided through hardware, software, or some combination of the two. One conceptual embodiment depicts some of the various capabilities in FIG. 42. Of course, the user needs the ability to specify the nature and sequence of the various steps or acts desired or even the appropriate priority or other scheduling parameters to be used. This can be accomplished by an input parameter capability 173 through the inclusion of even a sample process parameter input 173. Input can be retained by the creation of stored parameter process data 174 so that the system can achieve the aggregate or perhaps plurality of process operations desired and thus the input may be an aggregated sample process input. In order to facilitate uninterrupted processing, the input parameter capability 173 may be configured as an independent process parameter input with respect to the process operation control system 171, such that acts caused by the process operation control system 171 are unaffected by any action with respect to the independent process parameter input. Further, the input parameter capability 173 may also be configured as an autonomous input functionality through the inclusion of an autonomous input element.

With the desired types of processing input, the system may act to automatically schedule the various events perhaps through scheduler or 605. These events may be considered as making up an aggregated event topology in that there is an aggregation of desired events and in that the events themselves present some topology or contour for a processing sequence. This topology may include only the events or it may include certain goals such as a particular prioritization or outcome desired. When using an initial input, the system may achieve scheduling of the events in the manner desired. Of practical importance may be the ability of an embodiment of the invention to permit and facilitate operator changes to the initial aggregated event topology. Significantly, these changes may be achieved dynamically, such as while other parts of the system are continuing processing. In facilitating changes while otherwise operating with little or no interruption, the system may act to achieve adaptive scheduling. This may begin as adaptive scheduling of an initial aggregated event topology and may evolve into adaptive scheduling of an altered aggregated event topology. This may occur on individual or perhaps stand alone devices, such as a stand alone stainer, or it may occur on an inter machine basis, such as by using an inter machine schedule indicium or an inter machine schedule element. Regardless, it should be understood that the scheduling of an altered topology may occur after commencing an initial automatic processing routine.

The alteration of the aggregated event topology may include any variety of actions that effectively alter an initial setup. These may include but are not limited to: altering the aggregate, such as perhaps adding a sample, deleting a sample, changing a sample, or altering the topology such as accepting a user change input such as merely a change in priority. They may also include accepting a temporary user change such a change that a user wants to see the effect of but may not wish to implement. Thus the system may include a sample addition element, a sample deletion element, more generally a sample change element 601, or a temporary user change element, each of which may be considered as creating some type of altered aggregated event topology. It should be understood that altering the aggregate may also include other agents such as reagents which may also be added and removed accordingly. To permit a user decision, embodiments may include functionality or subroutines for activating a user change or undoing a user change. These may be considered a user change activation element or a user change undo element. Such selection may be presented in conjunction with a results display element 602 of some sort such as an effect synopsis display element, a temporal impact display element (e.g., the time impact on one or more samples or reagents to be processed as a result of the alteration), and even an estimated temporal impact display element, whereby the time effect is only estimated.

As a result of some type of alteration in the aggregated event topology, the system may reschedule events. This rescheduled sequence may be used to interrupt or may provide an interrupt 603 relative to the initial sequence and to thereafter continue revised automatic processing according to the altered aggregated event topology. As can be understood, this may be accomplished without completing the initial automatic processing. The rescheduling may be programmed to achieve a variety of result and then to compare with is "best" depending on how the operator or system define that goal. Achieving a variety of results can be accomplished by simulating runs or perhaps a portion of a run and comparing the results of that simulation. The simulation may be of varied sequences set up according to certain parameters as explained below. By so doing, embodiments may include varied-parameter robotic and fluidics control simulation functionalities 606, that is programming that simulates robotic and fluidics operations based on differing parameters. These varied-parameter robotic fluidics control simulation functionalities 606 may be responsive to the aggregated sample process input by acting on the data the input creates. The system may run multiple simulations for the same aggregated event topology with each simulation using different criteria to determine the sequence of steps. The results of these simulations may be indicium that can be used and compared. Comparison may be achieved by an automated process simulator comparator 604 which may look at any indicium resulting from the particular simulation being considered. From the indicium, a decision may be made and a particular set of parameters may be determined to cause an enhanced, if not optimum, sequence for a desired goal. These parameters may then be used in a functionality robotic control generator 607 which may then actually create the sequence that is used for the desired process operation. In this fashion, the system may have a process generator that is responsive to the automated process simulator comparator and from which an automated process functionality may be created.

As mentioned, the simulations may take into consideration a variety of input for factors, including a user parameter input. Of course, there are a variety of parameters that may be considered as the rescheduled sequence is determined perhaps by comparing indicium (e.g., any value having information relative to that particular model) relative to a particular model. These may include but are not limited to: a substance priority parameter, a reagent grouping parameter, a robotic movement parameter, a sample location priority parameter, a sample proximity priority parameter, a sample insert time priority parameter, a user input parameter, a user priority parameter, a sample time since last processing priority parameter, a time-based priority value parameter, and a sample weighting parameter.

The system may compare the results, perhaps by software that may act as a comparator 604. The elements compared may be elements such as comparing processing time indicium, comparing completion time estimates, comparing substance cost estimates, or comparing sample priority assignments, and as such may be considered as having a robotic control simulation results comparator, a sample time since last processing priority parameter robotic control simulation functionality, a time-based priority value parameter robotic control simulation functionality, a substance priority parameter robotic control simulation functionality, a completion time estimate comparator, a substance cost estimate comparator, a sample priority assignment comparator, a repetitive process simulator comparator, and even a qualitative analysis comparator. As mentioned earlier, to facilitate some type of comparison, it may use indicium, such as an initial robotic control indicium and a second robotic control indicium.

In establishing a system that is practical, it may be advantageous to include—at least initially for calculations time concerns—a limited number of different simulations. For example, two or three may be included and may thus be considered a first control simulation functionality, a second control simulation functionality, and a third control simulation functionality. By establishing a system with a sample time since last processing priority parameter robotic control simulation functionality the system may assign a higher priority to samples that have not had any or perhaps particularly important activities for some time. By establishing a system with a robotic movement parameter robotic control simulation functionality it may take into consideration how far a robot needs to move to assign priority to items that require less movement. By establishing a system with a substance priority parameter robotic control simulation functionality, it may include consideration the fact that some substances are particularly concerning either because of cost, rinse needs, toxicity, or the like. Finally in making a comparison to determine which parameters yield a more desirable sequence, the system may include an enhanced temporal scheduler element so that the system automatically evaluates which parameters are likely to yield the fastest processing time. Naturally, this enhanced temporal scheduler element may be based on an total sample basis or may be based on some subset thereof. It may even be based on individual samples such as for a stat run or the like. Thus the robotic control simulation results comparator 604 may act to provide an enhanced rescheduling of an altered aggregate event topology. In implementing the revised sequence, the system may provide a seamless initial adaptive schedule functionality interrupt and may act to seamlessly, perhaps without perceptible discontinuity, interrupt the initial sequence and continue with the new one. Further, since the simulations may be time consuming, it is possible do only an initial comparison, perhaps such as merely comparing two differing functionalities, to then select one of them such as an initial robotic control functionality and to then continue more simulations and comparisons. From this continued effort, there may be discovered an even better set of parameters and thus the system may thereafter implement a second robotic control functionality as perhaps a better solution. Naturally continued simulations and comparisons may occur.

As may be understood by the above, rescheduling due to an altered aggregate event topology may be impacted by a number of factors. As but one example it may be understood in shortening time for overall processing, the location of a particular substance or a particular sample may be important; the further between samples or substances, the slower the processing. Because of this type of factor, it is possible that the system may actually consider, simulate or otherwise assess factors and may suggest actions that may yield desired results. For example, the system may display at least one suggested sample location, a suggested sample drawer location, a suggested stainer location, or the like. From this the user may be able to accept a proposed action and may even be able to accept or reject the suggestion. Thus the system may display a suggested user selection. This may even be the act of displaying a temporally enhanced suggested user selection through providing a user selection menu or the like. From this, the system may accept a user parameter input through a user selection menu. The results may even be summarized to display a synopsis of the effect due to the alteration, such as to display a temporal impact due to the alteration. Naturally, this may be estimated and the system may act to display an estimated temporal impact. Whether impact based or suggestion based, the system may provide the user valuable input and in this manner it may actually provide a suggested sample location element, a suggested sample drawer location element, a suggested stainer location element, a suggested user selection element, a temporally enhanced suggested user selection element, or the like. Naturally, such activities as well as any rescheduling or simulating may be the result of an operator request, the system sensing an operator access event, the system accepting a user change, or even some type of operator access event sensor, such as a drawer sensor or the like.

Similar to the act of suggesting to the operator a particular action that may enhance scheduling, the system may act to inform the operator of needed events or the like. If a particular substance is required but is not present in the machine (likely as sensed by the device itself perhaps through the optical sensor), the system may automatically prompt an operator for a particular action needed, such as insert the needed reagent or the like. In downtime or otherwise, the system may even repetitively automatically check if an operator action is needed. As such the system may include an automatic operator need prompt 608. It may also provide a variety of information such as real time status information, pending sample information, a real time completion estimate for an aspect (e.g., a sample, a drawer, a group, or the like). Each of these may be accomplished by software and hardware perhaps by including a real time status information element, a pending sample information element, or a real time completion estimate element, each shown conceptually as the information element 609.

As to any of the above capabilities, such may not only act independent of the automated process operation capabilities, but where applicable, they may be fully functional even without the presence or operability of the automated process operation capability (which itself may or may not be in a process device). They may be achieved in a variety of manners, including by providing a separate full function computer 181 (e.g., separate from the capability provided or required by a process system) or that may be programmed to accomplish the desired function. In addition, in order to accomplish a goal of addressing practical and institutional needs, any capability may be configured to provide simplified use and may even be available in a highly simplified level of detail. This may be a "wizard" type of system where there is a "step-by-step" method for functions such as adding slides, achieving the desired input, or the like. Such an aspect may even be simple, regimented, and somewhat inflexible. A structured or simplified input can facilitate input by persons not required to have the full spectrum of skills necessary to be responsible for the operation of the sample processing system 1.

As part of the functions of monitoring or perhaps allowing play back of events, the system may include some type of data capture element 414. As may be appreciated from the initial discussion of the types of actions potentially needing to be programmed, the data capture element 414 may capture individual movement data, only robotic action data, individual robotic movement data, individual operation data, or even individual usage data. Thus the data capture element 414 may be an individual movement data capture element, a robotic action data capture element, an individual robotic movement data capture element, or an individual operation data capture element. All or any part of this data may be systematically stored such as storing all important details, only particularly important details (e.g., relative to highly sensitive valves, substances, or the like) or even only a significant number of details relative to sample process operations. Thus the data capture element 414 may be a systematic process detail capture element. Once captured, this data may be stored in a number of fashions. There may be a memory location at which such data resides and this may thus represent a significant process detail memory 412. It may also represent a subject sample data capture element and any of the memory types mentioned earlier may be used for such a purpose.

In storing the data, the system may create a segmented computer file, that is a file that contains only such data so that it is not as readily manipulated as other files. This may aid in assuring the accuracy or even certifiability of the events depicted. For instance for any particular sample, there may be automatically generated upon request a simulation—perhaps with a time base appended—of what happened to that particular sample as well as pictures of the sample before and after its processing. The data so stored may even be created as an inalterable computer record and perhaps may even include an integral change indicia that can prove its accuracy. When stored, the system may create a common format computer record so that user can easily work with it or it may create a proprietary format computer record that cannot be altered or the like. Thus the significant process detail memory 412 may represent a segmented computer file memory element, an inalterable computer record memory element, an integral change indicia memory element, a common format computer record memory element, or a proprietary format computer record memory element.

The capture of data may include time of occurrence data, such as actual date data, actual time data (e.g., UTC, etc.), precise time data (e.g., hours, minutes, seconds), relative time data, absolute time data, initiation time data, and even completion time data (e.g., process, protocol, motor operation events, or the like). Again, the data capture element 414 may include, but is not limited to, a time of occurrence data capture element, an actual date data capture element, an actual time data capture element, a precise time data capture element, a relative time data capture element, an absolute time data capture element, an initiation time data capture element, or a completion time data capture element.

One item that may be of particular user desire is the fact that the data capture element 414 may represent an individual sample process data capture element, an individual slide log data capture element, a type of protocol data capture element, and even an individual slide log data capture element. There may also be a real time individual slide log data display to show actual processing as it occurs.

Figure 43:
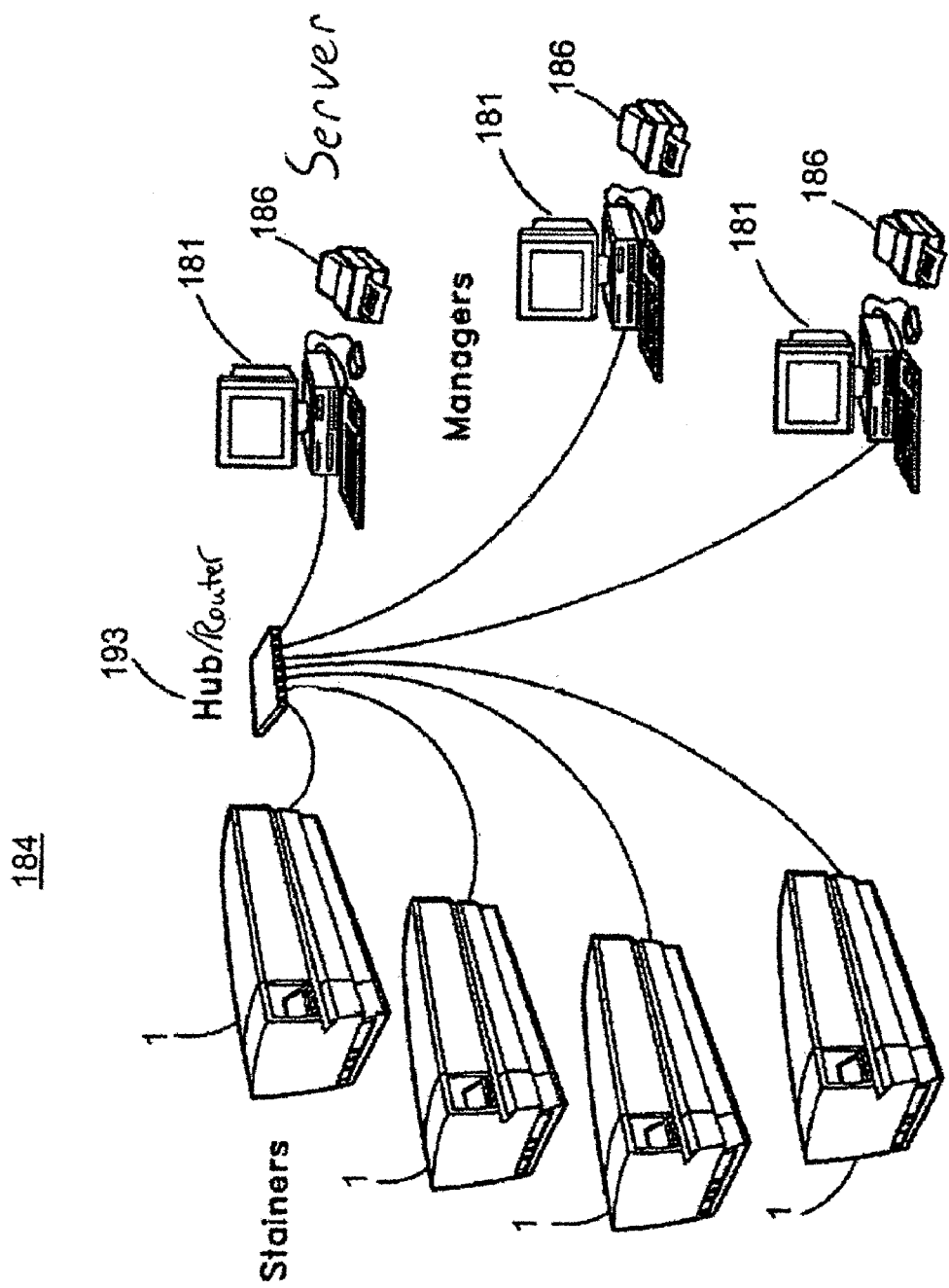
FIG. 43 is a depiction of an embodiment connecting multiple stainers with additional networked equipment.
Figure 44:
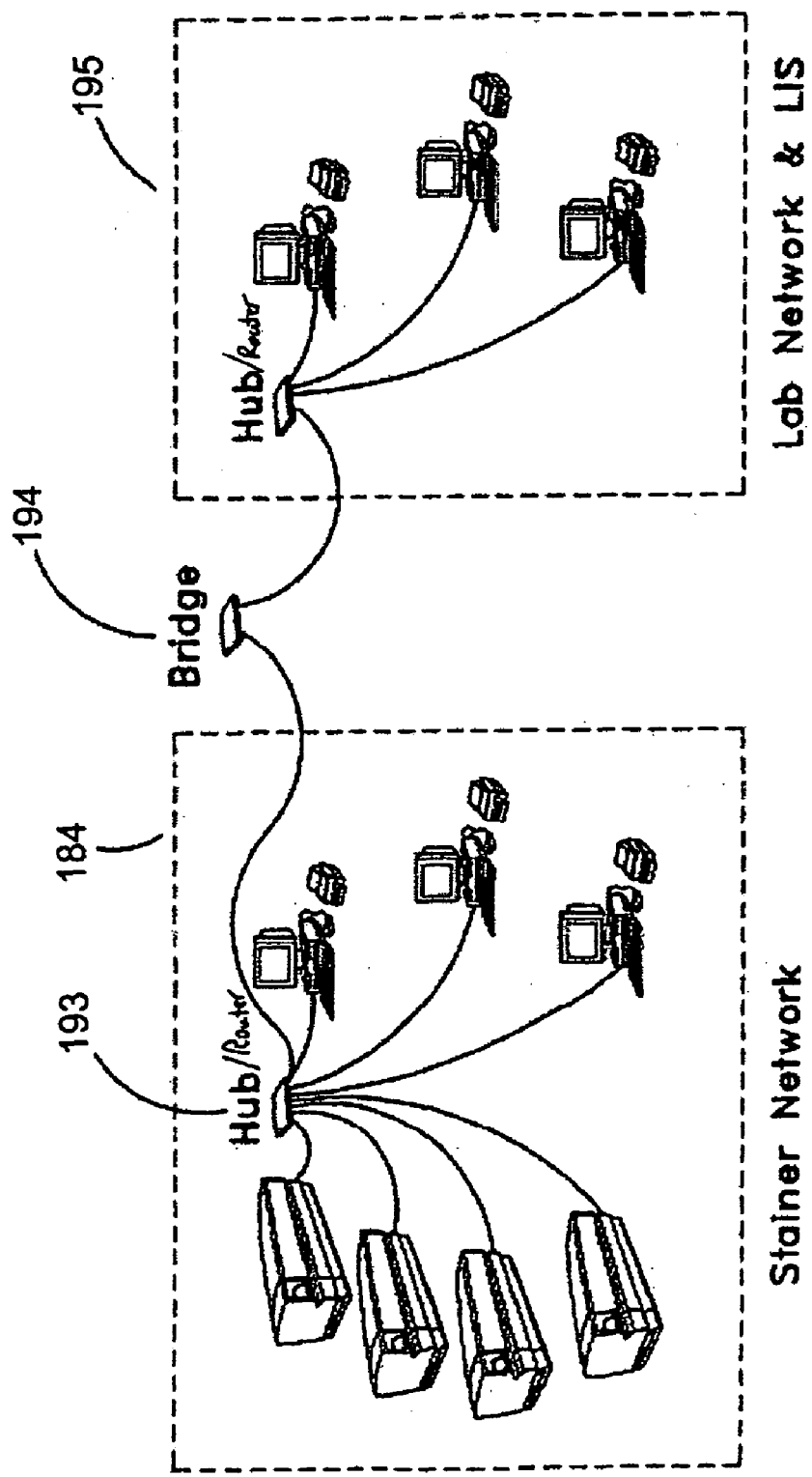
FIG. 44 is a depiction of an embodiment connecting a system to a lab network and lab information system.

As used above, the slide identification information may represent any information unique to a particular slide, such as a serial number, patient number, patient name, unique image, or the like. In keeping with privacy concerns, there may also be coded or perhaps encrypted identification information or internal identification information that others cannot use to identify the particular patient involved or the like. As discussed below and as shown in FIGS. 43 & 44, the overall system may include a number of staining instruments and thus the input can include stainer information (which may or may not be indicated or accepted by the automated system). Provision can also be included to achieve a rush test and as such there may be an immediate, urgent, or otherwise known as stat (an often used medical term for immediate) process request information element. Such may also be linked with user privileges information so that only certain individuals may displace other tests to create a different priority. Of course all permutations and combinations of the above may be included.

For automated operation, the input may create data such as parameter process data 174 that may be stored at some location. To provide autonomous operation, it may be independently stored perhaps in a physically independent memory even at a location remote from an actual stainer itself. This may be accomplished by utilizing a primary or secondary storage perhaps of a separate full function computer programmed or configured to accept and/or store data. In such a fashion, the computer may contain what could be considered as an independent process parameter memory 174. Since the computer is likely physically separate, it may be considered to have a physically independent memory perhaps even a remote location memory if it is remote from the process equipment.

By using independent memory and independent other functionality, the system may facilitate full operational functionality of the automated process operation capability. Since the automated process operation capability is fully operational during operation of either the memory or input, the storing or inputting or other function can be conducted without interrupting the process operation. Thus the inputs can be later accessed at a process time independent of the time of accomplishing slide process parameter input or storing. In addition, entry or storing may also be accomplished at least in part concurrently with the processing of certain samples. This processing may even be initiated significantly after completion of the slide process parameter input action. Such may occur at least about one hour after the input, at least about three hours after the input, at least about eight hours after the input, at least about one day after the input, at least about two days after the input, and at least about one week after the input.

As mentioned briefly above, once the information is either monitored or captured, the present invention may act to automatically inform at least one person who may find the information useful. The automatic notice element 404 mentioned earlier may be configured to act as an automatic exteriorly-consequential information notice element by relating largely to that type of information. Of course, the automatic notice element 404 may act in response to the step of monitoring the particular information involved. For example, if it is monitoring operationally-altered outside information, the automatic notice element 404 may act as an automatic operationally-altered outside information notice element. For process events that are merely captured and not automatically monitored, a person may prompt the system upon which it may provide information by some type of display 415. This display (in its broadest sense) may reveal at least some information, perhaps relative to sample process operations to at least one person. If the display reveals significant process detail information, it may be considered as a significant process detail information display. Further if it displays at a separate location there may even be a significant process data transfer element to facilitate remotely displaying such information. As such the display 415 may be considered a remote process detail information display. As mentioned earlier, the system may provide for a real time information display, that is a display that reveals information at about the time it occurs. By real time displaying information remotely, the operator or any other interested person may be able to "watch or monitor the progress of the instrument from another location—perhaps even the other side of the world. This may be particularly valuable when there is a real time display of individual slide log data as mentioned above.

One type of display 415 that may be noteworthy is the fact that embodiments of the invention may create a simulated motion display. The simulation may visually show an element moving on a screen just as the robot head actually moved when it operated as well as the transfer of fluids in the system and perhaps the quantities and status of reagents on the system. Embodiments can provide sequential playback capability so that one could also "watch" the instrument just at it operated at some earlier time. There may also be an altered speed sequential playback capability, a user alterable speed sequential playback capability, or merely a high speed sequential playback capability perhaps all with or without pause or slow motion capability. With this capability, the display 415 may represent a simulated motion process detail information display. The system may thus include a sequential playback element, an altered speed sequential playback element, a user alterable speed sequential playback element, and a high speed sequential playback element.

Any interested person may have the information available to them, such as an operator (e.g., anyone responsible for all or a portion of a process or the instrument), an instrument operator (e.g., an individual physically responsible for all or a portion of a process), an administrator (e.g., a person managing operators or perhaps responsible for order placement), a substance or other supplier, or even a manufacturer, such as for support and maintenance capability. For events that may require external actions (e.g., ordering more reagent or the like), the system may automatically notify at least one of these types of people and thus the automatic notice element 404 (such as a display which may be visual or otherwise) may be considered as representing an automatic operator notice element, an automatic administrator notice element, an automatic supplier notice element, or an automatic manufacturer notice element. It may also be considered as representing an automatic operator exteriorly-consequential information notice element, an automatic administrator exteriorly-consequential information notice element, an automatic supplier exteriorly-consequential information notice element, or an automatic manufacturer exteriorly-consequential information notice element.

Notice may be given at a variety of times. The system may act to automatically advance notify a person such as of an upcoming expiration date or of a need to reorder in advance. In so doing it may have or have input to it some type of lead time information that tells it how early to take the action. By properly configuring a lead time information data element 416, lead time may vary by location and situation, for example a machine around the world or used continuously for critical processing may have a longer lead time than a machine right next to a supplier or used only sporadically. Order lead time information, reagent order lead time information, maintenance lead time information (any of which may vary over the course of a year or from time to time) may be utilized and as such the lead time information data element 416 may represent an order lead time information data element, a reagent order lead time information data element, or a maintenance lead time information data element.

Notice itself may be displayed in a variety of ways. In some embodiments, the system may automatically E-mail a person through inclusion of an E-mail notice element; it may automatically print out (including faxing) a notice by having an automatic printout notice element. Among other embodiments, it may automatically utilize a telephone line for simulated or reproduced voice or other information by having an automatic telephone line utilization element.

The actual event of providing notice may be automatic or it may by caused by some type of user prompt 417. By accepting a monitored information user prompt the system may represent a monitored information user prompt. The prompt itself may comprise a software selection or click-on items such as a software displayed button or the like. Whether displayed and acted upon remotely or at the actual robot-containing housing, such a user prompt 417 may cause a remote access connection to be established and as a result at least some significant process data may be displayed. In such a manner the user prompt may represent an information access prompt element, a software selection element, or a remote access element.

In some embodiments, the system may be comprised of independent or perhaps redundant slide staining modules (some embodiments may comprise eight modules) as shown for some embodiments in FIGS. 1A and 3. Throughput may be based on the time to first result with the system allowing access to completed slides as soon as a staining module has completed the scheduled staining tasks. The multiple independent or redundant staining modules may allow for both continuous and group processing of slides. Additionally, each independent staining module may also allow for the independent pre-treatment and staining of each slide. A carrier retainment assembly, such as a slide retainment assembly, may be used to introduce slides to be processed into the drawer 100, the drawer, slide retainment assembly, and components thereof forming a stain module. The slides may occupy one or more positions of the slide retainment assembly, such as at carrier retention devices, up to the capacity of the slide retainment assembly with the potential for each slide being processed independently of other slides configured with the slide rack. Embodiments of the stain modules, drawers, slide racks, and components thereof are also shown in FIG. 3. FIG. 3 also provides other embodiments of system features, such as an embodiment of the robot arm 20 and the component features of the arm.

Slide retainment assemblies having one or more slides and even reagent containers may be introduced into the staining or reagent modules by introduction into drawers 100 one at a time or in any combination until all or an appropriate number of staining modules are appropriately occupied. There may be no restrictions as to the order, number or timing of when the slide retainment assemblies are introduced into the system, the system may also allow for adaptive scheduling of sample loading. Staining modules, and in some embodiments the drawers of the staining modules, may lock out access to the slides during the processing period and may release them to the operator upon completion of the staining or other process on the last slide of that module. In some embodiments, the order in which the slide retainment assemblies are released may be dependant on the time required to process the last slide of the retainment assembly. Slides may even be processed in the most time efficient manner independently of the order to which they were introduced into the system. The system may provide an optimum or merely an enhanced temporal scheduling of the various sample process steps. To accomplish this, the system may automatically schedule steps that are interspersed for an enhanced time result. This interspersing may be an interleaving of a number of process operations and even an interleaving of a number of individual sample operations. In addition to interleaving steps, the system may sequence the individual sample operations. Regardless as to how programmed, it may be configured through hardware or software or a combination of each to provide an enhanced temporal scheduler element 179, a process operations interleave element, an individual sample operations interleave element, or even an individual sample operations sequence element. These can be created by integrating the automated process operation capability and either the parameter data or perhaps some replicated portion of that parameter process data (as mentioned later) and can thus act to create an interspersial robotic and fluidic control functionality 175.

Slide retainment assemblies having one or more slides may be introduced into the staining modules by introduction into drawers 100 one at a time or in any combination until all staining modules are occupied. There may be no restrictions as to the order, number or timing of when the slide retainment assemblies are introduced into the system, the system allowing for adaptive scheduling of sample loading. Staining modules, and in some embodiments the drawers of the staining modules, will lock out access to the slides during the processing period and may release them to the operator upon completion of the staining process on the last slide. In some embodiments, the order in which the slide retainment assemblies are released is dependant on the time required to process the last slide of the retainment assembly. Slides may be processed in the most time efficient manner independently of the order to which they were introduced into the system.

The control of the processing samples may be accomplished according to the following embodiments, one embodiment shown in FIG. 39, although other processing may be accomplished consistent with the present invention.

Control of the sample processing may be accomplished by and in some embodiments, in accordance with the continuous or group processing previously described. The processing sequence may be controlled, in some embodiments, such that the various steps of a protocol for samples may be automated by one or more algorithmic controls. An example control may be accomplished as follows: 1) selecting a first protocol step, 2) selecting a second protocol from a restricted list of menu items that are compatible with the first protocol step, and 3) selecting subsequent protocol steps from a restricted list of menu items that are compatible with the preceding protocol step.

As shown in FIGS. 43 & 44, in expanded systems, a sample processing system manager, such as a computer server may be connected with a number of individual sample processing systems. These may represent automated slide stainers, stand alone automated slide processing system, or sample analysis systems such that they are fully capable of functioning with connection to other devices. In systems where a connection does exist, the capability of electronically connecting a number of automated slide stainers or automated sample processing systems or label printers 186, may be provided. As mentioned earlier, there may be one or more separate full function computers connected. These may be connected through a hub or router 193. The hub 193 may also provide connection to a Wide Area Network (WAN) or a Local Area Network (LAN) such as through a network bridge. In some embodiments, WAN or LAN may include the Internet.

There may be a multitasked central processing unit resource on either the staining apparatuses 1 or the computer or there may be a number of central processing units that are configured to avoid using or implementing a multitasked central processing unit resource relative to the process operations in order to maintain full independence or perhaps even autonomous operation. The connection, whether for input or other operation may also be a remote link (including ability to be made remote such as in detachable memory) such as an internet connection element, a telephone line connection element, a wireless communication element, or even a detachable memory element. In an embodiment, connection among perhaps a number of process systems and perhaps a number of computers, such as workstations and a server (the latter residing either separately or as part of a workstation), may be achieved by use of a WAN or LAN, such as a group of computers and associated devices that share a common communications line or perhaps wireless link and may even share the resources of a single processor, memory, or server within a small geographic area (for example, within an office building or complex).

A LAN or WAN for this type of system may also include features such as but not limited to: an Ethernet element, a token ring element, an arcnet element, a fiber distributed data interface element, an industry specification protocol, a bluetooth-based element, a telecommunications industry specification using a frequency band of 2.45 GHz, a communication specification applying an IEEE 802 standard, a frequency hop communication specification, a shared common link element, a transmission control protocol/internet protocol communication element, a packetized information protocol, a shared protocol, a proprietary protocol, and even a layered protocol exchange system. Wireless networking function may allow network hub 193 to support the IEEE 802.11b and/or IEEE 802.11g and/or other wireless networking protocols according to some embodiments of the present invention, and serve as a Wireless Access Point (WAP).

Communication between the staining apparatuses and/or with remote users 181 through the stainer network 184 may also occur using standard protocols such as TCP/IP, or any other protocol according to some embodiments of the present invention. A remote user or remote device may query or communicate with any staining apparatus 1 through stainer network 184. In some embodiments, communication between stainers and/or communication over the stainer network 184 may be encrypted. By providing an electronic connection 176 between various resources, the WAN or LAN such as the stainer network 184 (a network dedicated to only the stainer or perhaps sample processing resources for integrity, security, and other purposes) in one embodiment may transmit a electronic memory address to achieve access to the appropriate information. Connection may also be established to a lab network, facilities intranet system, or even a lab information system 195 such as through a bridge 194 or even a router or other LAN connectivity device.

In some embodiments, staining apparatuses 1 may also be connected to one or more computing devices 181 containing removable media drives capable of reading removable media. Removable media may be a floppy disk, CD-ROM, DVD-ROM, DVD+RW, DVD-RW, or any other computer readable media according to some embodiments of the present invention. Computing devices 181 may contain network and communication ports including, but not limited to, USB, Ethernet, Serial, and/or Parallel ports to allow communication with staining apparatuses 1 and LAN or WAN through network hub/router 193 and/or network bridge 194 using appropriate communication devices, methodologies, and protocols according to some embodiments of the present invention. Computing device 181 may also contain one or more of processors, memory, hard disks, graphics cards, and display and data entry devices according to some embodiments of the present invention. Examples of computing device 181 include PCs, Servers, Workstations, Laptops, Handhelds, or any other mobile computing devices capable of being used in stainer network 184

The apparatus may further include means for communicating with proprietary networks such as a LIS. A proprietary network is any network such as in a laboratory, research center or hospital. Examples of proprietary networks include a LIS, which as used herein includes, laboratory information management systems (LIMS), laboratory information networks (LINE), analytical information systems and other laboratory information networks known and used in the art. Examples of means for communicating include software agents as described herein, plug-ins, and application programming interfaces. Computing device 181 may run other laboratory information systems (LIS) according to some embodiments of the present invention. The LIS may use, store and update data, for example, in a database and also request information from stainer related applications running on computing device 181 or from the staining apparatuses 1 directly. In some embodiments, the LIS may store patient records and other lab related data. In some embodiments, a user may import patient data and slide orders into the System Manager from the LIS through an intermediate interface called an "LIS Agent." In some embodiments, the LIS Agent will facilitate the exchange of data between the staining apparatus 1 and related software systems and the LIS. In some embodiments, the LIS Agent may be software that provides a bidirectional interface to receive and send data to other software such as software running on staining apparatuses 1, computing devices 181, or laboratory devices (e.g., slide imaging (ACIS), microtome, tissue processor, special stains automated stainer, in-situ hybridization stainer, fluorescent in-situ hybridization stainer, flow cytometer, flow cytometer analyzer) 186.

For example, information about reagent and/or bulk fluid usage could be conveyed to the LIS and supplies ordered whenever the inventory level falls below a certain threshold. In some embodiments, re-ordering of supplies may take place according to a prearranged subscription plan. In some embodiments, the LIS could also keep track of diagnostic messages and/or error codes from staining apparatuses 1 and automatically schedule service. In some embodiments, the LIS could use stainer and slide related information to perform accounting functions, including the generation of invoices and reports. In some embodiments, the LIS use stainer and slide related information stored in databases, for example, to generate cost and usage statistics relating to the operation of the stainers. It should be noted that system depicted FIGS. 39, 43 and 44 is exemplary only and additional stainers, computers, servers, lab devices and other components may be added to the system in order to perform methods and achieve objects and functionality of the system.

Figure 45:
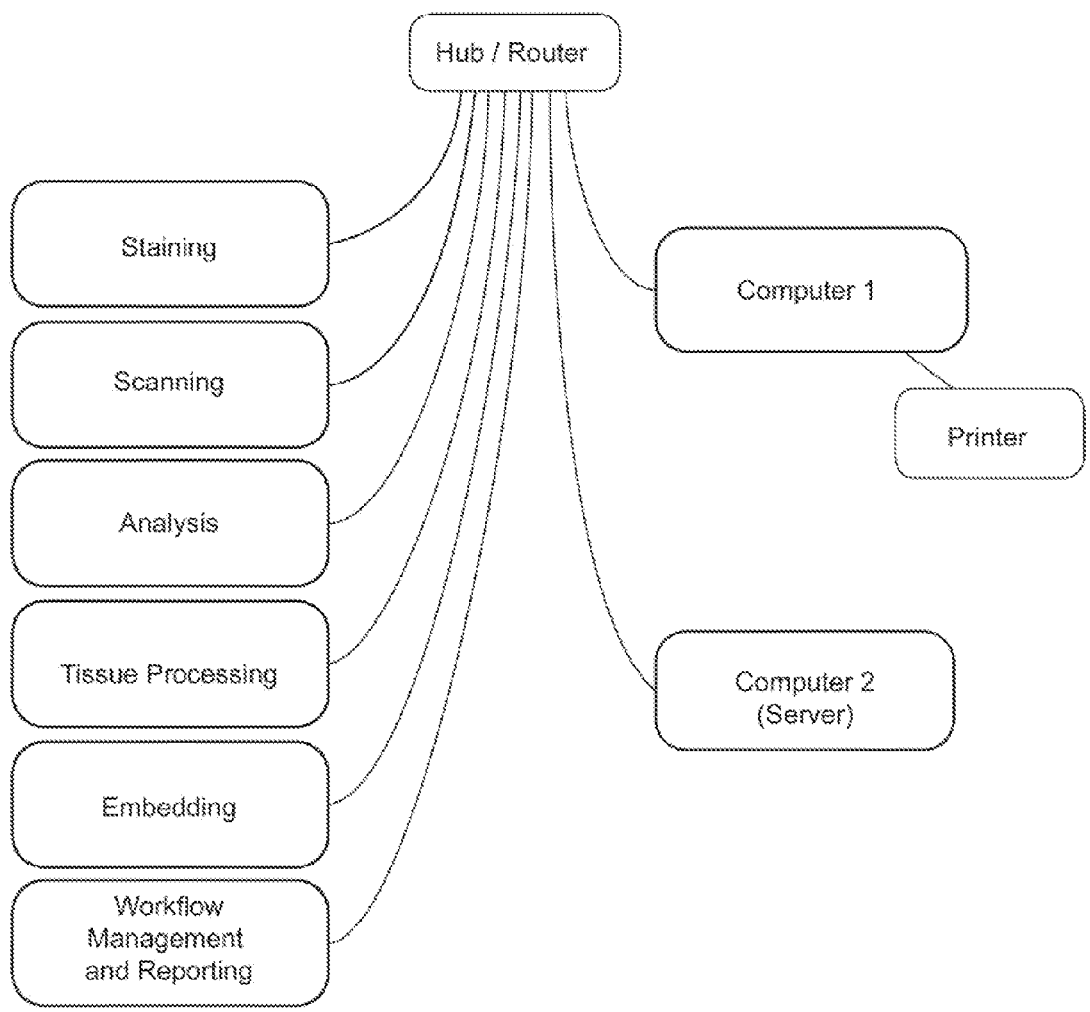
FIG. 45 illustrates an example network connecting various sample processing systems representing various functionalities together, according to certain embodiments.

In certain embodiments, various sample processing systems can be connected in a network. These sample processing systems can represent devices of differing functionality brought together through a network, e.g., to share information. Examples of various sample processing systems include instruments related to tissue samples on a laboratory glass slide in a pathology lab. These instruments may facilitate functions such as tissue processing, embedding, staining, slide scanning, analysis of slides, and workflow management and reporting. For example, as illustrated in FIG. 45, various sample processing systems representing various functionalities can be connected together through a network.

As mentioned, connection may be accomplished over internet connections but, in one embodiment, is accomplished over local area network connections. Each sample processing system may be individually controlled, in some embodiments, by a PC attached with, internal to, or otherwise provided. Data sharing between sample processing systems and the system manager may be performed to allow identification, tracking, and status of sample groups, reagents, and other agents and components of the sample processing system. A determination of which system has which reagents, reagent type, slides and protocols may be performed. Log files for each processing sequence, protocol, or slide can be generated for monitoring processing status. Database maintenance (including but not limited to purge, compact, backup, database list, and archive functions) and system diagnostics (including but not limited to exercising active system components to verify proper operation and assisting in troubleshooting efforts) may be accomplished manually or automatically.

The system may be configured to automatically access the required data through operation of the process operation control system 171 by inclusion of an automatic memory access element. This access may be achieved by specifying an electronic memory address that may be transmitted by an electronic memory address element 178 perhaps over a local area network and may be followed by automatically replicating that data on some a memory aspect appropriate for operation such as an automatic data replication memory. This memory may include but not be limited to: a volatile memory functionality as implemented by a volatile memory element, a random access memory functionality as implemented by a random access memory element, a non-volatile memory functionality as implemented by a non-volatile memory element, an electrically erasable programmable read only memory functionality as implemented by an electrically erasable programmable read only memory element, a main storage functionality as implemented by a main storage element, a secondary storage functionality as implemented by a secondary storage element, a cache memory functionality as implemented by a cache memory element, and even a detachable memory functionality as implemented by a detachable memory element.

A control interface may be provided for the operator, such as a graphical user interface (GUI), and may accommodate various languages. Help menus may be provided to assist in sample processing. Password protection features can be provided and even administrator control over at least some aspects. This may include the capability to include administrator limitations on the functional availability of any aspect of the system or of specific stainer availability or functionality, certain reagent availability functionality, certain protocol availability functionality, patient identification information access functionality, process priority request functionality, and immediate, urgent, or stat process request functionality. By including an administrator control element 180, the system may have an administrator-implemented user limitation element, a specific stainer availability limitation element, a certain reagent availability limitation element, a certain protocol availability limitation element, a patient identification information access limitation element, a process priority request limitation element, an immediate, urgent, or perhaps stat process request limitation element, a user privileges input element, and even a user group privileges configuration or input element.

Control of the sample processing may be accomplished by and in some embodiments, in accordance with continuous, or group processing previously described. The processing sequence may be controlled, in some embodiments, such that the various steps of a protocol for samples may be automated by one or more algorithmic controls. As part of input to establish the desired control functionality, user or other input may be accommodated as follows: 1) selecting a first protocol step, 2) selecting a second protocol from a restricted list of menu items that are compatible with the first protocol step, and 3) selecting subsequent protocol steps from a restricted list of menu items that are compatible with the preceding protocol step.

After all data is inputted, the system may act to determine operational readiness by inclusion of an operational readiness determination element 177 that may be programmed to assess if appropriate resources, drawers, slides, reagents, fluids, or other aspects are present or available to the system. As mentioned above it may notify an operator of a need if any exists. Once an appropriate operational readiness is determined, the system may prompt initiation of access of the input data to electronically determine operational availability of a variety of items. These may include but are not limited to: an individual sample element through inclusion of an individual sample readiness determination element, a defined group of samples through inclusion of a defined group of samples readiness determination element, a physically grouped collection of samples through inclusion of a physically grouped collection of samples readiness determination element, a slide drawer component through inclusion of a slide drawer component readiness determination element, a stand alone automated slide processing system through inclusion of an stand alone automated slide processing system readiness determination element, a slide stainer system element through inclusion of a slide stainer system readiness determination element, and even a user initiated prompt signal such as might occur to force or activate the system manually by the inclusion of a user initiated prompt signal determination element.

There may even be timing tolerances, referred to in some embodiments as "bubble tolerance", that may be controlled as between steps, such as between aspiration cycles. Additional control may be accomplished through timing algorithms to determine time tolerances of components of the processing system, such as the monitoring of "shelf life" or viability of reagents. Furthermore, adaptive scheduling of sample and slide insertion and removal into the system, as previously described, may be accommodated on an ongoing basis throughout operation of the sample processing system.

Figure 46:
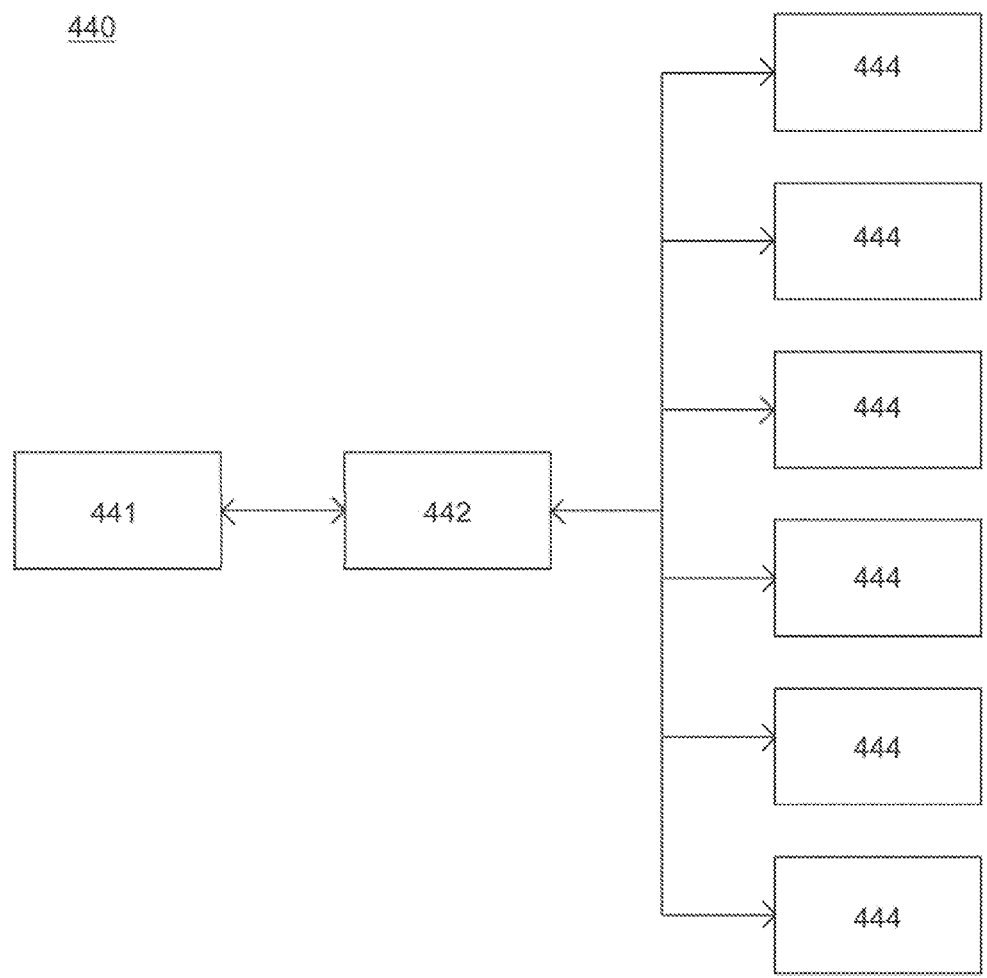
FIG. 46 illustrates an example control system to facilitate autonomous operation of a sample processing system, according to certain embodiments.

FIG. 46 illustrates an example of a control system 440 to facilitate stand-alone, or autonomous operation of a sample processing system. The control system 440 can, in certain embodiments, comprise a host processor 441, such as, e.g., a personal computer, coupled to a master control board 442. In certain embodiments, the connection between the host processor 441 and the master control board 442 can be a fast data transfer connection such as a PC 104 connection through a system bus such as, e.g., an ISA bus. The fast data transfer connection can facilitate the transfer of data between the host processor 441 and the master control board 442. In certain embodiments, the master control board 442 can be physically located within the respective sample processing system. In certain embodiments, the host processor 441 can send commands to the master control board 442, e.g., to program the master control board 442 to operate in an autonomous manner.

In certain embodiments, the master control board 442 can couple to one or more slave control boards 444 through many different possible connection standards such as, e.g., a high-speed serial connection. The slave control boards 444, in turn, are coupled to one or more individual components within the sample processing system such as, e.g., pumps, valves, solenoids, fluidic systems, robot operation, LCD interface, fan monitors, drawer assembly control, and the like. The slave control boards 444 may be able to quickly transfer data between the individual components and the slave control boards 444 to facilitate control of the individual components. In certain embodiments, this configuration enables the slave control boards 444 to control tasks that are time-sensitive and/or tasks that would need an immediate response. In certain embodiments, higher-level commands can be transferred by the host processor 441 to the master control board 442 and then on to the respective slave control boards 444.

Figure 52:
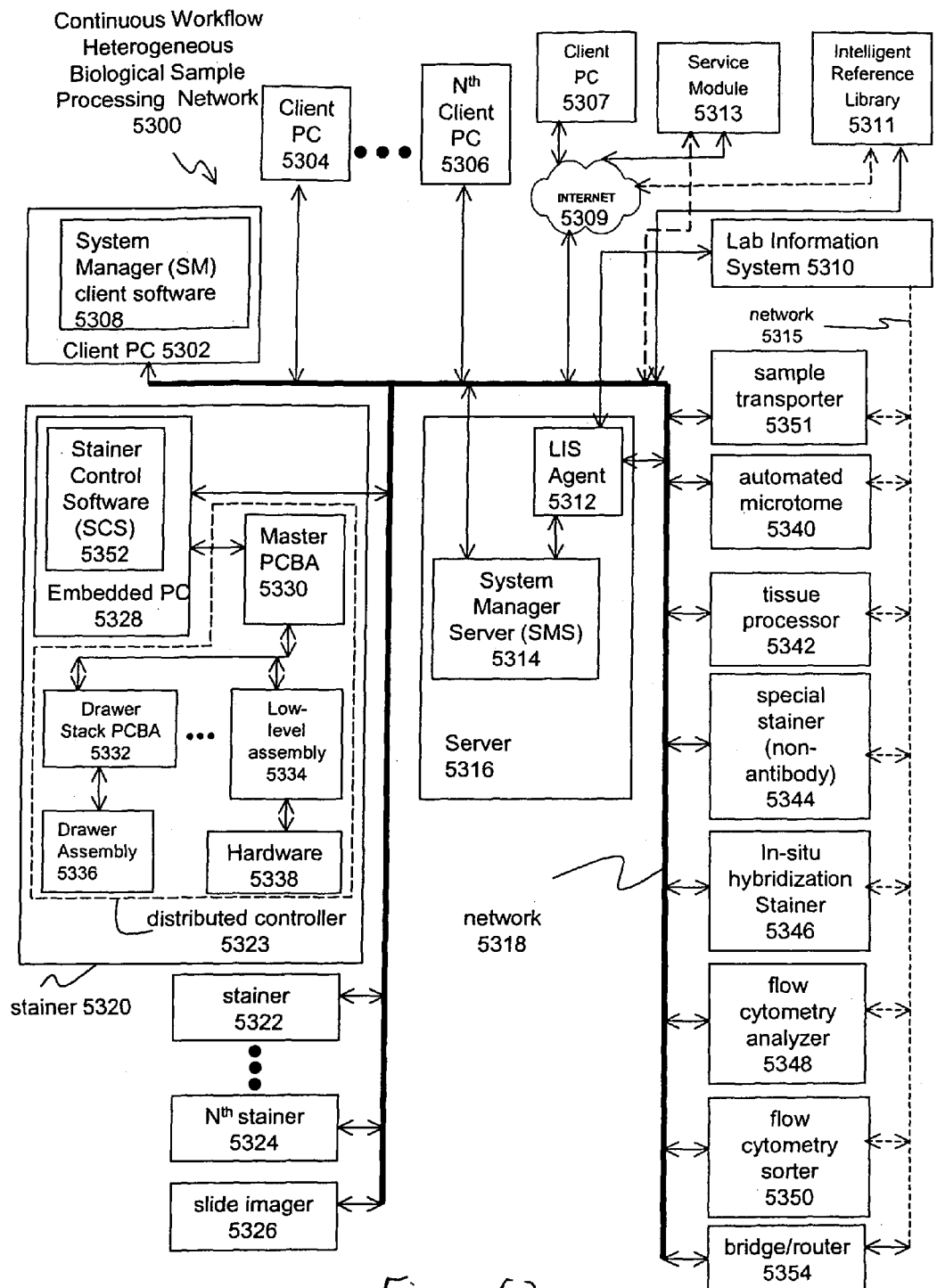
FIG. 52 illustrates an embodiment of a continuous workflow heterogeneous biological sample processing network

FIG. 52 illustrates an embodiment of a continuous workflow heterogeneous biological sample processing network 5300. One additional embodiment of the invention is a continuous workflow biological sample apparatus. A server PC 5316, which includes System Manager Server (SMS) software 5314, is connected to a network 5318. Network 5318 may be an Ethernet 10/100 base T network, a wireless network, such as 802.11b, or any desired network. For purposes of this application, server 5316 may be implemented on a specific computer or on a plurality of computer such as a cluster. System Manager Server (SMS) 5314 communicates via network 5318 with Stainer Control Software (SCS) 5352 that controls and monitors various pre-treatment, processing and staining functions that are implemented on a first stainer 5320.

Other stainers such as a second stainer 5322, or any desired number of stainers up to an Nth stainer 5324, may be connected to network 5318 so that System Manager Server (SMS) software 5314 may communicate with any of the stainers 5320, 5322, and 5324 that are connected to network 5318. A network 5318 that connects a System Manager Server (SMS) 5314 to only stainers may be thought of as a homogeneous network, i.e., a network that connects a server to processing apparatuses of the same type in accordance with one embodiment of the invention. An additional embodiment may include more than one network i.e., one dedicated LAN and perhaps a LAN of a remote laboratory which may be further connected via a router an/or a bridge device. This may also provide connectivity to the LIS Agent 5312. Additionally, client capability interactivity, such as for personnel deployment, may be realized via the remote LAN of a laboratory, for example, which may also access the SMS.

In the embodiment of FIG. 52, a heterogeneous biological sample processing network 5300 may be implemented, i.e. a network that connects a System Manager Server (SMS) 5314 to different types of instruments. For example, network 5318 may connect to sample processing equipment such as slide image 5326 which may be a slide imager such as the ACIS family of imagers from CLARiENT, Inc, San Juan Capistrano, Calif. Other instrument types related to sample processing may include an automated microtome 5340, tissue processor 5342, special stainer 5344, and in-situ hybridization stainer 5346.

Still other types of instruments, such as flow cytometry analyzer 5348 and flow cytometer sorter 5350 may also be adapted to connect to server 5316 and to System Manager Server (SMS) 5314. Each of the different instruments 5326, 5340, 5342, 5344, 5346, 5348, 5350, may be equipped with desired network hardware and software that enables System Manager Server (SMS) to request data from or send data to any instrument that is connected to network 5318.

For example, if a labeled or otherwise uniquely identified slide that has been previously processed by stainer 5322 is moved to slide image 5326 so that the stained slide may be imaged, slide imager 5326 may query its own internal records and find that no record of the slide is contained. Upon determining that no record of that particular slide exists, slide imager 5326, which is connected to server 5316, may query system manager server (SMS) 5314 to determine if a record exists within SMS 5314. A record of the slide may have previously been stored in SMS 5314 at the time the slide was processed on stainer 5322. Thus, the query from slide imager 5326 may result in a record being found whereupon a record identifier or data from that record within SMS 5314 may be transfer to or referenced by slide imager 5326.

Another example may be that samples of different types from the same patient case such as a tissue sample and a flow sample may processed and/or analyzed by various instruments connected to network 5318 and subsequently be correlated or linked via System Manager Server SMS 5314.

This automated network transfer of data between various heterogeneous instruments connected to network 5318 provides numerous advantages over traditional methods. One advantage is the reduction or elimination of user-caused data entry errors that occasionally occur when data is entered manually. A second advantage is that the time required for transferring data automatically via network may be hundreds or perhaps thousands of times faster than manual data entry. A third advantage of a heterogeneous network is that a user that is using a Client 5302 that is running System Manager (SM) 5308 software may connect to and transfer data to and from System Manager Server 5314. For example, an image that is store locally on slide imager 5326 may be linked via network to an entry with a database on System Manager Server (SMS) 5314. A pathologist or a lab manager who is looking at stainer-related data for a particular slide that has been stained on stainer 5320 may select to view an image for that same slide which as also been imaged on slide imager 5326. The slide image data may remain on slide imager 5326 but may be transferred temporarily to SMS 5314 and from there to an SM 5308 application that is running on Client 5302.

Server 5316 may further include a Lab Information System (LIS) Agent 5312 that connects to System Manager Server (SMS) 5314 and serves as an interface to Lab Information System 5310. Other instruments such as special stainer 5344 or flow cytometry analyzer 5348 may include software that provides an interface to lab information system 5310 whereby data from those instruments may be transferred to and from lab information system 5310 and from lab information system 5310 data may be transferred to or from SMS 5314 via LIS agent 5312. Thus, other instruments, such as automated microtome 5340, tissue processor 5342, special stainer (non-antibody) 5344, In-situ hybridization stainer 5346, flow cytometery analyzer 5348, flow cytometry sorter 5350 and sample transporter 5351, may gain LIS connectivity through the SMS and a may only use a single LIS Agent in some embodiments. This embodiment may prove useful within industry, for example, by reducing potential extra charges charged by service providers. Such charges may typically be associated or incurred with each additionally connected device connected to respective LIS Agents (in further connection with the LIS) wherein a charge may be accessed per connection to each LIS Agent. Data from slide image 5326, flow cytometry analyzer 5348, or any desired instrument, may also be transferred via network 5318 directly to and from LIS agent 5312 associated with SMS 5314 without the going through lab information system 5310. This provides an advantage in applications where a single connection point to lab information system 5310 is desired, since some lab information system provider have a business model that includes a cost for each connection point.

Additionally, other networks including lab network such as network 5315 may connect to a sample processing instrumentation network, such as network 5318, via a network bridge/router 5354.

Further, network 5318 may include security features such as encryption, password protection, and double entry validation to name a few. Likewise, use of LIS agent 5312 to communicate and transfer data between server 5316 and lab information system 5310 may facilitate security and privacy of patient information. Slides or other sample carriers may be labeled with a patient name or there may be a log book that associates a label with a patient or case. In systems which use manual entry to transfer or associate data between various sample processing and analyzing instruments, each manual transfer is a possible point of a breakdown in the privacy and security of the data. Heterogeneous biological sample processing network 5300 reduces the number of manual data entry points required and thereby improves the security and privacy of possibly sensitive patient data.

Another heterogeneous aspect of the embodiment of FIG. 52 is that clients 5302, 5304, and 5306 may be implemented on different types of client computers. For example, a first client 5302 may be a personal computer that uses an operating system such as Microsoft Windows, while a second client 5304 may be a workstation that uses a different operating system such as Linux, and 3$^{rd}$ client may be handheld computer such as a personal digital assistant (PDA) that is connected to server 5316 via a wireless network connection.

Another aspect of the embodiment of FIG. 52 is that client 5307 may be connected to Network 5318 via "the Internet" 5309, so that SM Software 5308 running on Client 5307 may exchange information with SMS 5314 and manage and monitor instruments such as 5322, 5324, slide imager 5326 and any or even all instruments deployed on Network 5318. Further, multiple remote connected Client PCs can be connected simultaneously to network 5318, and to SMS 5314, via the Internet 5309.

One embodiment of the invention may include a service module 5313 so that a service technician may automatically or manually poll or otherwise communicate with any desired instrument connected to network 5318. Automatic communication of data may be programmed to be initiated by Server 5316 without interaction of a user or service technician. Alternatively, a dedicated support tool, such as SST (system support tool) may be utilized. Automated processes may also be realized such as allowing the server to connect with the support server, for instance, in timed integrals to transmit data (e.g., health information, system dispatch of personnel (such as maintenance operators equipped with necessary parts/equipment to perform repairs and/or maintenance), etc.)

To expand further upon the example illustrated above, upon receiving an error message indicating a fault in hardware 5338, service module 5313 may be used to remotely monitor and diagnose the problem. A service technician may for example send a signal to reset a processor within low level PCBA 5334 to clear a possible firmware error. The distributed and independent operational partitioning of the hardware and electronic assemblies in stainer 5320 facilitates the functional diagnosis of components such as low-level PCBA 5332 which is connected to hardware 5336 which operate substantially independently from low-level PCBA 5334 which connects to hardware 5338. So when low level PCBA 5334 is reset, in some embodiments it may be able to resume function with having interrupted processing functions being executed by independent low-level PCBA 5332.

Any connected remote client, such as client 5302, or alternatively, service module 5313 may include service software that facilitates remote administration of software or firmware service patches and upgrades. System Manager Server (SMS) 5314 may connect to service module 5313. In remote upgrade or patch installation applications, it may be advantageous to use a dedicated secure network connection such as a telephone line with a modem to connect to server 5316 A dedicated, secure connection may reduce the likelihood of a disconnect or interruption in the network connection in the middle of an upgrade or patch installation. Other security measures such as data encryption may be utilized if service module 5313 connects through the Internet 5309 to network 5318 and server 5314.

In the embodiment of FIG. 52, heterogeneous biological sample processing network 5300 may include a sample transporter 5351, i.e., an automated or semi-automated means such as a robotic arm, a conveyor belt, robot, or any conveyance apparatus to transport physical sample carriers, e.g. slides from one instrument such as stainer 5320 to another instrument such as slide imager 5326.

System Manager Server (SMS) 5314 may be programmed with user defined protocols for pre-treatment and processing of samples for each stainer that is connected to network 5318 such as stainers 5320, 5322, and 5324. Further SMS 5314 may collect and log information about the staining and pre-treatment processes of stainer 5320. Further information about the level of reagents and bulk fluidic, the temperature of the various heating and cooling components, may also be stored within SMS 5314. A client such as client 5306 may be used to monitor protocols specified and compare them with the log of pre-treatment ad processing steps that were actually executed. Thereby if a user has concerns about the results of certain staining processes, the programmed and logged processing steps may be examined remotely via network 5318 by a person knowledgeable in staining protocol stationed at a client, such as client 5306, which knowledgeable person may provide suggestions as to how the staining results may be improved.

Similarly, data may be collected automatically or manually from multiple stainers, such as stainers 5320, 5322, 5324, and from other network connected instruments such as slide imager 5326 or any desired combination of instruments. A sample processing instrumentation manufacturer may additional collect and aggregate date from multiple networks. Data useful for determining the reliability of the instruments, such as the failure rates of particular instrumentation components, may be obtained via network 5318 from which the manufacture may take actions to investigate and reduce the failure rate of any desired components.

Likewise, data regarding the usage of certain reagents or combinations of reagents may be collected and aggregated via network 5318 so that frequently used protocols may be optimized as desired. This may allow tracking for billing and perhaps automatic shipping features, such as shipping reagents based upon inventory data submitted, for example, by connectivity and transmittal via the Internet.

A historical reagent usage rate may be calculated to adaptively determine an expected date for when the reagent supply will be depleted, thus a supply purchase order generation application may be implements on server 5316 that places a purchase order for reagents or other supplies in a timely manner so that reagents are available on an ongoing basis without the need for maintaining excess inventory which may be wasted if the reagent expiry date antedates the reagent expected depletion date.

Heterogeneous biological sample processing network 5300 may further comprise an intelligent reference library 5311 that connects to network 5318 that includes analytical databases and tools that support lab personnel and pathologists in using data from some or all of the instruments connected to network 5318. Alternatively, an intelligent reference library, or multiple intelligent reference libraries, may connect to network 5318 via "the Internet" 5309.

Business applications such as monitoring the aspirated and applied volumes of various reagents may be implemented to use data which has been stored during the processing steps by SMS 5314. This may be useful in determining if unauthorized or scientifically imprudent reagent dilution has occurred. A fixed-price per test business model may utilize information stored by SMS 5314 to charge a user on a per-slide basis, thus reducing the economic incentive to dilute reagents. Information such as test counts for per-test billing, or any information may be communicated to service module 5313 via the Internet 5309 or via other network connections.

A reagent provider may also periodically and automatically update reagent lists or recommended protocols from service module 5313 via the Internet 5309 to SMS 5314.

Automated backup and archival applications may be implemented on server 5316 or alternatively on clients 5302 or any clients so that data obtained via network 5318 may be stored for archival and subsequent retrieval.

Figure 53:
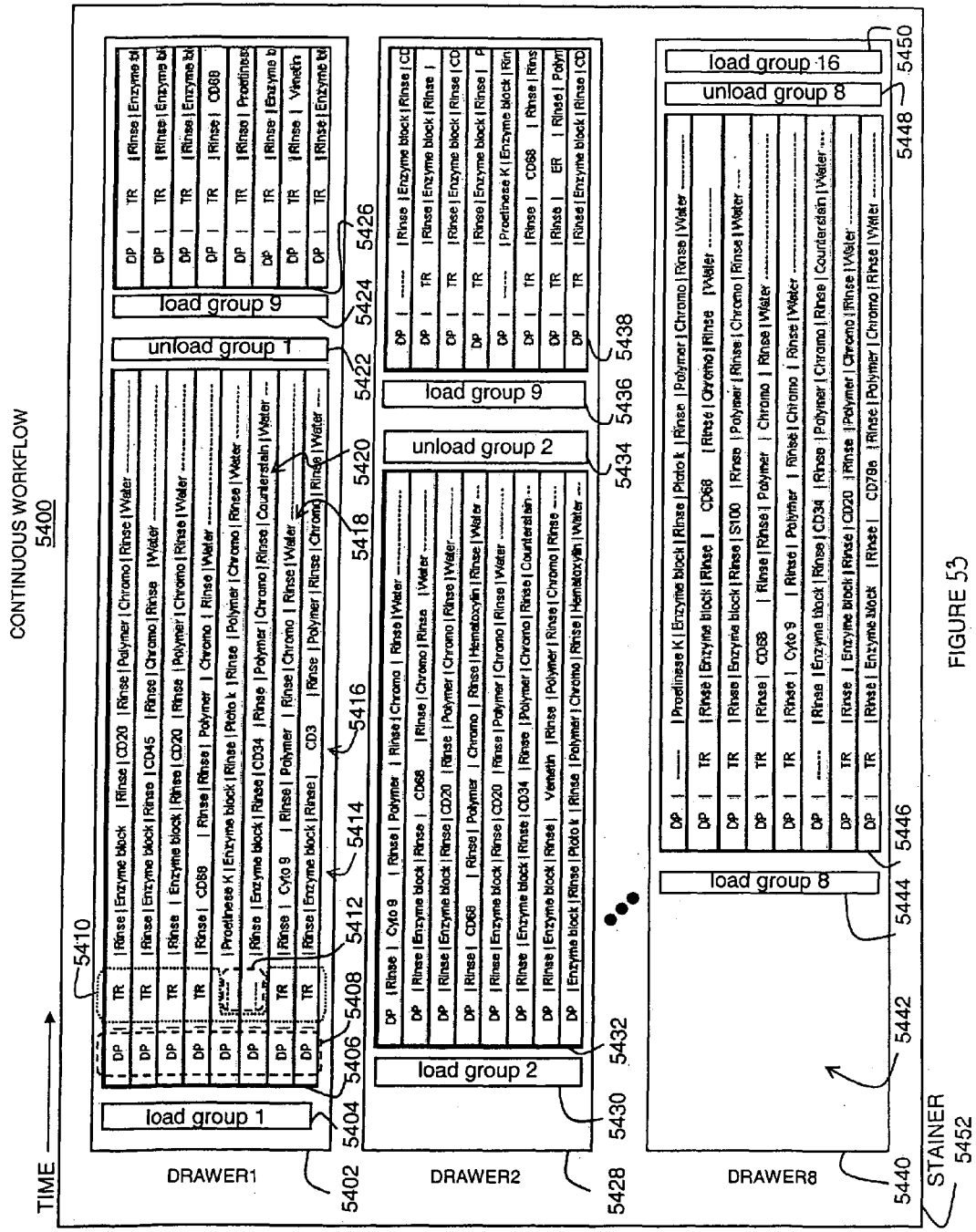
FIG. 53 illustrates continuous workflow provided by an embodiment of the network of FIG. 52

Heterogeneous biological sample processing network 5300 facilitates and enhances the continuous workflow capabilities of stainer 5320. A similar configuration as described herein may be used in a continuous workflow biological sample processing apparatus, e.g., without the heterogeneous network or with a scaled back heterogeneous network. Stainer 5320 may include a distributed controller 5323 which is connected to embedded PC 5328 and that communicates with Stainer Control Software (SCS) 5352. Distributed controller 5323 includes a master printed circuit board assembly (PCBA) 5530 that connects to embedded PC 5328 and communicates with Stainer Control Software (SCS) 5352. Master PCBA 5330 also connects to a bus that connected to distributed electronic and mechanical assemblies such as drawer stack PCBA 5332 and to other low-level PCBAs as represented in FIG. 53 by low level assembly 5334. Various low-level assemblies may comprise distributed controller 5323 as described in greater detail in other sections of this application. One example of an embodiment of the invention that facilitates continuous workflow of the sample processing system is that the network communications provided by heterogeneous biological sample processing network provide a way that diagnostic or service communications and operations may be performed remotely. For example, consider the hypothetical case that drawer assembly 5336 on stainer 5320 that contains slides that are currently being processed and that hardware 5338 is a second drawer assembly that experiences a malfunction such as a faulty fluid level sensor within the drawer. This error which is sensed and interpreted by low level PCBA 5334 which communicates the error status to Master PCBA, which in turn communications the status to embedded PC 5328. Embedded PC 5328 includes a network interface and may be programmed to communicate messages such as en error message from Stainer Control Software (SCS) 5352 to System Manager Server within server 5316. System manager server 5314 may then communicate an error warning message to various clients such as clients 5302, 5304, 5306 connected to network 5318. These messages may also be transmitted via the internet 5309 to a client such as client 5307 or to a service module 5313.

Timely communication of error conditions via heterogeneous network 5300 facilitates continuous workflow in that when a lab technician, lab manager, or a remote service technician, or any user of the stainer or other processing instrument is notified of an error condition, such a user may take appropriate actions that facilitate continuous workflow such as sending a reset command to low-level assembly 5334 which may clear a software or hardware error condition while simultaneously allowing another element of the distributed controller 5323 such as drawer stack PCBA 5332 to continue processing according to the programmed protocol, thus the continuous workflow of stainer 5320 is facilitated and enhanced.

The facilitation and enhancement of continuous workflow of the invention is not limited to fault tolerance and isolation of anomalous conditions. For example, drawer assembly 5336 may have slides or other biological sample carriers that have samples for which all desired and programmed processing has been completed. The processing completed status of the sample may be detected by the combination of drawer assembly 5336 and drawer stack 5332. whereupon such status is communicated to Master PCBA 5330 which in turn communicates completed status to stainer control software (SCS) 5352 within embedded PC 5328. This information is then transmitter via network 5318 to SMS 5314 within server 5316. SMS 5314 may then send a "processing completed" message to client 5302 or to service module 5313 or any to client on network 5318 or on the internet 5309, thereby notifying a user or multiple users of the processing completed status of the slides or samples within the drawer assembly 5336, whereupon a lab technician or other user may timely remove the samples that have completed processing from drawer assembly 5336, and may immediately place a new batch of samples for processing into drawer assembly 5336. The new batch of samples may then begin processing automatically or upon a signal from the user. The user may program automatically starting processing or manual send a manual process start signal via a user interface within stainer 5320 or via a client or service module connected to network 5318.

Thus notification of error conditions associated with a first group of samples and facilitation of real-time correction of such error conditions simultaneous with normal continuous workflow processing of a second group of samples, along with the ability to notify users via network communications of processing completed status of a first group of samples simultaneous with the normal processing of a second group of sample are just two of the many ways in which the unique continuous workflow processing of samples may be facilitated and enhanced by the heterogeneous biological sample processing network 5300. Similarly, network communications may be used to notify a user that a reagent or group of reagents should be removed, added or replaced. This timely notification via network communications in combination with other electrical and mechanical components of stainer 5320 greatly facilitate and enhance continuous workflow operation of the stainer.

Likewise, network communications between server 5316 and a second stainer or any number of stainers, or related sample processing instruments, further enhances continuous workflow. For example, the processing completed status from a drawer assembly 5336 within stainer 5320 may be transmitted to a second instrument such as slide image 5326 and a client 5302 may be notified, whereupon a user, or an automated sample transporter may transfer the sample carrier, e.g. slide, from the stainer 5320 to slide imager 5326. Data from the sample carrier which had previously stored in server 5316 may be automatically forwarded or link to data from the second instrument, e.g. slide imager 5326. Thus, again the timely network communications capabilities of heterogeneous biological sample processing network 5300 facilitates continuous workflow processing of samples.

Embedded PC 5328, which is connected to network 5318, communicates with server 5316. For example, System Manager Server (SMS) 5314 may be programmed to send a message activating a warning in one or more of the clients. For example, client 5306 may a portable client such as a cellular telephone, PDA, or pager, which, upon receiving a warning message causes an aural or vibratory alert. System manager server (SMS) 5314 may also be programmed to send a message to outside service entities via a modem or Internet 5309 connection to alert service personnel of a problem including specific diagnostic data relevant to the problem. Instrument health and diagnostic information may be automatically transmitted at programmed intervals to a service module 5313 which connects to SMS 5314 via the Internet 5309 or via dedicated connection to network 5318.

Thus, the heterogeneous combination of hardware and software components of the invention provides unique advantages of integration of various sample processing instrumentation including a server 5316 that has a system manager server 5314 that may connect to multiple stainers 5320, 5322, 5324 and to various non-staining instruments such as slide imager 5326. Further, multiple clients 5302, 5304, 5306, which may be of similar or different types, may connect to server 5316 to send or receive control commands, captured or recorded data, and to monitor and access instrumentation components remotely.

FIG. 53 depicts an embodiment illustrating continuous workflow 5400 supported and implemented by at least one embodiment of stainer 5452. Stainer 5452 includes a first slide processing drawer, drawer1 5402, a second slide processing drawer, drawer2 5428, other slide processing drawers, drawer3 through drawer7 (not shown), and an eighth slide processing drawer, drawer8 5440. For purposes of this application, a drawer may be defined to be any holder, container, tray, rack, carrier, or other conveyance, that may be at least partially removable and is loadable and unloadable with at least one sample carrier, e.g. slide.

In the embodiment of FIG. 53, drawer1 5402 includes a slide rack capable of holding up to eight slides. A user of stainer 5452 may open drawer1 5402 and load a first group of slides, e.g. a user may perform a manual operation, load group 1 5404, by loading slides to be processed into each of eight positions available for slide processing and then closing drawer1 5402.

Stainer 5452 may be programmed to automatically begin processing the slides within drawer1 5402 shortly after the user performs the load group_1 5404 operation and closes drawer1. Alternatively, a manual user intervention step may be required such as requiring the user to interactively accept drawer1 via a computer user interface.

A set of protocols 5406 may have been previously programmed or selected by user for each slide within drawer1 5402. Protocol steps may include pre-treatment steps such as deparaffinization 5408 for samples that have undergone Formalin-Fixed, Paraffin-Embedded (FFPE) fixation and embedding processes. Once the paraffin has been removed and the slides have undergone re-hydration, as described in other sections of this specification and in applications incorporated by reference, additional processing steps may be initiated such as target retrieval 5410, also known as antigen retrieval. In some cases, some of the slides in drawer1 5402 may be programmed to undergo antigen retrieval 5410, while other slides may be programmed to bypass 5412 antigen retrieval. In the embodiment of FIG. 53, steps such as deparaffinization 5406 and antigen retrieval 5410 may be performed with the slides being rotated to a vertical position and being at least partially immersed in a processing tank designed to perform deparaffinization Protocol steps that occur in a processing tank such as deparaffinization 5408 and antigen retrieval 5410 may be scheduled by the fluidics scheduler which has been described in other sections of this specification.

Additional steps such as endogenous enzyme blocking 5414 may be performed, or not performed, depending on the programmed protocol for each slide. Various other steps such as application of reagents 5416, including reagents with antibodies, may be executed in a pre-determined order. Multiple reagents may be applied together or sequentially and rinsing with a buffer solution may occur between each step. Application of a chromagen 5417 or other staining processed may then occur. To keep a slide hydrated, rinses with buffer solutions or de-ionized water 5418 may be programmed to occur periodically so that the samples remain hydrated. This is especially useful when certain slides within a drawer have longer protocol than other slides within the same drawer, for example, processing of a slide which includes a counterstain 5420 step may take longer than processing of a different slide which does not include a counterstain step. Steps such as enzyme blocking, reagent/antibody application, chromagen application, buffer rinsing, de-ionized water rinsing, or any desired step which is executed by the robotic probe 10 which has been described in other sections of this specification, are generally executed by the robotics scheduler. The order of execution of steps handled by the robotics schedule is adaptive and non-deterministic. In other words, the robotics schedule does not plan out and pre-determine the time for multiple future steps for multiple slides, rather each slide may be represented in the software as a virtual object. Within each slide object may be a list of protocol steps to be executed. The robotics scheduler and associated software may further include rules or algorithms for polling and monitoring each slide object and determining an optimal execution priority and order for a slide or group of slides.

When the set of programmed protocol steps 5406 for all slides within a drawer, such as drawer 5402 have completed, stainer 5452 may be programmed to signal the user that processing for that drawer 5402 has been completed. This signal may be an aural or visual signal emanating from the hardware of stainer 5452 or the completed status may be communicated to a remote server or client computer which may then emit or otherwise provide a similar signal. Whereupon, a user may then perform an unload group_1 5422 operation, i.e., unload the slides. At this point in time, drawer1 5402 may now be available for processing of an additional group of slides, i.e. a user may now perform another operation, load group_9 5424 with a corresponding set of protocol steps 5426 for that set of slides.

Processing of slides 7 in drawer2 5428 and other drawers on up to and including drawer8 5440 may be initiated and may continue simultaneous with processing of slides in drawer1. In the example of FIG. 53, the loading 5430 of group_2 of slides into drawer2 occurs subsequent in time relative to the loading 5404 and initiation of processing 5406 of group_1 in drawer1 5402. However, the protocol steps for group_2 5432 in drawer2 5428, may not require a target retrieval, i.e. antigen retrieval, such as target retrieval 5410. Therefore, protocol steps 5432 programmed for drawer2 may require less time and therefore complete sooner in time, than protocols steps 5432 programmed for drawer2 5428. Upon completion of protocol steps 5432 for slides within drawer2 5428, a user may then perform an unload operation 5434. When slides have been unloaded 5434 from drawer2, another group of slides such as group_9 may be loaded 5436 into drawer2 5428 and a corresponding set of protocol steps 5438, which may have been previously entered or programmed into stainer 5452, may then begin to be executed.

Other drawers such as drawers 3 through 7 (not shown) may be programmed, loaded, processed, and unloaded according to desired slide processing protocols.

Drawer8 5440 may likewise be utilized. Depending on the number of slides in a queue to be processed, there may be a period of time 5442 when drawer8 5440 is empty and no processing is scheduled. A user may load drawer8 5440 with an eighth group of slides 5444 and a program a corresponding set of protocol steps 5446. When slides in drawer 5440 have completed processing according to protocol steps 5446, a user may unload group_5448 and load a new group_16 5450 of slides for processing in drawer8 5440.

The combination of independent drawers such as drawer1 5402, drawer2 5428, drawer8 5540 and other drawers (not shown) along with software such as robotics scheduler and fluidic scheduler, provide stainer 5452 with unique continuous flow 5400 capabilities. Likewise, as described with respect to FIG. 52, the heterogeneous network further uniquely facilitates and enhances continuous workflow sample processing. For labs that have a high volume of slides, or that have a need to processes certain slides with high priority relative to other slides, the embodiment of stainer 5452 as illustrated in FIG. 53 allows users within the lab to add new slides or groups of slides to stainer 5452 for processing, without causing the concurrent processing of other slides within stainer 5452 to exceed required time limits or guidelines as defined in the protocols. The ability to apply a buffer rinse and/or a de-ionized water rinse according to predetermined or desired rules, especially during interrupts or other non-deterministic delays, enhances the ability of stainer 5452 to keep slides hydrated and usable.

Additionally, the distributed architecture of low-level components such as printed circuit board assemblies used to control the drawers, which has been described in other sections of this specification facilitates the timely sensing, monitoring, updating and control of the various protocol steps by providing rapid and substantially independent processing and control of various fluidic, electrical, and robotic steps, so that the minimum length of such steps is determined by the biochemical process limits defined by the protocols rather than by the ability of stainer 5452 to execute such steps.

Further, certain components of stainer 5452 such as drawer1 5402 may be replaced, i.e., "hot swappable", in the event of a mechanical or electrical failure of drawer 5402 as described in other sections of this application without the need to shutdown or otherwise interrupt processing occurring in other drawers. Thus, continuous workflow is maintained even in during certain failure events. In some cases, the effect of any failure in electronic, mechanical, or software components may be localized to a particular slide, group of slides or drawer, so that even if the failing component cannot be replaced in a "hot swappable" fashion, processing of other slides may be completed successfully.

Likewise, reagents may be added, removed or replaced as needed for a particular set of slides in a first drawer simultaneous with ongoing processing in other drawers. In the case that the next protocol step to be executed upon a slide or set of slide, requires a reagent that has been depleted, or is otherwise unavailable, the stainer 5452 may alert the user to provide the needed reagent. The stainer 5492 may further take steps to maintain the slide in a useable condition by hydrating with buffer or de-ionized water 5418 until the needed reagent, or an acceptable substitute reagent has been added.

Protocol steps as illustrated in FIG. 53 are non-limiting examples, which, in this case, are directed toward immunohistochemistry applications. Other slide processing applications such as special stains, in-situ hybridization, fluorescent in-situ hybridization, cytology comprise similar steps and may be similarly implemented as continuous workflow applications in accordance with the invention.

An improved method and apparatus for pre-treatment of biological samples have been disclosed and have been described according to some explanatory embodiments. Those skilled in the art can now appreciate, from the foregoing description, that the broad techniques of the embodiments of the present invention can be implemented in a variety of forms. Therefore, while the embodiments of this invention have been described in connection with particular examples thereof, the true scope of the embodiments of the present invention should not be so limited since many variations and equivalents of the method and the apparatus may be carried out without departing from the scope of the invention.

What is claimed is:

1. An apparatus for automated processing of a plurality of biological samples, said apparatus comprising:
   a plurality of independently accessible reagent holders;
   a plurality of independently accessible biological sample holders;
   at least one probe for dispensing at least one reagent;
   at least one reagent mixer;
   at least one fluid supply for supplying fluids to either the at least one probe or the at least one processing tank;
   at least one temperature controller;
   at least one distributed controller; and
   at least one computer comprising a scheduler for scheduling tasks; and
   wherein the apparatus communicates with a network comprising at least one element chosen from servers, clients, and additional apparatus;
   and wherein the network is connected to a proprietary network;
   and wherein processing of each biological sample is conducted according to a respective sequence of protocol steps;
   wherein a first biological sample, on a first sample holder, for which the processing is completed may be removed from the apparatus simultaneous with the processing of a second biological sample on a second sample holder;
   and wherein a first reagent container may be removed or replaced simultaneous with the processing of the at least one biological sample.

2. An apparatus according to claim 1, wherein the apparatus further comprises at least one processing tank.

3. An apparatus according to claim 1, wherein each independently accessible reagent holder comprises a plurality of individual reagent holders.

4. An apparatus according to claim 1, wherein each independently accessible biological sample holder comprises a plurality of individual sample holders.

5. An apparatus according to claim 1, wherein the biological sample holder is a microscope slide holder.

6. An apparatus according to claim 1, wherein the microscope slide holder is a slide clip.

7. An apparatus according to claim 3, wherein each independently accessible biological sample holder is chosen from slide racks and slide carrousels.

8. An apparatus according to claim 2, wherein each independently accessible reagent holder is chosen from reagent racks and reagent carrousels.

9. An apparatus according to claim 3, further comprising at least one drawer, wherein each drawer comprises at least one slide rack.

10. An apparatus according to claim 2, wherein each independently accessible reagent holder is chosen from reagent racks and reagent carrousels.

11. An apparatus according to claim 1, wherein the at least one probe is connected to a robotic head.

12. An apparatus according to claim 1, wherein the independently accessible biological sample holders are transported to the at least one probe.

13. An apparatus according to claim 1, wherein the at least one probe comprises a syringe pump.

14. An apparatus according to claim 1, wherein the biological sample on each biological sample holder my be immersed in the at least one processing tank.

15. An apparatus according to claim 1, wherein the at least one temperature controller is a Peltier device.

16. An apparatus according to claim 1, wherein the at least one distributed controller comprises a controller that communicates with at least one other controller that controls at least one element chosen from the at least one independently accessible reagent holder; at least one independently accessible biological sample holder; at least one probe; at least one reagent mixer; at least one fluid supply; and at least one temperature controller.

17. An apparatus according to claim 1, wherein the at least one scheduler is an adaptive scheduler.

18. The apparatus according to claim 1, wherein the at least one processing tank pretreats the biological sample.

19. The apparatus according to claim 18, wherein the pretreatment is deparaffinization.

20. The apparatus according to claim 1, wherein the apparatus further controls the temperature of at least one biological sample according to a sequence of steps in a first protocol.

21. The apparatus according to claim 1, wherein at least one reagent is dispensed on the at least one biological sample according to a sequence of steps in a first protocol.

22. The apparatus according to claim 1, wherein the apparatus further comprises at least one sample detector that detects the presence or absence of at least one sample.

23. The apparatus according to claim 1, wherein the apparatus further comprises at least one reagent detector that detects the presence or absence of at least one reagent.

24. The apparatus according to claim 1, wherein the apparatus further comprises at least one fluid detector that detects the presence or absence of at least one fluid.

25. The apparatus according to claim 1, wherein the apparatus provides continuous workflow processing of the at least one biological sample.

26. An apparatus for automated processing of a plurality of biological samples, said apparatus comprising the following elements:
   a plurality of independently accessible reagent holders;
   a plurality of independently accessible biological sample holders;
   a means for dispensing at least one reagent onto at least one biological sample holder;
   a means for mixing at least one reagent;
   a means for pre-treatment of the at least one biological sample;
   means for delivering fluid to the at least one probe and a means for delivering fluid to the means for pre-treatment; and
   at least one temperature controller;
   a first controller that receives instructions from a second controller; and
   a means for scheduling tasks;
   wherein the apparatus communicates with a network comprising at least one element chosen from servers, clients, and additional apparatus;
   and wherein the network is connected to a proprietary network.

27. The apparatus according to claim 26, wherein the means for pre-treatment comprises transporting at least one biological sample holder to at least one at least one processing tank.

28. The apparatus according to claim 26, wherein at least one biological sample holder is transported to the means for dispensing at least one reagent.

29. An automated method of processing a plurality of biological samples in an apparatus comprising:
   applying at least one reagent from a plurality of reagents to at least one first biological sample according to a sequence of steps in a first protocol;
   wherein at least one second biological sample can be added to or removed from the apparatus prior to completion of the first protocol; and
   wherein at least one second reagent can be added to or removed from the apparatus prior to completion of the first protocol;
   wherein the apparatus comprises
      a plurality of independently accessible reagent holders;
      a plurality of independently accessible biological sample holders;
      at least one probe for dispensing at least one reagent;
      at least one reagent mixer;
      at least one processing tank for at least one biological sample;
      at least one fluid supply for supplying fluids to either the at least one probe or the at least one processing tank;
      at least one temperature controller;
      at least one distributed controller; and
      at least one computer comprising a scheduler for scheduling tasks; and
   wherein the apparatus communicates with a network comprising at least one element chosen from servers, clients, and additional apparatus;
   and wherein the network is connected to a proprietary network.

30. The automated method of claim 29, wherein the apparatus further controls the temperature of the at least one first biological sample according to a sequence of steps in a first protocol.

31. The automated method of claim 29, wherein the processing includes deparaffinization.

32. The automated method of claim 29, wherein the processing includes biological staining.

33. The automated method of claim 29, wherein the processing includes in-situ hybridization.

* * * * *